US006268132B1

(12) United States Patent
Conrad

(10) Patent No.: US 6,268,132 B1
(45) Date of Patent: *Jul. 31, 2001

(54) FLUORESCENT N-NUCLEOSIDES AND FLUORESCENT STRUCTURAL ANALOGS OF N-NUCLEOSIDES

(75) Inventor: Michael J. Conrad, San Diego, CA (US)

(73) Assignee: Chromagen, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/039,021

(22) Filed: Mar. 13, 1998

Related U.S. Application Data

(62) Division of application No. 08/459,890, filed on Jun. 2, 1995, now Pat. No. 5,728,525, which is a division of application No. 08/292,892, filed on Aug. 18, 1994, now Pat. No. 5,652,099, which is a continuation-in-part of application No. 08/108,457, filed on Aug. 18, 1993, now abandoned, which is a continuation-in-part of application No. 08/021,539, filed on Feb. 12, 1993, now abandoned, which is a continuation-in-part of application No. 07/834,456, filed on Feb. 12, 1992, now abandoned.

(51) Int. Cl.[7] .............................. C12Q 1/68; C12P 19/34; C07H 19/00; C07H 21/00; C07H 21/02
(52) U.S. Cl. ........................... 435/6; 435/91.1; 435/91.2; 536/22.1; 536/23.1; 536/24.3; 536/24.31; 536/24.32; 536/24.33; 536/24.5; 536/25.3; 536/25.31; 536/25.32
(58) Field of Search .............................. 435/6, 91.1, 91.2; 536/22.1, 23.1, 24.3, 24.31, 24.32, 24.33, 24.5, 25.3, 25.31, 25.32

(56) References Cited

U.S. PATENT DOCUMENTS

| | | | |
|---|---|---|---|
| 3,960,840 | 6/1976 | Secrist, III et al. | 260/211.5 |
| 4,307,189 | 12/1981 | Kit | 435/6 |
| 4,670,380 | 6/1987 | Dattagupta | 435/6 |
| 4,711,955 | * 12/1987 | Ward et al. | 536/29 |
| 4,775,619 | 10/1988 | Urdea | 435/6 |
| 4,828,979 | * 5/1989 | Klevan et al. | 435/6 |
| 4,849,513 | 7/1989 | Smith et al. | 536/27 |
| 4,882,269 | 11/1989 | Schneider et al. | 435/6 |
| 4,910,300 | 3/1990 | Urdea et al. | 536/287 |
| 5,135,717 | 8/1992 | Renzoni et al. | 422/61 |
| 5,137,829 | 8/1992 | Nag et al. | 435/320.1 |
| 5,652,099 | * 7/1997 | Conrad | 435/6 |

FOREIGN PATENT DOCUMENTS

| | | |
|---|---|---|
| 2032203 | 6/1991 | (CA) . |
| 0235301 | 9/1987 | (EP) . |
| 9316094 | 8/1993 | (WO) . |

OTHER PUBLICATIONS

Conway, N.E. et al. (1989) "The introduction of reporter groups at multiple and/or specific sites in DNA containing phosphorothioate diesters" Nucleic Acids Res. Symposium Series 21:43–44, abstract.

(List continued on next page.)

Primary Examiner—Jezia Riley
(74) Attorney, Agent, or Firm—Saliwanchik, Lloyd & Saliwanchik

(57) ABSTRACT

Structural analogs of the six non-fluorescent N-nucleosides commonly found in RNA and DNA, which are inherently fluorescent under physiological conditions, are identified and methods for their preparation provided. Such analogs may be incorporated into DNA and/or RNA oligonucleotides via either enzymatic or chemical synthesis to produce fluorescent oligonucleotides having prescribed sequences. Such analogous sequences may be identical to, or the analogous complement of, template or target DNA or RNA sequences to which the fluorescent oligonucleotides can be hybridized. Methods of preparing either RNA or DNA oligonucleotide probes of the invention, intermediates used in such methods, and methods of using the probes of the invention in oligonucleotide amplification, detection, identification, and/or hybridization assays are also provided.

2 Claims, 38 Drawing Sheets

OTHER PUBLICATIONS

Takeda, T., K. Ikeda (1984) "Synthesis of oligonucleotides containing the hypermodified base, alpha–putrescinylthymine" Nucleic Acids Symp. Ser. 15:101–104, abstract.

Urdea, M. S. et al. (1988) "A Comparison of non–radioisotopic hybridization assay methods using fluorescent, chemiluminiescent and enzyme labeled synthetic oligodeoxyribonucleotide probes" Nucleic Acdis research 16:4937–4956.

Darnall, K. R. et al. (1967) "The Structure of Showdomycin, A Novel Carbon Linked Nucleoside Antibiotic Related to Uridine" PNAS 57:548–553.

Cardullo, R. A. et al. (1988) "Detection of nucleic aid hybridization by nonradiative fluorescence resonance energy transfer" Proc. Natl. Acad. Sci. USA 85:5610–5614.

Sproat, B. S. et al. (1989) "Highly efficient chemical synthesis of 2'-O–methyloligoribonucleotides and tetrabiotinylated derivatives; novel probes that are resistant to degradation by RNA or DNA specific nucleases" Nucleic Acids Research 17(9):3373–3386.

Ishizuka, M. et al. (1968) "Metabolism of Formycin and Formycin B in vivo" The Journal of Antibiotics 11(1):1–4.

Sweeney, M. J. et al. (1973) "Experimental Anittumor Activity of Pyrazomycin" Cancer Research 33:2619–2623.

Klusakabe, Y. et al. (1972) "Minimycin, A New Antibiotic" The Journal of Antibiotics 15(1):44–47.

Sawa, T. et al. (1968) "Metabolic Conversion of Formycin B to Formycin A and to Oxoformycin B in *Nocardia interforma*" The Journal of Antibiotics 11(5):334–339.

Brumbaugh, J. A. et al. (1988) "Continuous, on–line DNA sequencing using oligodeoxnucleotide primers with multiple fluorophores" Proc. Natl. Acad. Sci. USA 85:5610–5614.

Haralambidis, J. et al. (1989) "The synthesis of oolyamide–oligonucleotide conjugate molecules" Nucleic Acids Research 18(3):493–499.

Allen, D. J. et al. (1989) "Fluorescent Oligonucleotides and Deoxynucleotide Triphosphates: Preparation and Their Interaction with the Large (Klenow) fragment of *Escherichia coli* DNA Polymerase 1" Biochemistry 28:4601–4607.

Agrawal, S., P. C. Zamecnik (1990) "Site specific functionalization of oligonucleotides for attaching two different reporter groups" Nucleic Acids Research 18(18):5419–5423.

Keller, G. H. et al. (1988) "A chemical method for introducing haptens onto DNA probes" Analytical Biochemistry 170:441–450.

Jablonski, E. et al. (1986) "Preparation of Oligodeoxynucleotide–alkaline phosphatase conjugates and their use as hybridization probes" Nucleic Acids Research 14(15):6115–6128.

Forster, A. C. et al. (1985) "Non–radioactive, hybridization probes prepared by the chemical labeling of DNA and RNA with a novel reagent, photobiotin" Nucleic Acids Research 13(3):745–761.

Bayer, E. A., M. Wilchek (1980) "The Use of the Aviden–Biotin Complex as a Tool in Molecular Biology" Methods of Biochemical Analysis 26:1–45.

Lee, W. T., D. H. Conrad (1984) "The Murine Lymphocyte Receptor for IgE" Brief Definitive Report 159:1790–1795.

Bayer, E. A. et al. (1985) "3–(N–Maleimido–propionyl) Biocytin: A Versatile Thiol–Specific Biotinylating Reagent" Analytical Biochemistry 149:529–536.

Langer, P. A. et al. (1981) "Enzymatic synthesis of biotin–labeled polynucleotides: Novel nucleic acid affinity probes" Proc. Natl. Acad. Sci. USA 78(11):663–637.

Saiki, R. K. et al. "Enzymatic Amplication of β–Globin Genomic Sequences and Restriction Site Analysis for Diagnosis of Sickle Cell Anemia" Science 230:1350–1354.

Bobo, L. et al. (1990) "Diagnosis of *Chlamydia trachomatis* Cervical Infectin by Detection of Amplified DNA with an Enzyme Immunoassay".

Viscidi, R. P. et al. "Novel Chemical Method for the Preparation of Nucleic Acids for Nonisotopic Hybridization" Journal of Clinical Microbiology 23(2):311–317.

Draper, D. E., L. Gold (1980) "A method for linking fluorescent labels to polynucleotides: Application to Studies of Ribosome–Ribonucleic Acid Interactions" Biochemistry 19:1774–1781.

Urdea, M. S. et al. (19890 "Application of A Rapid Non–Radioisotopic Nucleic Acid Analysis System tot he Detection of Sexually Transmitted Disease–Causing Organisms and Their Associated Antimicrobial Resistances" Clinical Chemistry 35(8):1571–1575.

Hor, M. et al. "A New Antibiotic, Formycin" The Journal of Antibiotics 17(3):96–99.

Aizawa, S. et al. (1965) "Studies on a New Antibiotic, Laurusin" Agr. Biol. Chem. 29(4):375–376.

Koyama, G. et al. (1966) "The Structural Studies of Formycin and Formycin B" Tetrachedron Letters 6:597–602.

Uematsu, T., R. J. Suhadolnik (1972) "Pseudouridine, Isolation and Biosynthesis of the Nucleoside Isolated from the Culture Filtrates of *Streptoverticillium ladakanus*" Biochemistry 11(25):4669–4674.

Ochi, K. et al. (1974) "Biosynthesis of Formycin" The Journal of Antibiotics 27(12):909–916.

Ward, D. C. et al. (1969) "Biochemical Studies of the Nucleoside Analogue, Formycin" The Journal of Biological Chemistry 244(12):3243–3250.

Ward, D. C. et al. (1969) "Fluorescence Studies of Nucleotides and Polynucleotides" The Journal of Biological Chemistry 244(5):1228–1237.

Weeks, I. et al. (1983) "Acridinium esters as High–Specific–Activity Labels in Immunoassay" Clin. Chem. 29(8):1474–1479.

Hideo, I. et al. (1987) "Fluorescent Nucleoside or Nucleotide" Patent Abstracts of Japan 11:259 (C–441), Abstract No. JP62059293.

Hideo, I. et al. (1988) "Fluorescent Nucleoside or Nucleotide" Patent Abstracts of Japan 12:139 (C–491), Abstract No. JP62255499.

Reisfeld, A., J. M. Rothenberg, E. A. Bayer, M. Wilchek (1987) "Nonradioactive Hybridization Probes Prepared by the Reaction of Biotin Hydrazide with DNA" Biochemical and Biophysical Research Communications 142(20:519–526.

Robins, M. J., J. S. Wilson (1981) "Smooth and Efficient Deoxygenation of Secondary Alcohols: A General Procedure of the Conversion of Ribonucleosides to 2'-Deoxynucleosides" J. Am. Chem. Soc. 103:932–933.

Silver, Marc S. and Alan R. Fersht (1982) "Direct Observation of Complexes Formed between recA Protein and a Fluorescent Single–Stranded Deoxyribonucleic Acid Derivative" Biochemistry 21:6066–6072.

Knoth et al. "Highly degenerate, inosine–containign primers specifically amply rare cDNA using the polymerase chain reaction" Nucleic Acids Research, vol. 16, p. 10932, 1988.*

Muhlegger et al. "Non–radioactive labeling and detection of nucleic acids" Biol. Chem. vol. 371, pp. 953–965, Oct. 1990.*

Devlin "Textbook of Biocemistry with clinical correlations", pp. 632–633, 812, 1982.*

* cited by examiner

Adenosine

Guanosine or Inosine

Cytidine

Thymidine or Uridine

FORMYCIN A

5-AMINO-FORMYCIN A

5-OXO-FORMYCIN A

FORMYCIN B

5-AMINO-FORMYCIN B

OXOFORMYCIN B (ONLY THE PURINE ANALOGS ARE ILLUSTRATED BELOW)

8-AZA-6-AMINO-
PURINE NUCLEOTIDE

8-AZA-4,6-DIAMINO-
PURINE NUCLEOTIDE

8-AZA-6-AMINO-4-OXO
PURINE NUCLEOTIDE

8-AZA-6-OXO-
PURINE NUCLEOTIDE

8-AZA-6-OXO-4-AMINO-
PURINE NUCLEOTIDE

8-AZA-4,6-DIOXO-
PURINE NUCLEOTIDE

8-AZA-
PURINE NUCLEOTIDE

8-AZA-4-AMINO-
PURINE NUCLEOTIDE

8-AZA-4-OXO
PURINE NUCLEOTIDE

1,N6 ETHENO
PURINE NUCLEOTIDES

1,N6 ETHENO
PYRIMIDINE NUCLEOTIDES

2'-O-(1)-NAPHTHOYL
Adenosine

2'-O-DIMETHYLSILYL-PROPOXY-
4-METHYL COUMARYL Adenosine

Using a 17 mer primer, new sequence data starts at the 42nd residue
Using a 24 mer primer, new sequence data starts at the 49th residue

| CLASS | GENERAL STRUCTURE | BASE NAME | >280nm ? | ABSORBANCE | |
|---|---|---|---|---|---|
| | | | | abs max ? | e ? |
| N-Nucleoside | Purines | 1-methyl adenine | NO | | |
| | | 2-methyl adenine | NO | | |
| | | 3-methyl adenine | NO | | |
| | | 6-methyl adenine | NO | | |
| | | 6,6-Dimethyl adenine | YES | | |
| | | 2,6-Dimethyl adenine | YES | | |
| | | 2,2-Dimethyl adenine | YES | | |
| | | 2-aminopurine | YES | 303 nm | >9500 |
| | | 2,6-Diaminopurine | YES | 304 nm | >9500 |
| | | 6-hydroxyethyl adenine | | | |
| | | 2,8-Dihydroxy adenine | | | |
| | | 8-amino adenine | | | |
| | | 1-methyl guanine | | | |
| | | 2-methyl guanine | | | |
| | | 7-methyl guanine | YES | | |
| | | 8-amino guanine | YES | | |
| | | 8-thio guanine | YES | | |
| | | 2,2-Dimethyl guanine | YES | | |
| | | 2-methylamino guanine | | | |
| | | 7-methyl hypoxanthine | YES | | |
| | | Nebularine | YES | 315 nm | |
| | | 2-hydroxy-6-thioguanine | YES | | |

FIG. 21A

| EMISSION at 25°C yes/no ? | solvent | pH ? | F | SYNTHESIS | CODE |
|---|---|---|---|---|---|
| | | | | CGN/PBO | |
| NO | | | | /PBO | F45 |
| NO | | | | /PBO | F47 |
| NO | | | | /PBO | F48 |
| NO | | | | CGN/PBO | F49 |
| YES | | | | /PBO | F52 |
| YES | | | | /PBO | F54 |
| YES | | | | /PBO | F56 |
| 370 nm | H2O | 7 | 0.7 | CGN/PBO | F57 |
| 350 nm | H2O | 7 | 0.01 | /PBO | F58 |
| | | | | | |
| | | | | | |
| NO | | | | /PBO | F60 |
| YES | | | | /PBO | F62 |
| | | | | CGN/PBO | F63 |
| YES | | | | /PBO | F64 |
| | | | | /PBO | F65 |
| | | | | /PBO | F67 |
| | | | | | |
| YES | | | | CGN/PBO | F74 |
| YES | | | | CGN/PBO | F77 |
| | | | | /PBO | |

FIG. 21B

| CLASS | GENERAL STRUCTURE | BASE NAME | ABSORBANCE | | |
|---|---|---|---|---|---|
| | | | >280nm ? | abs max ? | e ? |
| | | 2-thiopurine | YES | 315 nm | > 20,000 |
| | | 6-mercaptopurine | YES | | |
| | | 2-amino-6-mercaptopurine | YES | 340 nm | > 20,000 |
| | | 2-hydroxy-6-mercaptopurine | YES | | |
| | Pyrazolo-[3,4d] pyrimidines | 4-amino-pyrazollo[3,4d]pyrim. | YES | 300 nm | |
| | | 1-methyl-A[3,4]PP | YES | 290 nm | |
| | | 4-methyl-A[3,4]PP | YES | 305 nm | |
| | | 7-methyl-A[3,4]PP | YES | 260 - 320 nm | |
| | | 2-methyl-A[3,4]PP | YES | 300 nm | |
| | | 6-methyl-A[3,4]PP | YES | 260-320 nm | |
| | | 2,6-Dimethyl-A[3,4]PP | | | |
| | | 2,4-Dimethyl-A[3,4]PP | | | |
| | | 1,4-Dimethyl-A[3,4]PP | | | |
| | | 4-Mercapto-A[3,4]PP | | | |
| | | 4-Methylthio-A[3,4]PP | | | |
| | | 4-Benzylamino-A[3,4]PP | | | |
| | | 4,4-Dimethylamino-A[3,4]PP | | | |
| | | 4-Hydrazino-A[3,4]PP | | | |
| | | 4-Hydroxamino-A[3,4]PP | | | |
| | | 4-Methylamino-A[3,4]PP | | | |
| | | 4-Methoxy-A[3,4]PP | | | |
| | | 4-p-nitrobenzythio-A[3,4]PP | | | |

FIG. 21C

| EMISSION at 25°C | | | | SYNTHESIS | CODE |
|---|---|---|---|---|---|
| yes/no ? | solvent | pH ? | F | CGN/PBO | |
| | | | | /PBO | |
| | | | | /PBO | |
| | | | | /PBO | |
| | | | | /PBO | |
| 430 nm | H2O | 3 | 0.06 | CGN/PBO | A[3,4]PP |
| 365 nm | H2O | 3 | 0.02 | | F141 |
| 460 nm | H2O | 7 | 0.08 | CGN/PBO | F144 |
| 430 nm | H2O | 11 | 0.16 | CGN/PBO | F143 |
| 430 nm | H2O | 3 | 0.09 | CGN/PBO | |
| 360 nm | H2O | 3 | 0.08 | CGN/PBO | F148 |
| YES | | 11 | | CGN/PBO | F145 |
| | | | | | |
| | | | | CGN/PBO | F146 |
| | | | | | |
| | | | | CGN/PBO | F147 |
| | | | | CGN/PBO | F148 |
| | | | | CGN/PBO | F149 |

FIG. 21D

| CLASS | GENERAL STRUCTURE | BASE NAME | >280nm ? | ABSORBANCE abs max ? | e ? |
|---|---|---|---|---|---|
| | | 4-amino-3-formidate-A[3,4]PP | | | |
| | | 4-amino-3-thiocarbamate-A[3,4]PP | | | |
| | | 4-amino-3-cyano-A[3,4]PP | | | |
| | | 4-amino-3-carboxamide-A[3,4]PP | | | |
| | | 4-amino-3-carboxyl-A[3,4]PP | | | |
| | | 3-aminohydroxycarboxamide-4-A[3,4]PP | | | |
| | | 4-amino-3-methyl-A[3,4]PP | | | |
| | Pyrollo-[2,3d] pyrimidines | 4-amino-pyrollo[2,3d]pyrim. | YES | | |
| | | 5-methyl-A[2,3]PP | YES | | |
| | | 5-cyano-A[2,3]PP | YES | | |
| | | 5-amino-A[2,3]PP | YES | | |
| | | 6-cyano-A[2,3]PP | YES | | |
| | | 6-amino-A[2,3]PP | YES | | |
| | | 5-carbamoyl-A[2,3]PP | YES | | |
| | | 5-carbamoyl-A[2,3]PP | YES | | |
| | | 6-methyl-A[2,3]PP | YES | | |
| | | 7-deazaguanine | YES | | |
| Azanucleotides | | 8-azaadenine | | | |
| | | 8-aza-2,6-Diaminopurine | | | |
| | | 2-amino-8-azaguanine | | | |

FIG. 21E

| EMISSION at 25°C yes/no? | solvent | pH? | F | SYNTHESIS | CODE |
|---|---|---|---|---|---|
| | | | | CGN/PBO | |
| | | | | CGN/PBO | F150 |
| | | | | CGN/PBO | F151 |
| | | | | CGN/PBO | |
| | | | | CGN/PBO | |
| | | | | CGN/PBO | |
| | | | | CGN/PBO | |
| YES | H2O | 7 | | CGN/PBO | A[2,3]PP |
| | | | | | |
| YES | H2O | 7 | | CGN/PBO | |
| YES | | | | /PBO | |
| | | | | /PBO | |

FIG. 21 F

| CLASS | GENERAL STRUCTURE | BASE NAME | ABSORBANCE | | |
|---|---|---|---|---|---|
| | | | >280nm ? | abs max ? | e ? |
| | | 8-azaguanine | | | |
| | | 8-azahypoxanthine | | | |
| | Deaza-nucleotides | 3-Deazaadenine | | | |
| | | 8-amino-3-deazaadenine | | | |
| | | 8-methyl-3-deazaadenine | | | |
| | | 7-Deazanebularine | | | |
| C-Nucleoside | Pyrazollo-[4,3d] pyrimidines | 7-amino- | YES | 293 nm | |
| | | | | 303 nm | |
| | | | | 303 nm | |
| | | | | 303 nm | |
| | | | | 303 nm | |
| | | 1-methyl-F105 | YES | >300 nm | |
| | | 2-methyl-F105 | YES | >300 nm | |
| | | 4-methyl-F105 | YES | >300 nm | |
| | | 5-amino-Pyrazollo-[4,3d] pyrim | YES | >300 nm | |
| | | 2,5-anhydro-F105 | YES | >300 nm | |
| | | 7-methyl-F105 | YES | >300 nm | |
| | | 6-methyl-F105 | YES | >300 nm | |
| | | 4,2-Dimethyl-F105 | YES | >300 nm | |

FIG. 21G

| EMISSION at 25°C | | | | SYNTHESIS | CODE |
|---|---|---|---|---|---|
| yes/no ? | solvent | pH ? | F | CGN/PBO | |
| YES | | | | /PBO | |
| | | | | | |
| | | | | | |
| | | | | | |
| | | | | | |
| 400 nm | H2O | 7 | | /PBO | |
| | | | | | |
| 348 nm | H2O | 7 | 0.06 | /PBO | F105 |
| 405 nm | H2O | 11 | 0.07 | /PBO | |
| 405 nm | ETOH | 11 | 0.12 | /PBO | |
| 405 nm | PropGlycol | 11 | 0.23 | /PBO | |
| 405 nm | DMF | 11 | 0.24 | /PBO | |
| 355 nm | H2O | 11 | 0.09 | CGN/PBO | F164 |
| 360 nm | H2O | 11 | 0.085 | CGN/PBO | F165 |
| 445 nm | H2O | 11 | .09 - 0.1 | CGN/PBO | F172 |
| YES | H2O | 11 | 0.6 | /PBO | F142 |
| YES | H2O | 11 | | /PBO | |
| YES | H2O | 11 | | CGN/PBO | F125 |
| 440 nm | H2O | 11 | 0.002 | CGN/PBO | F120 |
| YES | H2O | | | CGN/PBO | |

FIG. 21H

| CLASS | GENERAL STRUCTURE | BASE NAME | >280nm ? | ABSORBANCE abs max ? | e ? |
|---|---|---|---|---|---|
| | | 7-methylamino-2-methyl-F105 | YES | >300 nm | |
| | | 7-keto- | YES | >300 nm | |
| | | | YES | >300 nm | |
| | | | | >300 nm | |
| | | | | >300 nm | |
| | | | | >300 nm | |
| | | 1-methyl-F132 | YES | | |
| | | 2-methyl-F132 | YES | | |
| | | 4-methyl-F132 | YES | | |
| | | 6-methyl-F132 | YES | | |
| | | 7-methyl-F132 | YES | | |
| | | 7-thio-F132 | | | |
| | | 7-methyl-1-ethyl-pyrazollo[4,3d]pyrim. | | | |
| | | 7-Dimethyl-1-ethyl-pyrazollo[4,3d]pyrim. | | | |
| | | 4,2-Dimethoxy-pyrazollo[4,3d]pyrim | | | |
| | | Oxoformycin B | YES | | |
| | | 1-methyl-Oxoformycin B | YES | | |
| | | 2-methyl-Oxoformycin B | YES | | |
| | Pyrazollo-[1,5a] 1,3,5-triazines | | | | |
| | | 4-aminopyrazollo[1,5]-triazine | YES | | |
| | | 4-ThioAPTR | YES | | |
| | | 4-methylthioAPTR | YES | | |

FIG. 21 I

| EMISSION at 25°C | | | | SYNTHESIS | CODE |
|---|---|---|---|---|---|
| yes/no ? | solvent | pH ? | F | CGN/PBO | |
| | | | | | |
| YES | | | | /PBO | |
| | | | | | |
| 348 nm | H2O | 11 | | CGN/PBO | F132 |
| 410 nm | H2O | 7 | | CGN/PBO | |
| 410 nm | H2O | 11 | | CGN/PBO | |
| 410 nm | ETOH | 11 | | CGN/PBO | |
| 410 nm | PropGlycol | 11 | | CGN/PBO | |
| 410 nm | DMF | 11 | | CGN/PBO | |
| | | | | CGN | F133 |
| | | | | CGN | F134 |
| | | | | CGN | F135 |
| | | | | CGN | F136 |
| | | | | CGN | F137 |
| | | | | CGN | |
| | | | | CGN | |
| | | | | CGN | |
| | | | | CGN | |
| | | | | /PBO | |
| | | | | /PBO | |
| | | | | /PBO | |
| | | | | | |
| | | | | /PBO | APTR |
| | | | | /PBO | |
| | | | | /PBO | |

FIG. 21J

| CLASS | GENERAL STRUCTURE | BASE NAME | ABSORBANCE | | |
|---|---|---|---|---|---|
| | | | >280nm ? | abs max ? | e ? |
| | | 4-Hydroxy-APTR | YES | | |
| | | 4-Oxo-3H-PTR | YES | | |

FIG. 21K

| EMISSION at 25°C | | | | SYNTHESIS | CODE |
|---|---|---|---|---|---|
| yes/no ? | solvent | pH ? | F | CGN/PBO | |
| | | | | /PBO | |
| | | | | /PBO | OPTR |
| | | | | | |
| | | | | | |
| | | | | | |
| | | | | | |
| | | | | | |

FIG. 21L

FLUORESCENT N-NUCLEOSIDES AND FLUORESCENT STRUCTURAL ANALOGS OF N-NUCLEOSIDES

CROSS REFERENCE TO RELATED APPLICATIONS

This application is a division of application Ser. No. 08/459,890, filed Jun. 2, 1995 now U.S. Pat. No. 5,728,525; which is a division of application Ser. No. 08/292,892, filed Aug. 18, 1994, now U.S. Pat. No. 5,652,099; which is a continuation-in-part of application Ser. No. 08/108,457, filed Aug. 18, 1993, now abandoned; which is a continuation-in-part of application Ser. No. 08/021,539, filed Feb. 12, 1993, now abandoned; which is a continuation-in-part of application Ser. No. 07/834,456, filed Feb. 12, 1992, now abandoned.

BACKGROUND OF THE INVENTION

A. Field of the Invention

The present invention relates to fluorescent structural analogs of the non-fluorescent nucleosides commonly found in DNA and RNA, methods of their derivatization and subsequent use in the synthesis of fluorescent oligonucleotides, and to their new and useful applications both as fluorescent monomers and in fluorescent oligonucleotides having prescribed sequences. Additionally, it relates to applications in which fluorescent structural analogs are substituted for specific non-fluorescent nucleosides in prescribed DNA or RNA sequences and to methods of using fluorescent oligonucleotides as hybridization reagents and probes for diagnostic and therapeutic purposes and as diagnostic and therapeutic research tools.

B. General Description of the Art

The six commonly occurring N-nucleosides which predominate in the composition of DNA and RNA from all sources have the structures shown in FIG. 1 wherein $R_6$ is H for inosine and $NH_2$ for guanosine, $R_9$ is H for uridine and $CH_3$ for thymidine. Furthermore, $R_{12}$, $R_{14}$=OH for ribonucleotides, $R_{12}$=OH, $R_{14}$=H for 2'-deoxy nucleotides, $R_{12}$=H, $R_{14}$=OH for 3'-deoxy nucleotides, and $R_{12}$, $R_{14}$=H in dideoxy nucleotides.

The six commonly occurring nucleotides do not absorb light at wavelengths >290 nm and are effectively non-fluorescent under physiological conditions. Derivatives of the commonly occurring N-nucleotides for a variety of synthetic, diagnostic, and therapeutic purposes are common, including substitutions on both the heterocyclic base and the furanose ring. These substitutions can be made at the loci shown in FIG. 2 in which $R_4$ is a reactive group derivatizible with a detectable label ($NH_2$, SH,=O, and which can include an optional linking moiety including, but not limited to, an amide, thioether, or disulfide linkage or a combination thereof with additional variable reactive groups, $R_1$ through $R_3$, e.g., $R_1$—$(CH_2)_x$—$R_2$, or $R_1$—$R_2$—$(CH_2)_x$—$R_3$—, where x is an integer in the range of 1 and 25 inclusive; and $R_1$, $R_2$, and $R_3$ can be H, OH, alkyl, acyl, amide, thioether, or disulfide); $R_5$ is H or part of an etheno linkage with $R_4$; $R_6$ is H, $NH_2$, SH, or =O; $R_9$ is hydrogen, methyl, bromine, fluorine, or iodine, or an alkyl or aromatic substituent, or an optional linking moiety including an amide, thioether, or disulfide linkage or a combination thereof such as $R_1$—$(CH_2)_x$—$R_2$, or $R_1$—$R_2$—$(CH_2)_3$—$R_3$—, where x is an integer in the range of 1 and 25 inclusive; $R_{10}$ is hydrogen, or an acid-sensitive base stable blocking group, or a phosphorous derivative, $R_{11}$=$R_{12}$=H; $R_{12}$ is hydrogen, OH, or a phosphorous derivative; $R_{14}$ is H, OH, or $OR_3$ where $R_3$ is a protecting group or additional fluorophore. The letters N and C in the N-nucleosides and C-nucleosides designate the atom at which the glycosidic covalent bond connects the sugar and the heterocyclic base. In the cases of the commonly occurring nucleosides, the bases are either adenine, guanine, cytosine, inosine, uracil, or thymine. The bases are attached to a furanose sugar, a general structure of which is shown in FIG. 3. The sugar substituents for the fluorescent analogs share the same numbering system for all R groups, but the numbering system for some of the heterocycle analogs may differ.

I. Known Methods of Labeling Nucleotides

Nucleotide sequences are commonly utilized in a variety of applications including diagnostic and therapeutic probes which hybridize target DNA and RNA and amplification of target sequences. It is often necessary, or useful, to label nucleotide sequences.

A. Labeling of oligonucleotide probes with radioisotopes. Hybridization of specific DNA or RNA sequences typically involves annealing oligonucleotides of lengths which range from as little as 5 bases to more than 10,000 bases (10 kb). The majority of oligonucleotide probes currently in research use are radioactively labeled; however, because of (a) the short half lives of the isotopes in common usage, (b) the safety requirements, and (c) the costs of handling and disposal of radioactive probes, convenient and sensitive non-isotopic methods of detection are required for hybridization diagnostic methods to achieve widespread acceptance and application.

B. Non-isotopic methods of labeling oligonucleotide probes. In general, all of the non-isotopic methods of detecting hybridization probes that are currently available depend on some type of derivatization of the nucleotides to allow for detection, whether through antibody binding, or enzymatic processing, or through the fluorescence or chemiluminescence of an attached "reporter" molecule. In most cases, oligonucleotides have been derivatized to incorporate single or multiple molecules of the same reporter group, generally at specific cyclic or exocyclic positions. Techniques for attaching reporter groups have largely relied upon (a) functionalization of 5' or 3' termini of either the monomeric nucleosides or the oligonucleotide strands by numerous chemical reactions using deprotected oligonucleotides in aqueous or largely aqueous media (see Cardullo et al. [1988] *PNAS* 85:8790–8794); (b) synthesizing modified nucleosides containing (i) protected reactive groups, such as $NH_2$, SH, CHO, or COOH, (ii) activatable monofunctional linkers, such as NHS esters, aldehydes, or hydrazides, or (iii) affinity binding groups, such as biotin, attached to either the heterocyclic base or the furanose moiety. Modifications have been made on intact oligonucleotides or to monomeric nucleosides which have subsequently been incorporated into oligonucleotides during chemical synthesis via terminal transferase or "nick translation" (see, e.g., Brumbaugh et al. [1988] *PNAS* 85:5610–5614; Sproat, B. S., A. I. Lamond, B. Beijer,P. Neuner,P. Ryder [1989] *Nucl. Acids Res.* 17:3371–3386; Allen, D. J., P. L. Darke, S. J. Benkovic [1989] *Biochemistry* 28:4601–4607); (c) use of suitably protected chemical moieties, which can be coupled at the 5' terminus of protected oligonucleotides during chemical synthesis, e.g., 5'-aminohexyl-3'-O-phosphoramidite (Haralambidis, J., L. Duncan, G. W. Tregar [1990] *Nucl. Acids Res.* 18:493–499); and, (d) addition of functional groups on the sugar moiety or in the phosphodiester backbone of the polymer (see Conway, N. E., J. Fidanza, L. W. McLaughlin [1989] *Nucl. Acids Res. Symposium Series* 21:43–44; Agrawal, S., P. C. Zamecnik [1990] *Nucl. Acids Res.* 18:5419–5423).

At the simplest, non-nucleoside linkers and labels have been attached to the 3' or 5' end of existing oligonucleotides by either enzymatic or chemical methods. Modification of nucleoside residues internal to the sequence of a DNA or RNA strand has proven to be a difficult procedure, since the reaction conditions must be mild enough to leave the RNA or DNA oligomers intact and still yield reaction products which can participate in normal Watson-Crick base pairing and stacking interactions (see FIG. 4).

C. Derivatizations of the heterocyclic base (B). Numerous methods for both cyclic and exocyclic derivatization of the N-nucleoside base have been described, including the following:

(1) Hapten labeling. DNA probes have been amino modified and subsequently derivatized to carry a hapten such as 2,4-dinitrophenol (DNP) to which enzyme-conjugated antihapten antibodies bind which subsequently can be processed using a colorimetric substrate as a label (Keller et al. [1988] *Analytical Biochemistry* 170:441–450).

(2) Amino- and thiol-derivatized oligonucleotides. Takeda and Ikeda ([1984] *Nucl. Acids Research Symposium Series* 15:101–104) used phosphotriester derivatives of putrescenyl thymidine for the preparation of amino-derived oligomers. Ruth and colleagues have described methods for synthesizing a deoxyuridine analog with a primary amine "linker arm" 12 carbons in length at $C_5$ (Jablonski et al. [1986] *Nucl. Acids Res.* 14:6115–6128). These were later reacted with fluorescein to produce a fluorescent molecule. Urdea and Horn were granted a patent in 1990 (U.S. Pat. No. 4,910,300) covering pyrimidine derivatives on which the 6-amino group at $C_4$ had been modified. 3' and 5' amino modifying phosphoramidites have been widely used in chemical synthesis or derivatized oligonucleotides and are commercially available.

(3) Labeling with photobiotin and other biotinylating agents. The high affinity of biotin for avidin has been used to bind enzymatic or chemiluminescent reagents to derivatized DNA probes (Foster et al. [1985] *Nucl. Acids Res.* 13:745–761). Biotin conjugated to other linkers has also been widely used, including biotin-NHS esters (Bayer, E. A., M. Wilchek [1980] *Methods in Biochemical Analysis* 26:1), biotin succinamides (Lee, W. T., D. H. Conrad [1984] *J. Exp. Med.* 159:1790), and biotin maleimides (Bayer, E. A. et al. [1985] *Anal. Biochem.* 149:529). Reisfeld et al. ([1987] *BBRC* 142:519–526) used biotin hydrazide to label the 4-amino group of cytidine. A patent was granted to Klevan et al. in 1989 (U.S. Pat. No. 4,828,979) for such derivatizations at the 6-position of adenine, the 4-position of cytosine, and the 2-position of guanine. These derivatizations interfere with hydrogen bonding and base-pairing and have limited uses in producing oligomers for use in hybridization.

(4) dU-Biotin labeling. Nucleoside 5'-triphosphates or 3'-O-phosphoramidites were modified with a biotin moiety conjugated to an aliphatic amino group at the 5-position of uracil (Langer et al. [1981] *PNAS* 78:6633–6637; Saiki et al. [1985] *Science* 230:1350–1354). The nucleotide triphosphate derivatives are effectively incorporated into double stranded DNA by standard techniques of "nick translation." Once in an oligonucleotide, the residue may be bound by avidin, streptavidin, or anti-biotin antibody which can then be used for detection by fluorescence, chemiluminescence, or enzymatic processing.

(5) 11-digoxigenin-ddUTP labeling. The enzyme, terminal transferase, has been used to add a single digoxigenin-11-dideoxyUTP to the 3' end of oligonucleotides. Following hybridization to target nucleic acids, DIG-ddUTP labeled hybridization probes were detected using anti-DIG antibody conjugate.

(6) AAIF. Immunofluorescent detection can be done using monoclonal Fab' fragments which are specific for RNA:DNA hybrids in which the probe has been derivatized with, e.g., biotin-11-UTP(Bobo et al. [1990] *J. Clin. Microbiol.* 28:1968–1973; Viscidi et al. [1986] *J. Clin. Microbiol.* 23:311–317).

(7) Bisulfite modification of cytosine. Draper and Gold ([1980] *Biochemistry* 19:1774–1781) introduced aliphatic amino groups onto cytidine by a bisulfite catalyzed termination reaction; the amino groups were subsequently labeled with a fluorescent tag. In this procedure, the amino group is attached directly to the pyrimidine base. Like the derivatization of uracil, these derivatizations interfere with hydrogen bonding and base-pairing and are not necessarily useful for producing efficient hybridization oligomers.

(8) Fluorophore derivatized DNA probes. Texas Red (Sulfochloro-Rhodamine) derivatized probes are commercially available which hybridize to specific target DNAs and which can be detected using a flow cytometer or a microscope. Numerous authors have reported coupling fluorophores to chemically synthesized oligonucleotides which carried a 5' or 3' terminal amino or thiol group (Brumbaugh et al. [1988] *Nucleic Acids Res.* 16:4937–4956).

(9) Direct enzyme labeling. Chemical coupling of an enzyme directly to a chemically synthesized probe has been used for direct detection through substrate processing. For example, Urdea et al. described an oligonucleotide sandwich assay in which multiple DNA probe hybridizations were used to bind target DNA to a solid phase after which it was further labeled with additional, alkaline phosphatase-derivatized hybridization probes (Urdea et al. [1989] *Clin. Chem.* 35:1571–1575).

(10) Acridinium ester labeling. A single phenyl ester of methyl acridinium is attached at a central position on an RNA or DNA probe. Hydrolysis of the ester releases an acridone, $CO_2$, and light. Because the ester on unhybridized probes hydrolyzes more quickly than the ester on probes which have hybridized to target RNA or DNA, the chemiluminescence of the hybridized probes can be distinguished from that of free probes and is used in a "hybridization protection assay" (Weeks et al. [1983] *Clin. Chem.* 29:1474–1479).

D. Derivatizations of the furanose ring (F). Methods for derivatization of the furanose ring ($R_{11}$ through $R_{14}$ in FIG. 3) and at the phosphodiester backbone of oligonucleotides ($R_{10}$ in FIG. 3) have been reported.

(1) Internucleotide linkage reporter groups $R_{10}$ site. Phosphoro-thioate esters have been used to provide a binding site for fluorophores such as monobromobimane (Conway et al. [1989] *Nucl. Acids Res. Symposium Series* 21:43–44). Agrawal and Zamecnik ([1990] *Nucl. Acids Res.* 18:5419–5423) reported methods for incorporating amine specific reporter groups (e.g., monobromobimane) and thiol specific reporter groups (e.g., fluorescein isothiocyanate) through modifying the phosphodiester backbone of DNA to phosphoramidites and phosphorothioate diesters, respectively.

(2) Glycosidic reporter groups ($R_{11}$ through $R_{14}$ sites). Smith, Fung, and Kaiser ([1989] U.S. Pat. No. 4,849,513) described syntheses for an assortment of derivatives and labels on the glycosidic moiety of nucleosides and nucleoside analogs through the introduction of an aliphatic amino group at $R_{10}$. The authors did not report or claim any uses or applications of inherently fluorescent oligonucleotides, either made chemically or enzymatically or using the fluorescent nucleoside analogs or their derivatives.

E. Limitations of non-isotopic methods for labeling oligonucleotides. In order to create non-radioactive types of detectable oligonucleotides, it has been necessary to chemically modify the nucleosides typically used in DNA and RNA probes, which has made such probe preparation expensive and laborious; in many cases the detection chemistries have also proven cumbersome and expensive to use, which has largely been responsible for their failure to find significant application in clinical laboratories. In their applications to hybridization, other limitations of chemically derivatized probes have also become apparent.

(1) Chemically derivatized dNTPs are generally not cost-effective for use as stock deoxynucleotide triphosphates in PCR amplification, hence, labeling of amplified DNA is limited to (i) amplification using previously labeled primers, or (ii) annealing with labeled hybridization probes. Use of the former frequently results in false positives during amplification owing to (i) non-specific annealing of primers to non-target segments of DNA during amplification, or (ii) contamination by amplicons present in the laboratory environment which are residual from previous amplification experiments. Expense and technical difficulties in post-hybridization processing have largely limited the applications of labeled hybridization probes to research.

(2) Base pairing is hindered for many oligomers made with derivatized nucleosides through the introduction of bulky or non-hydrogen bonding bases at inappropriate sites in a sequence. Owing to the inherent background chemiluminescence of many clinical samples, even the acridinium ester probes have failed to achieve their theoretical levels of sensitivity. The requirements for post hybridization processing have remained a limitation to such methods.

(3) It has proven difficult to provide non-radioactively labeled probes which may be inexpensively produced in large quantities.

(4) Chemiluminescent probes are short lived and samples so tested are difficult to quantify or to "reprobe" accurately.

(5) Hybridization in most cases is only inferred, is non-quantitative or only semi-quantitative, and is non-automatable.

These limitations have hindered applications of DNA and RNA hybridization probes to clinical laboratory testing and therapeutic uses.

F. Fluorescent N-nucleosides and fluorescent structural analogs. Formycin A (generally referred to as Formycin), the prototypical fluorescent nucleoside analog, was originally isolated as an antitumor antibiotic from the culture filtrates of *Nocardia interforma* (Hori et al. [1966] *J. Antibiotics, Ser.* A 17:96–99) and its structure identified as 7-amino-3-b-D-ribafuranosyl (1H-pyrazolo-[4,3d] pyrimidine)) (FIGS. 5 and 6). This antibiotic, which has also been isolated from culture broths of *Streptomyces lavendulae* (Aizawa et al. [1965] *Agr. Biol. Chem.* 29:375–376), and *Streptomyces gummaensis* (Japanese Patent No. 10,928, issued in 1967 to Nippon Kayaku Co., Ltd.), is one of numerous microbial C-ribonucleoside analogs of the N-nucleosides commonly found in RNA from all sources. The other naturally-occurring C-ribonucleosides which have been isolated from microorganisms (FIG. 4) include formycin B (Koyama et al. [1966] *Tetrahedron Lett.* 597–602; Aizawa et al., supra; Umezawa et al. [1965] *Antibiotics Ser.* A 18:178–181), oxoformycin B (Ishizuka et al. [1968] *J. Antibiotics* 21:1–4; Sawa et al. [1968] *Antibiotics* 21:334–339), pseudouridine (Uematsu and Suahdolnik [1972] *Biochemistry* 11:4669–4674), showdomycin (Darnall et al. [1967] *PNAS* 57:548–553), pyrazomycin (Sweeny et al. [1973] *Cancer Res.* 33:2619–2623), and minimycin (Kusakabe et al. [1972] *J. Antibiotics* 25:44–47). Formycin, formycin B, and oxo-formycin B are pyrazolopyrimidinenucleosides and are structural analogs of adenosine, inosine, and hypoxanthine, respectively; a pyrazopyrimidine structural analog of guanosine obtained from natural sources has not been reported in the literature. A thorough review of the biosynthesis of these compounds is available in Ochi et al. (1974) *J. Antibiotics xxiv*:909–916.

Physical properties of the nucleoside analogs. Because several of the C-nucleosides were known to be active as antibiotic, antiviral, or anti-tumor compounds, their chemical derivatization and physical properties have been extensively studied and compared to the structures and syntheses of the N-nucleosides commonly found in DNA and RNA. In the late 1960s, several structural analogs of the six commonly occurring N-nucleosides were found to be fluorescent under physiological conditions; fluorescence in the analogs results from a molecular rigidity of the heterocycle structure itself; not all the structural analogs of a given type, e.g., the C-nucleosides, are fluorescent, nor is fluorescence an exclusive or inherent property of any particular class of structural analogs. Our subsequent studies have shown that only a few of the pyrazolo and pyrolo pyrimidines and purines are fluorescent, and that the property is shared with a few other nucleoside derivatives and structural analogs including, but not limited to, several substituted N-nucleosides, azanucleosides, ethenonucleosides, and deazanucleosides, the structures of which are shown in FIGS. 5–11. Those structures in FIGS. 5–11 which are shown surrounded by boxes have been either previously reported or found to be fluorescent during development of the present invention.

Uncharacterized oligomers containing fluorescent analogs were prepared by Ward and colleagues for physical studies using then available nucleoside polymerase enzymes (Ward et al. [1969] *J. Biol. Chem.* 244:3243–3250; Ward et al. [1969] loc cit 1228–1237). There have been no recent reports in the literature of attempts to combine the use of fluorescent nucleosides or their structural analogs with the synthesis or hybridization techniques of molecular biology or to synthesize fluorescent oligonucleotides therefrom.

BRIEF SUMMARY OF THE INVENTION

The subject invention pertains to nucleoside analogs which are fluorescent. These fluorescent nucleoside analogs are useful as monomers in synthesizing and labelling nucleotide sequences. The invention further pertains to the use of these fluorescent nucleotides which can be substituted for naturally occurring nucleosides in the synthesis of oligonucleotide probes. When used as hybridization probes, the fluorescence of such oligonucleotides can be used as a diagnostic tool to detect and identify specific genetic sequences. This methodology is distinct from other non-radioactive methods of probe detection in that it does not utilize nucleotides which have been coupled to enzymes or other reactive proteins and does not require post-hybridization processing for the detection of hybridization.

As described in the Background section, there are many shortcomingsto the methods and compositions currently used in DNA and RNA probe technology. It is an object of the present invention to overcome these shortcomings of the prior art through the use of fluorescent nucleosides and their fluorescent structural analogs which can be directly incorporated into a prescribed sequence as (i) specific substitutes for a given nonfluorescent nucleotide which appear at defined locations in the complementary sequences to template or target DNA, and (ii) as labels for the identification and detection of specific sequences of template, product, amplified, or target DNA and/or RNA.

It is another object of the present invention to provide novel, inherently fluorescent nucleoside and nucleoside analogs and the novel triphosphate and phosphoramidite forms thereof, which are useful in the synthesis of labeled polynucleotide probes, amplimers, diagnostics, and therapeutics. It is a further object of the present invention to provide methods of making autofluorescent oligonucleotides capable of specific Watson-Crick base pairing with prescribed sequences of target DNA or RNA.

It is another object of the invention to provide methods of using fluorescent nucleoside analogs and oligonucleotides made therefrom and synthesized according to the methods of the present invention to identify, detect the presence of, and/or alter the function of known nucleic acid sequences of DNA and RNA. Additionally, it is an object to improve and simplify the methods of detection, and to simplify the applications and uses of DNA and RNA hybridization techniques.

In another aspect of the invention, enzymatic methods are provided for making nucleic acid probes which are complementary to, and will bind to, only the sense or only the anti-sense, but not both, strands of a DNA duplex (asymmetric synthesis). It is an important aspect of the invention that asymmetric synthesis is the necessary condition for creating rapid and quantitative nucleic acid probe tests, assays, diagnostics, and therapeutics. A significant aspect of asymmetric synthesis is its dependence on the asymmetric use of promoters, primers, or linker modified primers to direct the synthesis or isolation of oligonucleotides or oligomers using only one of the two strands of a duplex as the template.

It is yet another aspect of the invention that asymmetric synthesis makes possible the directed use of multiple different templates for concurrent synthesis of a "cocktail" of asymmetric probes which can hybridize concurrently to independent and unique target sites on a single piece of nucleic acid, genomic DNA, or chromosome. It is an important aspect of the invention of probe "cocktails" that if multiple copies of the same target sequence are present on a single genome, such as the multiple copies of the tandem repeat intergenic sequences disclosed in Example 7, a single asymmetric probe template can be used to create a "cocktail" which will bind to many targets on a single genome which are identical in sequence but widely distributed in locus on the genome.

In one aspect of the invention, fluorescent structural analogs of the commonly occurring nucleosides and their derivatives useful in the synthesis, labeling, and detection of oligonucleotidesare provided having the structural formulae of FIGS. 5 through 11. The commonly occurring nucleosides characteristically form hydrogen bonds in a specific donor/acceptor relationship, designated Watson-Crick base pairing as shown in FIG. 4. Where appropriate, specific fluorescent nucleoside analogs capable of reproducing the pattern of Watson-Crick hydrogen bond formation analogous to that of a particular commonly occurring nucleoside are provided, as indicated for, e.g., A:T and formycin:T in FIG. 4 by the donor/acceptor patterns.

In another aspect of the invention, methods of making and derivatizing the fluorescent structural analogs of the commonly occurring nucleosides are provided including the steps of derivatizing the $R_{10}$, $R_{12}$, and $R_{14}$ moieties to be (i) reactive in DNA or RNA synthesis, and/or (ii) reactive in Resonance Energy Transfer of the fluorescence from the structural analogs.

In still another aspect, methods of synthesizing and using polynucleotide probes are provided using one or more of the fluorescent structural analogs and/or their derivatized forms.

Such probes can be used to screen a sample containing a plurality of single stranded or double stranded polynucleotide chains and will label, detect, and identify the desired sequence, if present, by hybridization. It is an important aspect of the invention that the fluorescent oligonucleotide probes can be used with "solution hybridization" methods as depicted in FIGS. 12 through 18.

In accordance with the foregoing objects, the present invention comprises inherently fluorescent nucleosides which can be used to label, modify, or identify oligonucleotides made therefrom, the uses of such inherently fluorescent oligonucleotides as hybridization probes, and methods for detecting nucleotide sequences.

An important aspect of the invention is the stable fluorescence emission of the fluorophores and the use of time-resolved spectroscopy or photon counting to detect and to quantify the amount of a fluorophore present in a sample.

Additional formulae, advantages, methods of use, and novel features of the invention will be set forth in the description which follows, and in part become apparent to those skilled in the art after examination of the following, or may be learned by practice of the invention.

BRIEF DESCRIPTION OF THE DRAWINGS

FIGS. 21A–21L show specific fluorescent nucleoside analogs which have been identified and characterized as to their class, structure, chemical name, absorbance spectra, emission spectra, and methods of synthesis.

BRIEF DESCRIPTION OF THE SEQUENCES

SEQ ID NO. 1 is a synthetic oligonucleotide according to the subject invention.

SEQ ID NO. 2 is a synthetic oligonucleotide and the complement of SEQ ID NO. 1.

SEQ ID NO. 3 is a synthetic oligonucleotide and a fluorescent analog of SEQ ID NO. 2.

DETAILED DISCLOSURE OF THE INVENTION

Disclosed and claimed are novel fluorescent nucleoside analogs and methods of use of the fluorescent nucleosides in, for example, nucleic acid probes and diagnostic kits. One preferred embodiment pertains to the use of inherently fluorescent nucleoside analogs in the chemical and enzymatic synthesis of DNA hybridization probes including solid phase synthesis, template directed enzymatic polymerization and amplification using polymerase chain reaction methods. Another embodiment relates to the use of autofluorescent DNA hybridization probes in the identification of specific DNA sequences, e.g., gene mapping and the detection and diagnosis of infectious and genetic diseases.

Specifically, the subject invention pertains to nucleoside analogs which are fluorescent and which can be substituted for naturally occurring nucleosides in the synthesis of oligonucleotide probes. When used as hybridization probes, the fluorescence of such oligonucleotides can be used in a variety of procedures to detect and identify specific genetic sequences. This methodology is distinct from other non-radioactive methods of probe detection in that it does not utilize nucleotides which have been coupled to enzymes or other reactive proteins. Thus, described herein are applications of inherently fluorescent nucleoside analogs in developing hybridization techniques for routine, automatable clinical diagnosis.

The fluorescent analogs of the subject invention are of three general types: (A) C-nucleoside analogs; (B) N-nucleoside analogs; and (C) N-azanucleotide and N-deazanucleotide analogs. All of these compounds have three features in common: 1) they are structural analogs of the common nucleosides capable of replacing naturally occurring nucleosides in enzymatic or chemical synthesis of oligonucleotides; 2) they are naturally fluorescent when excited by light of the appropriate wavelength(s) and do not require additional chemical or enzymatic processes for their detection; and 3) they are spectrally distinct from the nucleosides commonly encountered in naturally occurring DNA. At least 125 specific compounds of the subject invention have been identified. These compounds, which have been characterized according to their class, structure, chemical name, absorbance spectra, emission spectra, and method of synthesis, are tabulated as shown in FIGS. 21A–21F-1.

Figure 1:
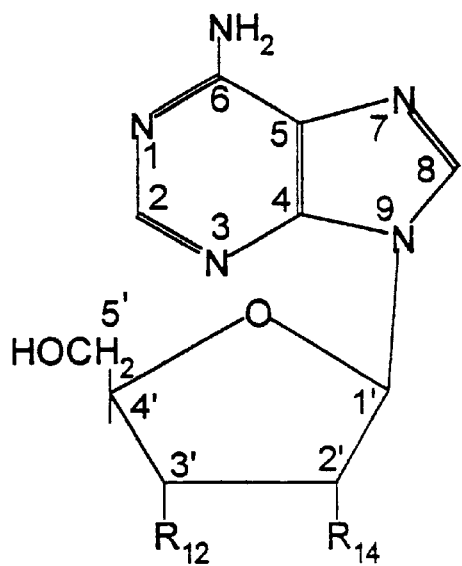
FIG. 1 shows the six commonly-occurring N-nucleosides which predominate in DNA and RNA.
Figure 1:
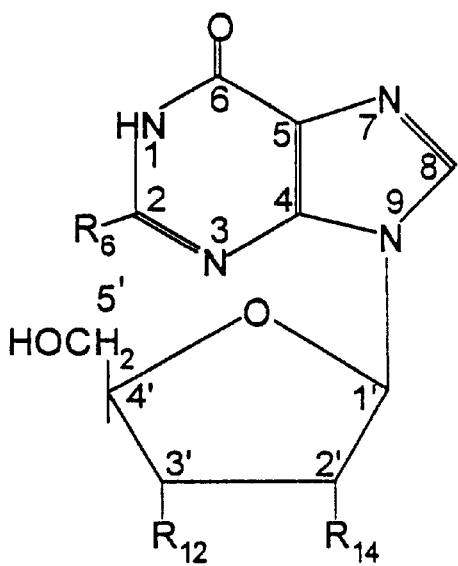
Figure 1:
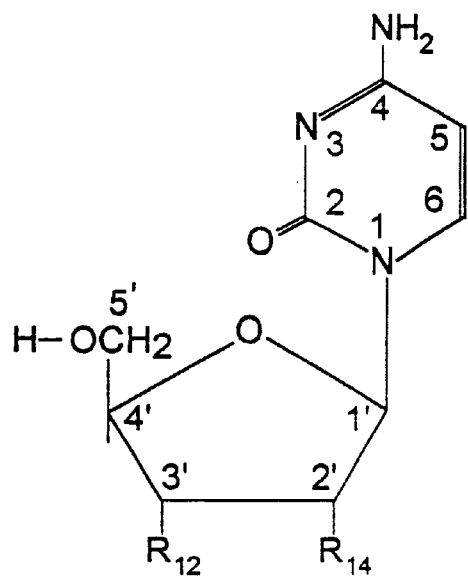
Figure 1:
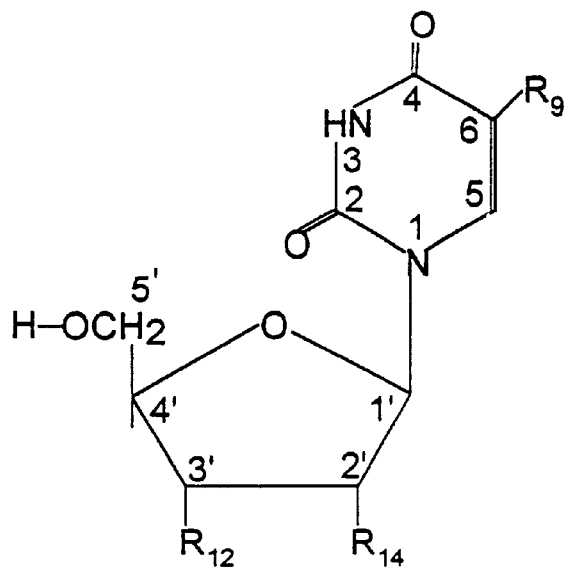

Definitions. The following definitions are provided for ease in understanding the description:

"Commonly Occurring Nucleosides" are the six monomeric N-nucleotides shown in FIG. 1, which predominate in naturally occurring DNA and RNA, enter into classical Watson-Crick base pairing, and are effectively non-fluorescent under physiological conditions. The respective one-letter symbols in sequence shorthand are A, C, G, T, U, and I for adenosine, cytidine, guanidine, thymidine, uridine, and inosine, respectively.

Figure 4:
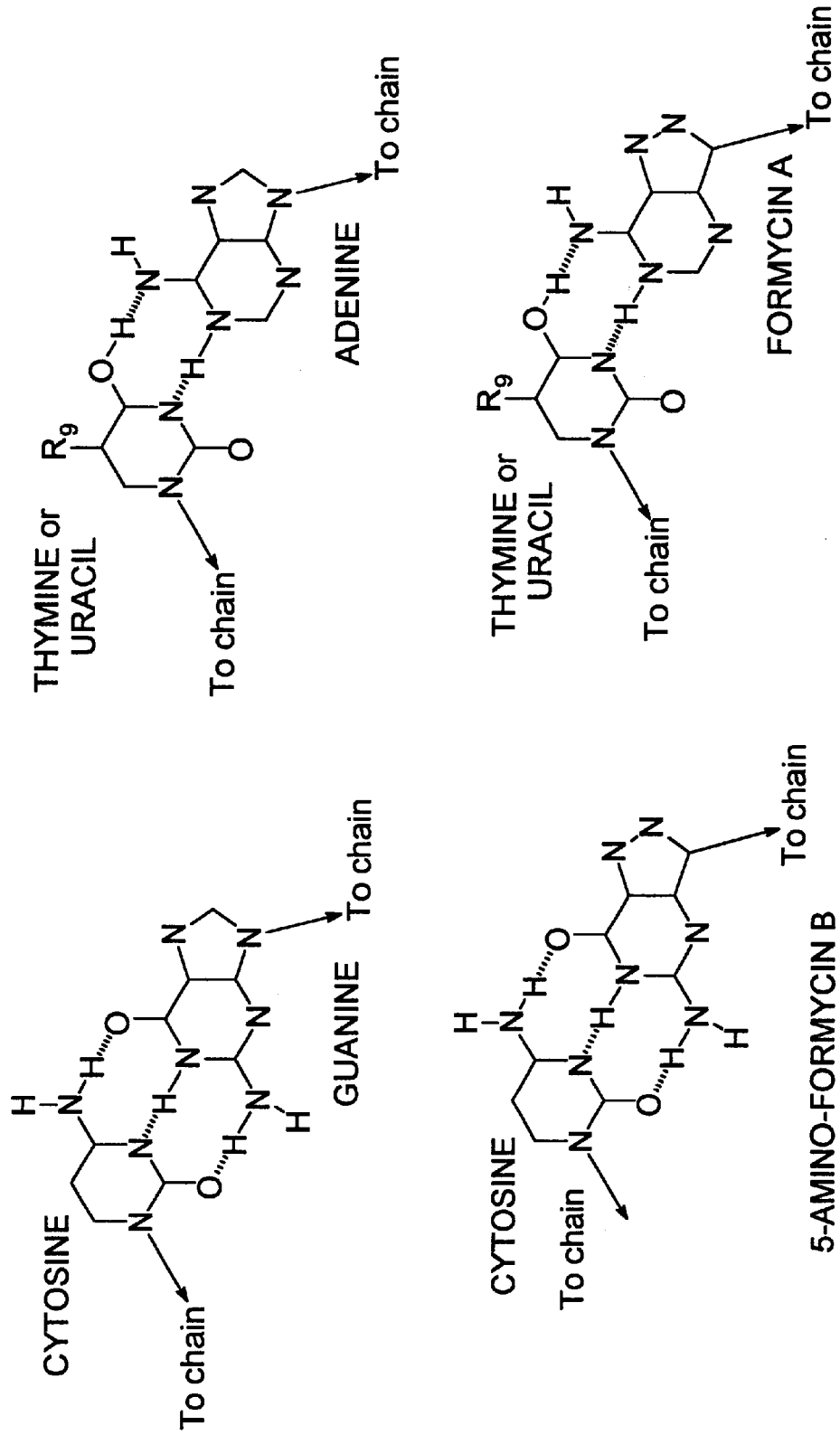
FIG. 4 shows Watson-Crick base pairing between the normally occurring N-nucleotides A:T and G:C and base pairing between formycin:T, formycin:U, 2,6-diaminopurine:T, and 5-amino-formycin B:C.
Figure 5:
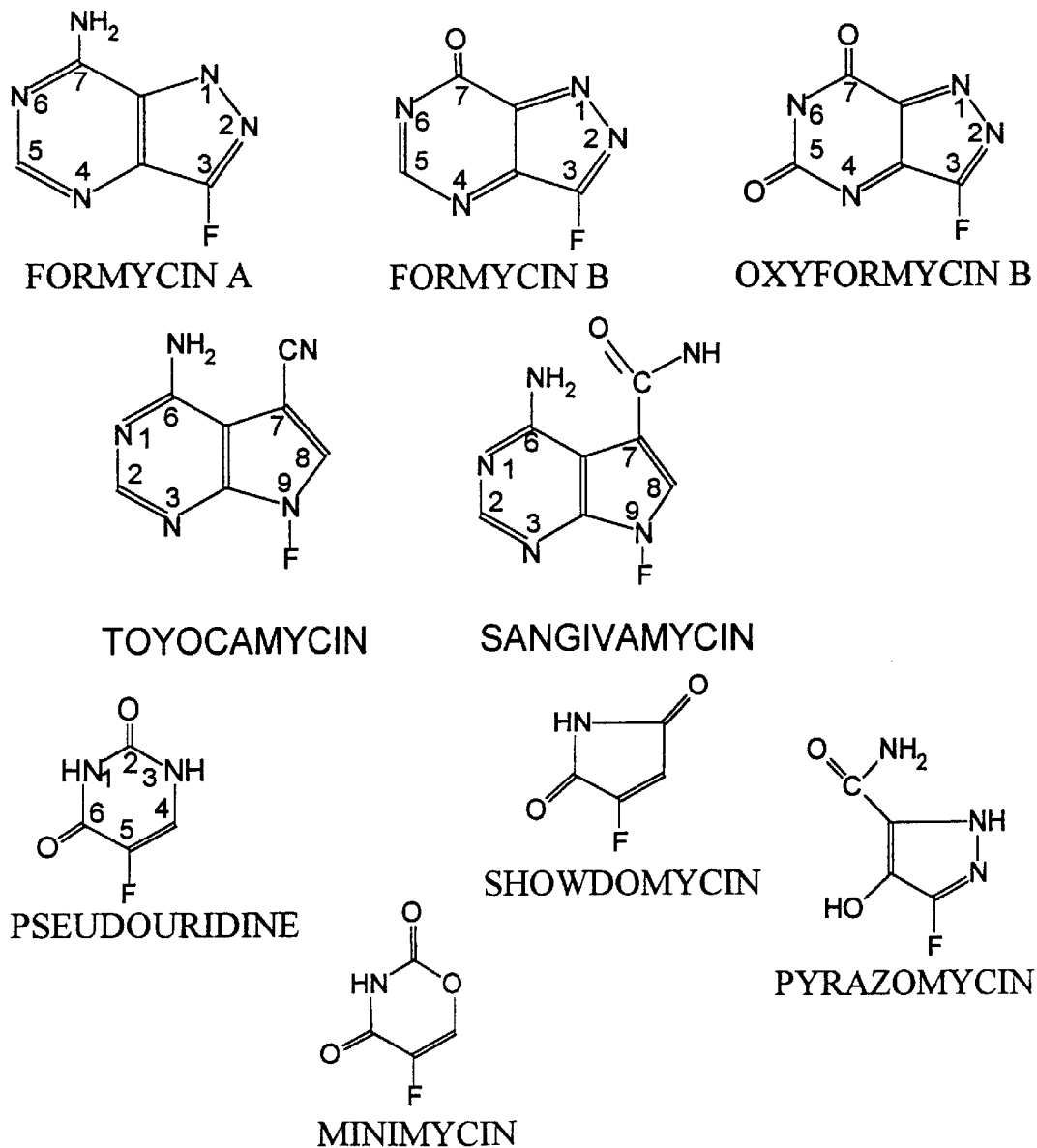
FIG. 5 shows structural analogs of the commonly-occurring N-nucleosides derived from biological sources.
Figure 6:
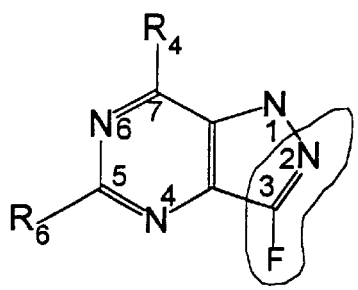
FIG. 6 shows the pyrazolo [4,3d] pyrimidine nucleoside analogs.
Figure 6:
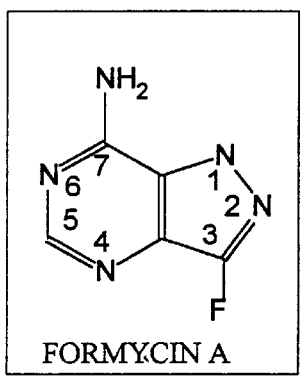
Figure 6:
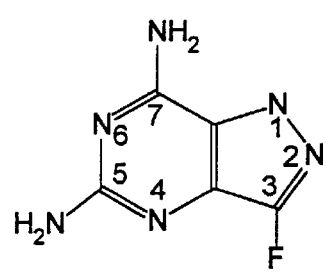
Figure 6:
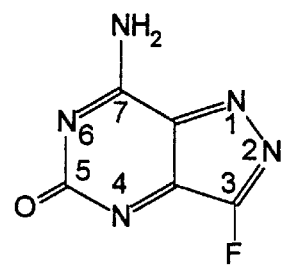
Figure 6:
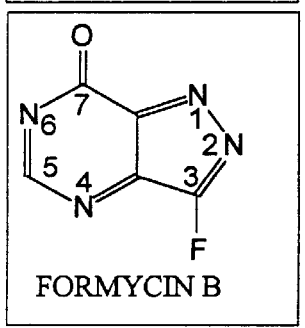
Figure 6:
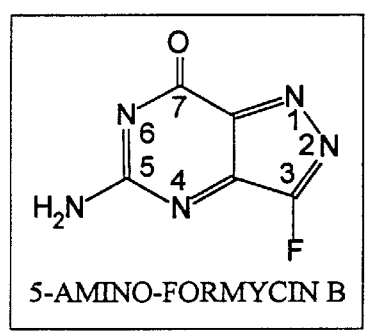
Figure 6:
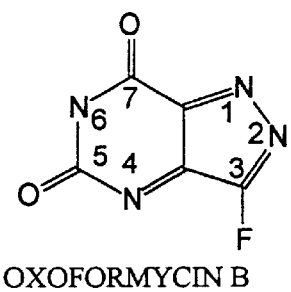
Figure 6:
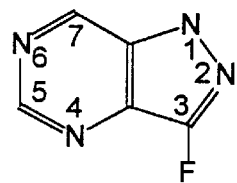
Figure 6:
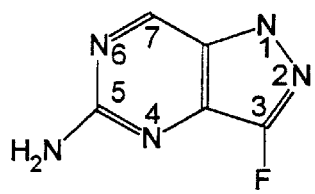
Figure 6:
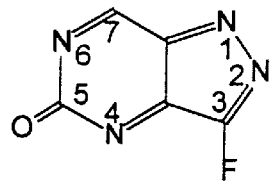
Figure 7:
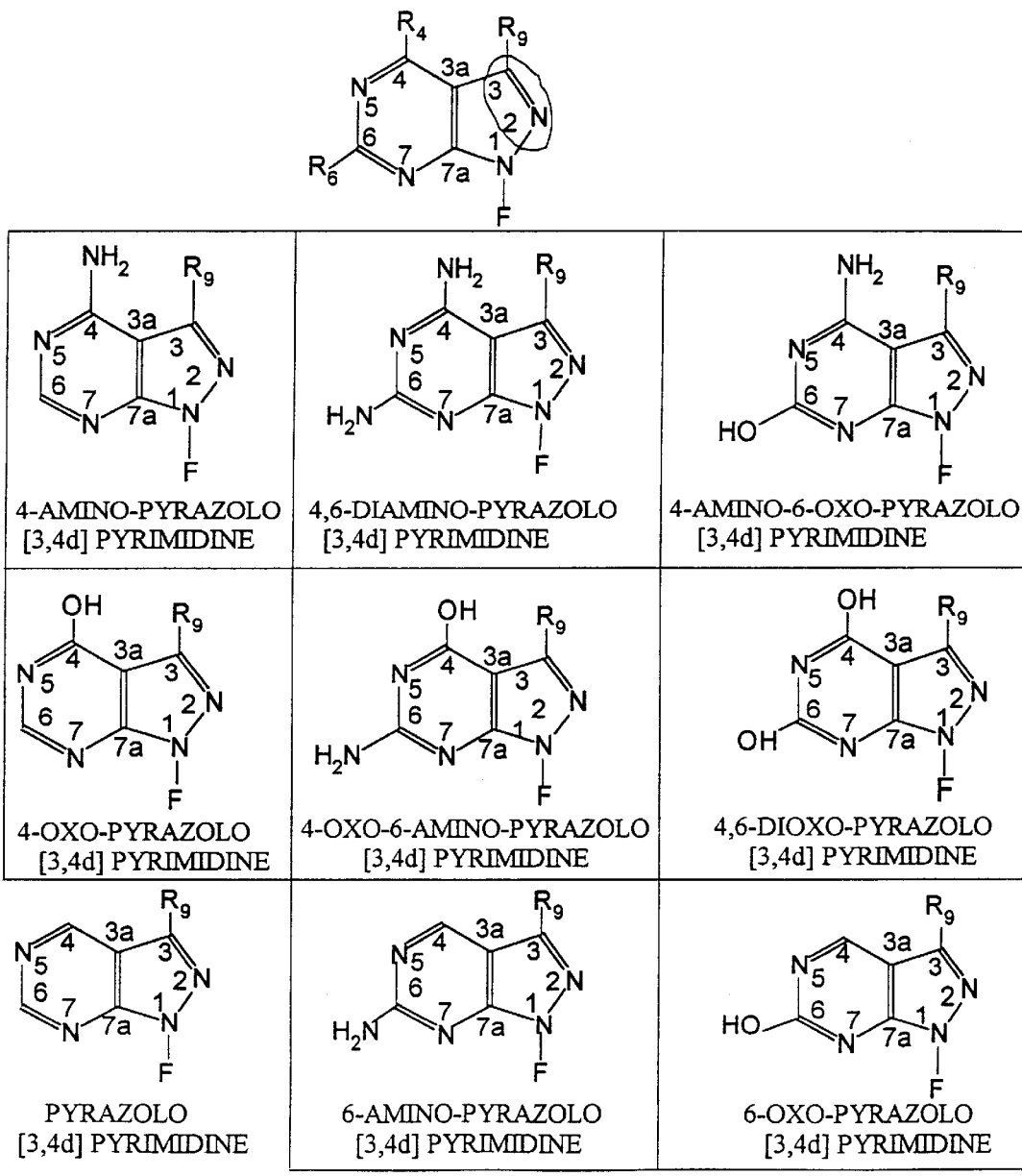
FIG. 7 shows the pyrazolo [3,4d] pyrimidine nucleoside analogs.
Figure 8:
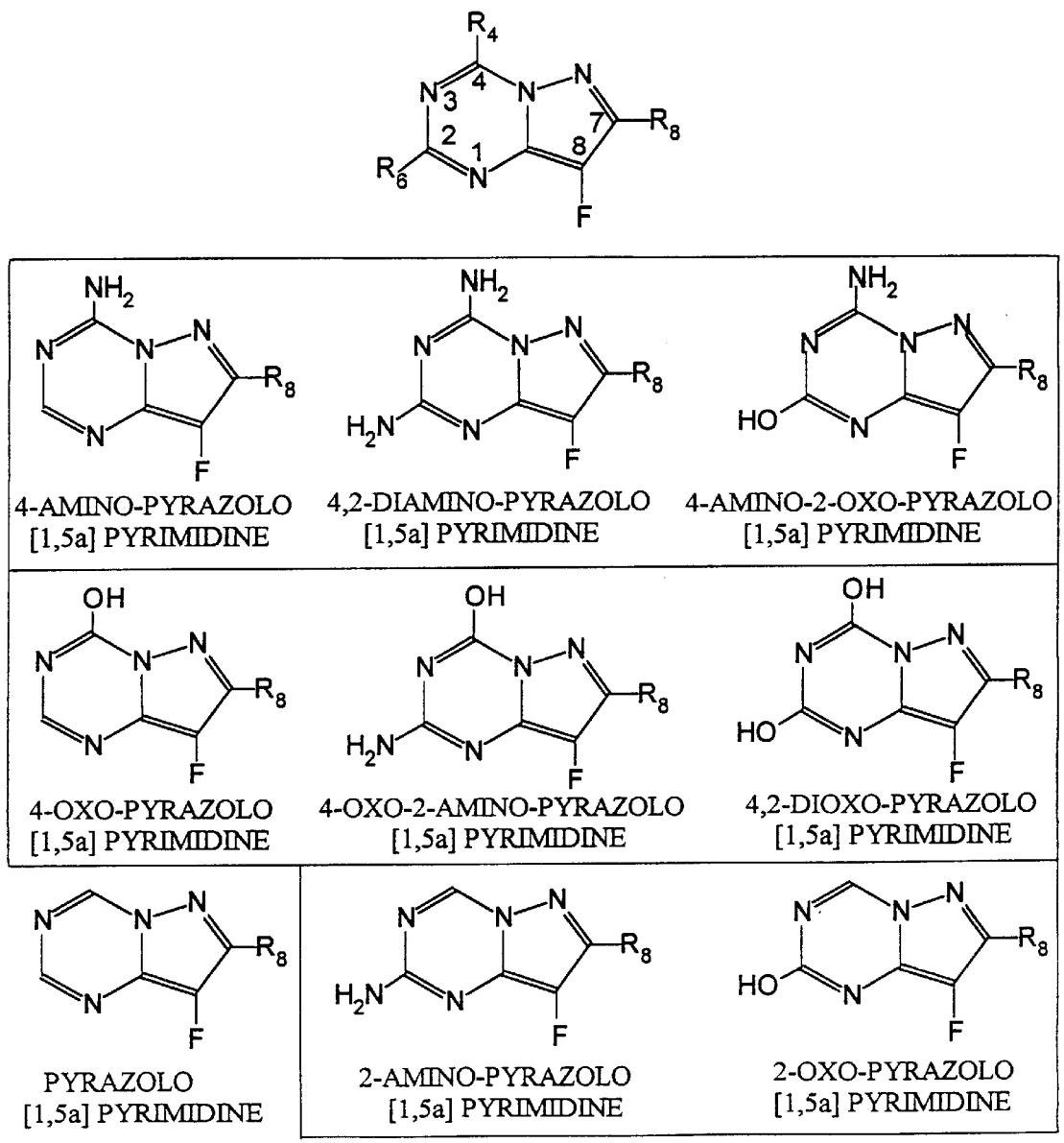
FIG. 8 shows the pyrazolo [1,5a]-1,3,5-triazine nucleoside analogs.
Figure 9:
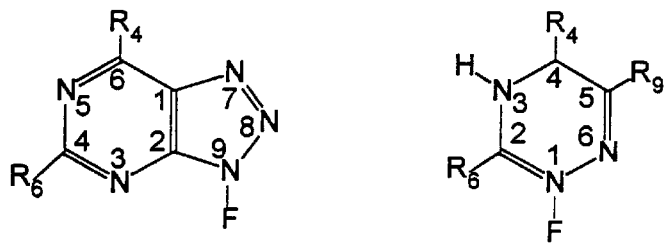
FIG. 9 shows the azapyrimidine and azapurine nucleoside analogs.
Figure 9:
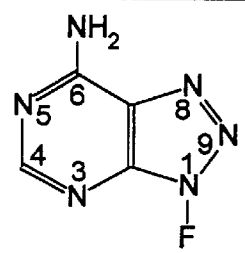
Figure 9:
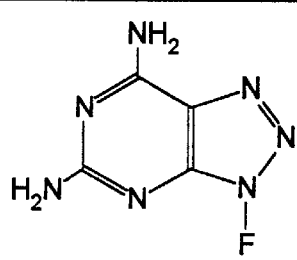
Figure 9:
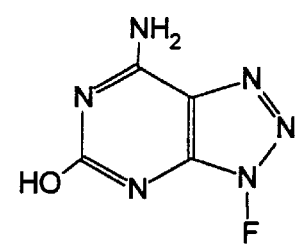
Figure 9:
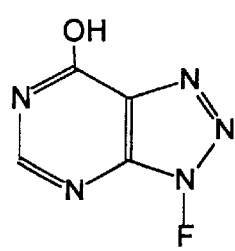
Figure 9:
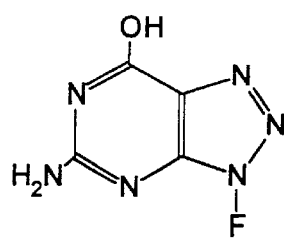
Figure 9:
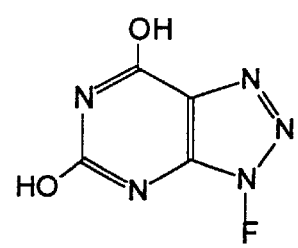
Figure 9:
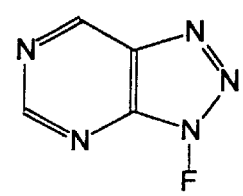
Figure 9:
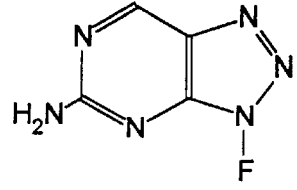
Figure 9:
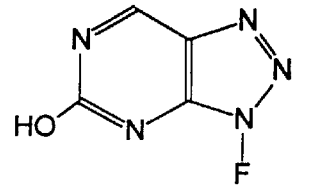
Figure 10:
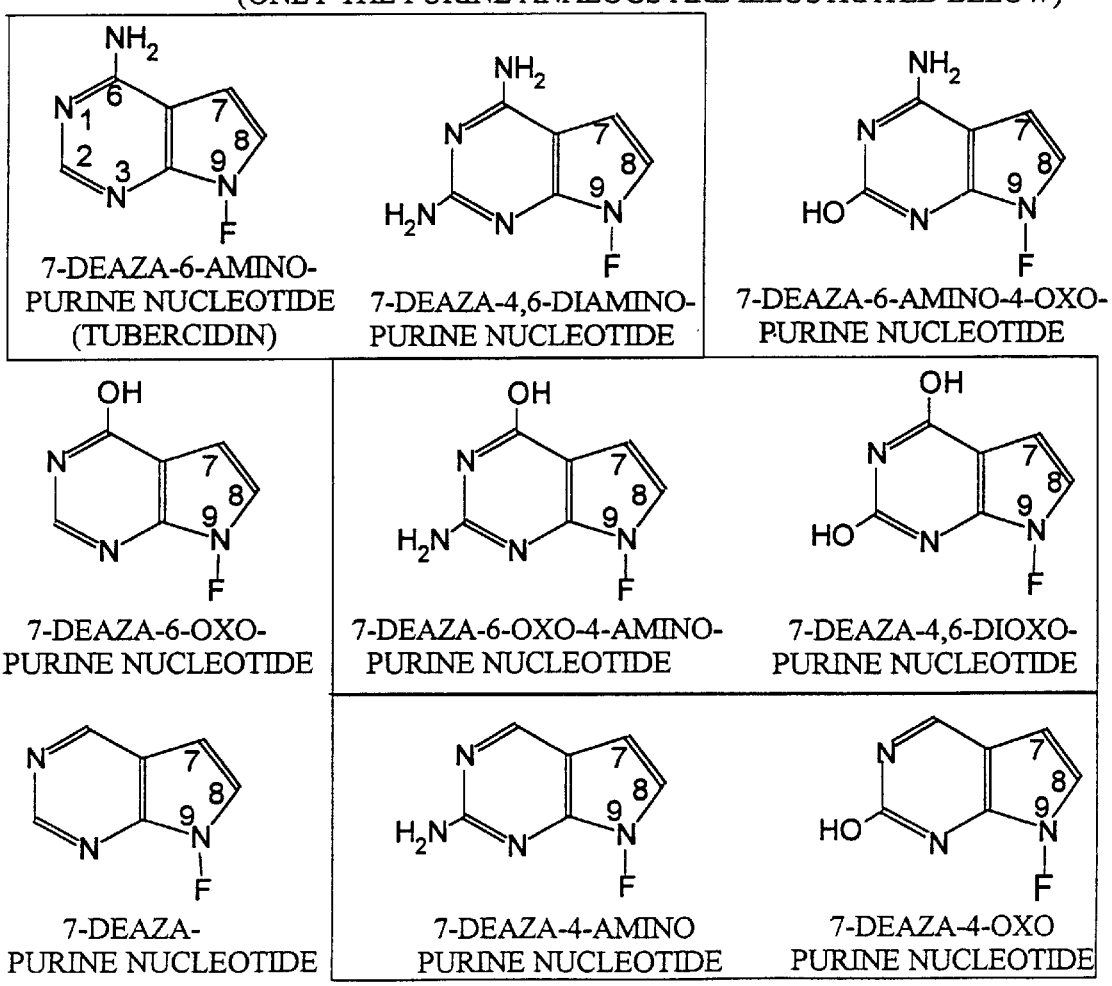
FIG. 10 shows the deazapyrimidine and deazapurine nucleoside analogs.
Figure 11A:
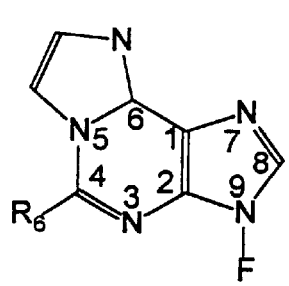
FIGS. 11A–11B shows examples of some fluorescent structural analogs which are (11A non-H-binding, and (11B) fluorescence resonance energy transfer (FRET) analogs.
Figure 11A:
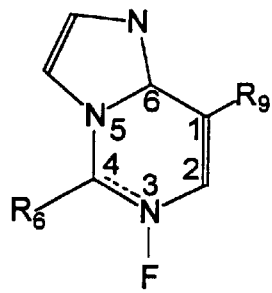
Figure 11B:
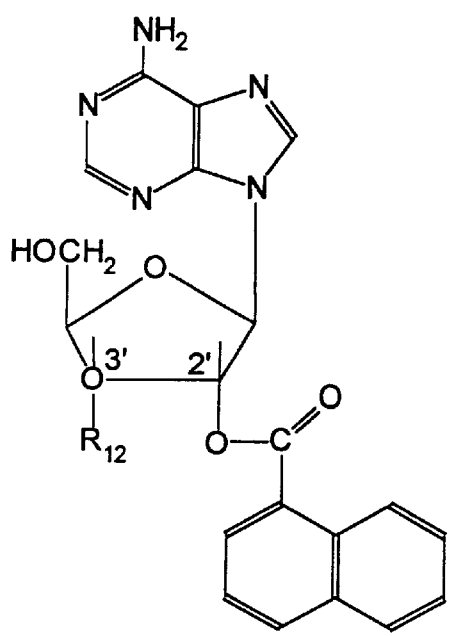
Figure 11B:
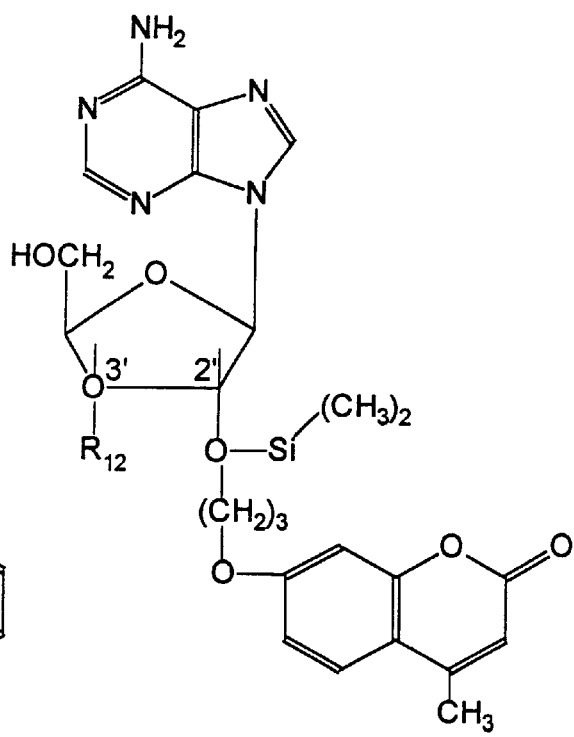

"Structural Analogs" of the commonly occurring nucleosides are structurally related molecules that mimic the normal purine or pyrimidine bases in that their structures (the kinds of atoms and their arrangement) are similar to the commonly occurring bases, but may have certain modifications or substitutions which do not affect basic biological activity or biochemical functions. Such base analogs include, but are not limited to, imidazole and its 2,4- and/or 5-substituted derivatives; indole and its 2-, 3-, 4-, 5-, 6-, and/or 7-substituted derivatives; benzimidazole and its 3-, 4-, and/or 5-substituted derivatives; indazole and its 3-, 4-, 5-, 6-, and/or 7- substituted derivatives; pyrazole and its 3-, 4-, and/or 5-substitute derivatives; triazole and its 4- and/or 5-substituted derivatives; tetrazole and its 5-substituted derivatives; benzotriazole and its 4-, 5-, 6-, and/or 7-substituted derivatives; 8-azaadenine and its substituted derivatives; 6-azathymine and its substituted derivatives; 6-azauracil and its substituted derivatives; 5-azacytosine and its substituted derivatives; 8-azahypoxanthine and its substituted derivatives; pyrazolopyrimidine and its substituted derivatives; 3-deazauracil; orotic acid; 2,6-dioxo-1,2,3,6-tetrahydro-4-pyrimidine carboxylic acid; barbituric acid; uric acid; ethenoadenosine; ethenocytidine; an allopurinol (4-hydroxy-pyrazolo [3,4d] pyrimidine); or their protected derivatives as described below. Base analogs can also be any of the C-nucleosides such as are shown in FIGS. 4 and 5 in which the normal C—N bond between the base and the furanose ring is replaced by a C—C bond; such bases include, but are not limited to, uracil, as in the C-nucleoside pseudouridine; 1-methyluracil; 1,3-dimethyluracil ; 5(4)-carbomethoxy-1,2,3-triazole; 5(4)-carboxamido-1,2,3-triazole; 3(5)-carboxymethylpyrazole; 3(5)-carbomethoxypyrazole; 5-carbomethoxy-1-methylpyrazole; maleimide (in the C-nucleoside showdomycin); and 3 (4)-carboxamido-4(3)-hydroxypyrazole (in the C-nucleoside pyrazomycin); and any of the other analogs listed or inferred in FIGS. 5 through 11; or their protected derivatives.

"Fluorophore" refers to a substance or portion thereof which is capable of emitting fluorescence in a detectable range. For the fluorescent structural analogs of the nucleotides, this fluorescence typically occurs at wavelengths in the near ultraviolet (>300 nm) through the visible wavelengths. Preferably, fluorescence will occur at wavelengths between 300 nm and 700 nm and most preferably in the visible wavelengths between 300 nm and 500 nm.

"Fluorescent Structural Analogs" are synthetic or biochemically derived monomeric structural analogs of the six commonly occurring N-nucleosides (FIG. 1), such as are depicted in FIGS. 5 through 11, which may or may not be capable of classical Watson-Crick base pairing depending upon the monomeric structure and/or oligonucleotide in which they are used, but which are spectrally unique and distinct from the commonly occurring nucleosides in their capacities for selective excitation and emission under physiological conditions. For example, the C-nucleoside formycin A is a structural analog of adenosine that can form equivalent donor/acceptor hydrogen bonds, but which has an excitation maximum in oligonucleotides at 303 nm and an emission maximum at 405 nm (Stokes Shift=102 nm).

"Derivatized" nucleoside analogs are fluorescent structural analogs in which reactive or protective functional groups are bound, covalently or otherwise, at the $R_4$ through $R_9$ positions of the heterocycle and/or the $R_{10}(5')$, the $R_{12}(3')$, and $R_{14}(2')$ positions of the glycosidic moiety. Derivatives at the 2' glycosidic position may include fluorescence resonance energy transfer (FRET) acceptors or donors which enhance or accept and re-emit at longer wavelengths the inherent fluorescence emission of the fluorescent structural analog itself.

A "polynucleotide," "oligonucleotide," or "oligomer" is a nucleotide chain structure containing at least two commonly occurring nucleotides or fluorescent structural analogs. The "fluorescentoligonucleotideprobe" or "fluorescenthybridizationprobe" provided herein is a nucleotide chain structure, as above, containing at least two monomers, at least one of which is fluorescent.

"Hybridization" is the pairwise annealing through Watson-Crick base pairing of two complementary, single-stranded molecules (see FIG. 4), which may be DNA:DNA, DNA:RNA, or RNA:RNA, and in which the two strands may come from different sources. The annealing is specific (i) for complementary base pairs in which the hydrogen bond donors and acceptors are oriented as in FIG. 4, and (ii) for the complementary genetic sequence of the specific gene, target DNA, or target RNA (hereinafter "target DNA/RNA") to which the probe is to be hybridized. Compare, for example, the hydrogen bond pattern of adenosine and formycin (FIG. 4).

"DNA/RNA Melting Temperature" and "Tm" refer to the temperature at which the hydrogen bonds between hybridized strands of DNA or RNA are disrupted and the strands disassociate into single strands, thereby disrupting the structure of the duplex or hybrid.

"Analogous fluorescent sequence" refers to the nucleoside sequence of a polynucleotide which has been synthesized by any of the enzymatic or chemical methods described in the present invention, but in which fluorescent nucleoside analogs have been explicitly substituted for particular commonly occurring nucleosides, e.g., the substitution of formycin A-5'-triphosphate (FTP) for adenosine-5'-triphosphate (ATP), when using RNA polymerase to produce RNA probes complementary to a prescribed DNA template. In an analogous fluorescent sequence, the fluorescent nucleoside analog has been substituted in the oligonucleotide chain at some or all positions in which the corresponding commonly occurring nucleotide would have occurred in the sequence as dictated by, e.g., the template, in the case of enzymatic synthesis. Similar programmed substitutions can be made using 3'-O-phosphoramidites of the individual fluorescent analogs during standard phosphotriester synthesis. Thus, for example, the complementary sequence of the Chlamydia tracheomatis MOMP gene, or its fluorescent analogous sequence, can be synthesized enzymatically using dATP or dFTP, respectively, in the presence of DNA polymerase, dCTP, dTTP, and dGTP:

MOMP GENE SEQUENCE (SEQ ID NO. 1):
AAC GTT CGA GAC GGA CAC CCC TTA GGA CGA CTT GGT TCG

COMPLEMENT SEQUENCE (SEQ ID NO. 2):
TTG C<u>AA</u> GCT CTG CCT GTG GGG <u>AAT</u> CCT GCT G<u>AA</u> CC<u>A</u> <u>A</u>GC

-continued

ANALOGOUS FLUORESCENT SEQUENCE (SEQ ID NO. 3):
TTG CFF GCT CTG CCT GTG GGG FFT CCT GCT GFF CCF
FGC wherein the fluorescent deoxyformycin A (F) residues underlined in the analogous sequence are the structural analogs of the deoxyadenosine (A) residues in the same relative positions in the complementary sequence.

"FRET acceptor" or "Fluorescence Resonance Energy Transfer acceptor" refers to a substance, substituent, chromophore, or fluorophore, e.g., a dansyl, naphthyl, anthryl, pyrenyl, methylumbelliferone, or coumarin moiety, which is capable of absorbing emitted light from fluorescent structural analog donors and re-emitting that energy at other, longer wavelengths. In the context of the present invention, such secondary fluorophores may be selectively excited as a second label, or may be used as a fluorescence acceptor to broaden and enhance the primary fluorescence of the structural analog energy donor.

A. Structures, Sources, Synthesis, and Derivatization of the Fluorescent Nucleoside Analogs Briefly, the present invention includes the heterocyclic pyrimidine or purine structural analogs of the commonly occurring nucleoside bases (B) which are fluorescent under physiological conditions and which are linked by a carbon-carbon or carbon-nitrogen bond to the set of furanose rings (designated F in FIGS. 4–9) of ribose ($R_{12}=R_{14}=OH$), deoxyribose ($R_{12}=H$, $R_{14}=OH$, or $R_{12}=OH$, $R_{14}=H$), or dideoxyribose ($R_{12}=R_{14}=H$) and their derivatives such as are described below, and/or are apparent to one familiar with nucleotide chemistry.

For the present invention, formycin, 2-amino purine ribonucleoside, and 2,6-diamino ribonucleoside, all of which can (i) form the same or related base-pairing hydrogen bonds as adenosine, and (ii) substitute specifically for adenosine in Watson-Crick base pairing as well as in a wide variety of enzymatic reactions including nucleic acid replication, ligation, and phosphorylation, are used as representatives of the set of fluorescent nucleosides and nucleoside analogs (FIG. 4). Related properties and parallel claims obtain in the present invention for all other fluorescent analogs of guanosine, cytidine, thymidine, uridine, inosine, and their derivatives.

(1) Structures of the nucleoside analogs. The generic purine and pyrimidine structures of each type of structural analog to the commonly occurring nucleosides are given at the top of each of FIGS. 5 through 11, below which are representative examples of each class of analog. Only examples of the purine analogs are given in FIGS. 6 and 7, since the known pyrimidine analogs have already been illustrated in FIG. 5. With the exception of the N-nucleoside analogs, which have only substitutions at $R_4$, $R_6$, and $R_9$, the generic structures at the top of each page show an oval encircling the part of the structure where substitutions to the heterocyclic base distinguish the analog from the commonly occurring N-nucleosides shown in FIG. 1.

Figure 2:
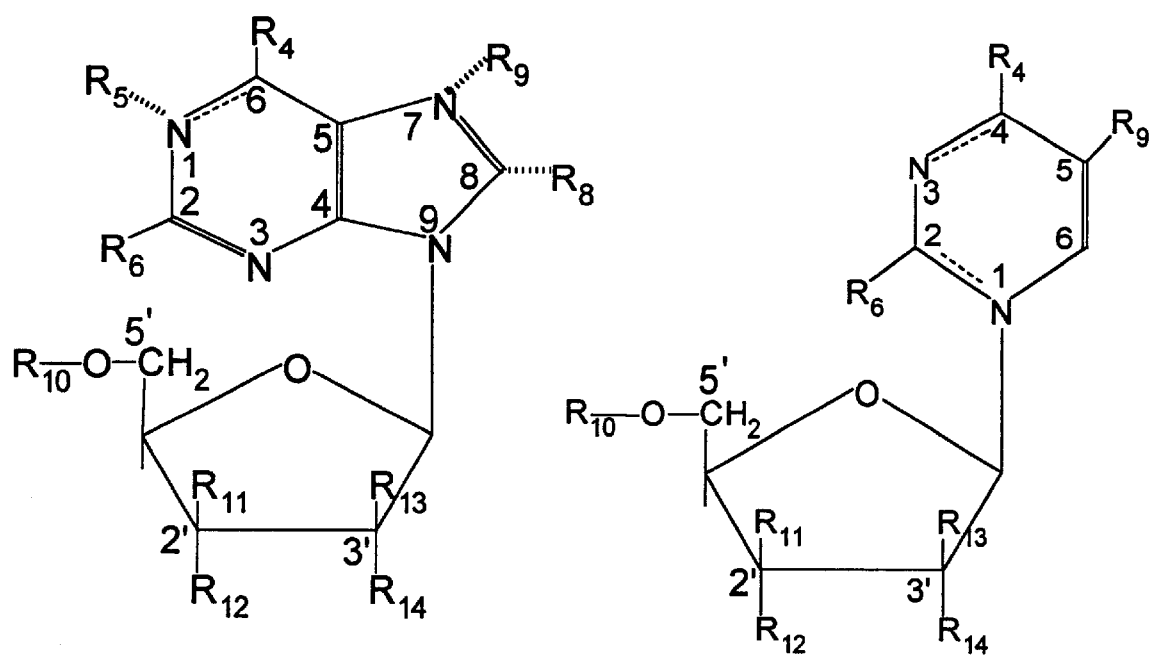
FIG. 2 shows the general structures of the commonly-occurring N-nucleosides and their derivatization sites, $R_n$.
Figure 3:
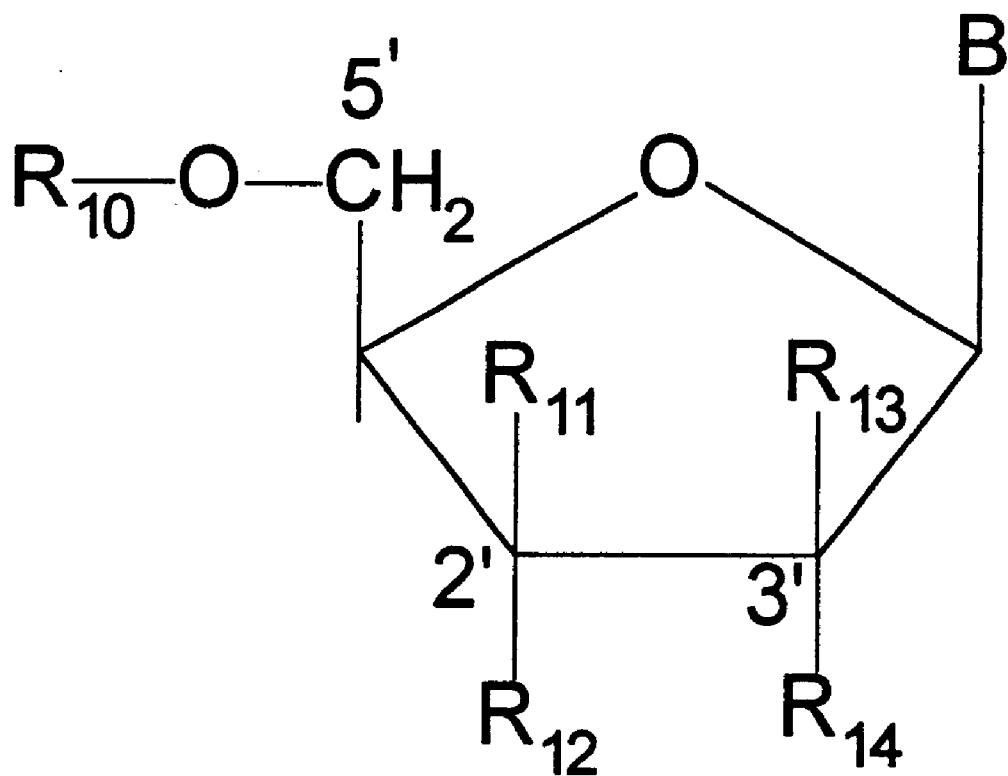
FIG. 3 shows the general structure of the furanose ring of both the purine and pyrimidine nucleosides and the common sites, $R_n$ for derivatization.

(2) Furanose moieties common to the fluorescent nucleoside analogs. The numbering of the sugar carbon atoms in furanose is 1' to 5' as indicated in FIG. 2; thus the base, B, is connected to C1 of the sugar. The furanose moiety of any fluorescent heterocycle claimed in this invention has, in common with all other analogs, the set F, of glycosides and substituted glycosides, as follows: substitutions can be made, in principle, at any of the 5 sugar carbons; the subset F is defined by derivatives and/or substitutions at positions $R_{10}$, $R_{11}$, $R_{12}$, $R_{13}$, and $R_{14}$, which (i) are apparent to one skilled in the art, and (ii) are the furanosyl derivatives of all the fluorescent nucleoside analogs claimed in the present invention. These include all phosphorous substitutions (e.g., triphosphate, thiophosphate, aminophosphate, etc.) and all protecting substitutions (e.g., dimethoxytrityl) at position $R_{10}$. For all glycosides, F, in FIGS. 5 through 11, $R_{10}$, $R_{11}$, $R_{12}$, $R_{13}$ and $R_{14}$ are defined as follows: $R_{11}$ and $R_{13}$=H; $R_{14}$=H, OH, or $OR_i$; $R_{12}$ and $R_{10}$ are either H, OH, $OR_m$, or $NHR_K$, wherein (a) $R_i$ protecting groups are typically lower aryl or alkyl ether, e.g., methyl, t-butyl, benzyl, o-nitrobenzyl, p-nitrobenzyl, o-nitrophenyl, or triphenylmethyl; or a lower alkyl or aryl ester such as acetyl, benzoyl, or p-nitrobenzoyl, or an alkyl; acetal such as tetrahydropyranyl; or a silyl ether, such as trimethylsilyl or t-butyl-dimethylsilyl; or a sulfonic acid ester such as p-toluenesulfonyl or methanesulfonyl; or halide such as bromine, fluorine, or iodine. Additional examples of suitable blocking groups may be found in Green, T.W. (1981) *Protective Groups in Organic Synthesis*, New York: Wiley & Sons. Alternatively, $R_{14}$ may be a FRET derivative including, but not limited to, such fluorophores as 7-[3-(chlorodimethylsilyl)propoxy]-4-methylcoumarin, O-4-methylcoumarinyl-N-[3-triethoxysilyl)propylcarbamate, and N-3-triethoxysilylpropyl)dansylamide(b) $R_m$ represents an appropriate protecting, substituting, or reactive linker group including 2' or 3'-amido, 2' or 3'-azido, 2',3'-unsaturated, and the subset of phosphorous derivatives involved in chemical or enzymatic syntheses of oligonucleotides having a phosphate ester, thiophosphate ester, or aminophosphate ester backbone; (c) $R_k$ is any common, standard nitrogen protecting group, such as those commonly used in peptide synthesis (Geiger, R., W. Konig [1981] In *The Peptides: Analysis, Synthesis, Biology*, Vol. 3, E. Gross, J. Meienhofer, eds., Academic Press, New York, pp. 1–99); this includes, but is not limited to, acid-labile protecting groups such as formyl, t-butyloxycarbonyl, benzyloxycarbonyl, 2-chlorobenzyloxycarbonyl, 4-chlorobenzyloxycarbonyl, 2,4-dichlorobenzyloxycarbonyl, furfuryloxycarnonyl, t-amyloxycarbonyl, adamantyloxycarbonyl, 2-phenylpropyl-(2)-oxycarbonyl, 2-(4-biphenyl)propyl-(2)-oxycarbonyl, triphenylmethyl, p-anisyldiphenylmethyl, di-p-anisyl diphenylmethyl, 2-nitrophenylsulfenyl, or diphenylphosphinyl;base labile protecting groups such as trifluoroacetyl, 9-fluorenylmethyloxycarbonyl, 4-toluene-sulfonylethyloxycarbonyl, methylsulfonylethyloxycarbonyl, and 2-cyano-t-butyloxycarbonyl; as well as others, such as chloroacetyl, acetoacetyl, 2-nitro-benzoyl, dithiasuccinoyl, maleoyl, isonicotinyl, 2-bromoethyloxycarbonyl, and 2,2,2-trichloroethyloxycarbonyl; alternatively, $R_k$ may also be any reactive group derivatizible with a detectable label ($NH_2$, SH, =O, and which can include an optional linking moiety including an amide, thioether or disulfide linkage, or a combination thereof with additional variable reactive groups $R_1$ through $R_3$, such as $R_1$-$(CH_2)_x$-$R_2$, where x is an integer in the range of 1 and 8, inclusive; and $R_1$, $R_2$, and $R_3$ are H, OH, alkyl, acyl, amide, thioether, or disulfide) or any linker or spacer functioning as a homobifunctional or heterobifunctional linker including, but not limited to, such reactive groups as hydrazides, maleimidazoles, oxidizable diols, and succinimydyl groups. At most only one of $R_{12}$ and $R_{10}$ may be $NHR_k$.

The invention further includes nvel phosphoramidities having the formula:

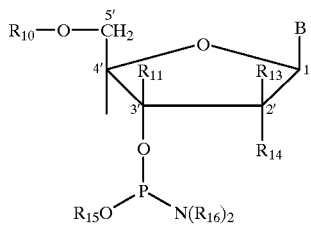

wherein B is any of the fluorescent nucleoside analogs described herein and $R_{10}$, $R_{11}$, $R_{12}$, $R_{13}$ are as defined for the set of glycosides, F, as above, and $R_{14}$ may be either H or OH. $R_{16}$=lower alkyl, preferably lower alkyl such as methyl or isopropyl, or heterocyclic, such as morpholino, pyrrolidono, or 2,2,6,6-tetramethylpyrrolidono; $R_{15}$= methyl, beta-cyanoethyl, p-nitrophenyl, o-chloronitrophenyl, or p-chlorophenyl. All other R groups are as before including those identifying spacer or linker arms of from 1 to 25 carbon atoms in length. Prior to the synthesis of the phosphoramidite at $R_{12}$ in order to (i) preserve any reactive substituents on the heterocycle which are important to its participation in Watson-Crick base pairing, and (ii) render the amidite compatible with the DNA or RNA chain assembly chemistry, the base moiety B in the phosphoramidite can be protected, which generally involves acylation or amidation of the exocyclic amino groups and includes, but is not limited to, acetyl, benzoyl, isobutryl, succcinyl, phthaloyl, or p-anisoyl; such amidine groups include, but are not limited to, dimethylformamidine, di-n-butylformamidine, or dimethylacetamidine; if B is substituted with other reactive groups such as carboxyl, hydroxyl, or mercapto, these are appropriately protected as well.

The present invention encompasses the synthesis of oligonucleotides on a solid phase support, wherein the oligomer is reacted with the protected fluorescent nucleoside analog phosphoramidites as illustrated in FIGS. 5 through 11 and derivatized as in the structure, above. Additionally, the present invention includes the novel fluorescent oligonucleotides having included in their sequences at least one fluorescent nucleoside analog derivatized as the phosphoramidite in the structure, above. Moreover, it is yet again another aspect of the present invention to provide fluorescent oligonucleotides made by the reactions of the aforementioned fluorescent analog 3'-O-phosphoramidites which are bound to, or have been bound by, a solid support.

(3) Sources and other preparations of the fluorescent structural analogs. Formycin A is isolated as the ribonucleotide from the culture broths of Nocardia interforma. The antibiotic is also isolated from culture broths of Streptomyces lavendulae and Streptomyces gummaensis, and is one of numerous microbial C-ribonucleoside analogs of the N-nucleosides commonly found in RNA from all sources. The other naturally occurring C-ribonucleosides which have been isolated from microorganisms (FIG. 5) include formycin B, oxoformycin B, pseudouridine, showdowmycin, pyrazomycin, and minimycin. Formycin A, formycin B, and oxoformycin B are C-nucleosides or pyrazolopyrimidine nucleosides of the class shown in FIG. 6 and are structural analogs of adenosine, inosine, and hypoxanthine, respectively; a pyrazopyrimidine structural analog of guanosine obtained from natural sources has not been reported in the literature but can be chemically synthesized from the 2-chloro-formycin B or its deoxy form. A thorough review of the biosynthesis of these compounds is available in Ochi et al. (1974) *J. Antibiotics xxiv*.:909–916. Synthesis of the $N_4$ and $N_6$ derivatives of the C-nucleotides are described in Lewis and Townsend ([1980] *J. Am. Chem. Soc.* 102:2817). Corresponding syntheses for the isomeric aminopyrazolo-[3,4d]-pyrimidines are in Wierchowski et al. (all others are commercially available in ribose, and several in deoxy and dideoxy forms, includingthe azanucleotidesand deaza nucleotides, or can be synthesized de novo, e.g., 7-deazaadenine (Gerster et al. [1967] *J. Med. Chem.* 10:326)). C-nucleoside analogs of the pyrazolo-s-triazineclass (e.g., pyrazolo [1,5a]-1,3,5-triazine) were prepared from amino pyrazole-C-nucleoside as originally described (Fox et al. [1976] *J. Heterocycl. Chem.* 13:175).

Production of the deoxy, dideoxy, and phosphorylated forms of the fluorescent ribonucleoside analogs. Chemical syntheses are available in the literature for the derivatizationas 2'-deoxy forms and 3'-deoxy forms of N-nucleoside, ethenonucleosides as well as the C-nucleosides (Robins et al. [1973] *Can. J. Chem.* 51:1313; Jain et al. [1973] *J. Org. Chem.* 38:3719; DeClerq et al. [1987] *J. Med. Chem.* 30:481). Similar procedures obtain for the deoxy forms of the azanucleotides,deazanucleotides and are found in the same and additional sources (e.g., Robins et al. [1977] *Can. J. Chem.* 55:1251; DeClerq et al., supra). Protocols and procedures for synthesis of the 3'-azido, 3'amino, 2',3'-unsaturated, and 2',3'-dideoxy analogs are as reported (Lin et al. [1987] *J. Med. Chem.* 30:440; Serafinowski, P. [1987] *Synthesis* 10:879). Protection or derivatization of the 2'-OH with silyl or FRET moieties can be done as by Peterson and Anderson ([1989] *Silicon Compounds: Register and Review*, Petrarch Systems, Inc., pp. 60–70).

Reported herein is the novel application of a cyclic protection procedure from the ribose to the deoxyribose conversion of C-nucleosides by which only the 2'-deoxy form of the analog is produced, and by means from which high yields can be obtained without the difficult purification necessary to separate the two isomers produced using the acetoxyisobutyryl halide procedures cited above.

For enzymatic syntheses, mono- and triphosphate forms of the nucleoside analogs can be prepared by enzymatic phosphorylation with, e.g., polynucleotide kinase using established procedures, or by chemical phosphorylation. In general, the 5'-monophosphates are prepared chemically by the $POCl_2$ (Smith and Khorana [1958] *J. Am. Chem. Soc.* 80:1141; Yoshikawa et al. [1967] *Tetrahedron Lett.* 5095). The corresponding triphosphates can be chemically synthesized according to the same authors or Michelson ([1964] *Biochim. Biophys. Acta* 91:1); or Hoard and Ott ([1965] *J. Am. Chem. Soc.* 87:1785). That is, the monophosphates are treated with carbodiimide (CDI) followed with tributylammonium pyrophosphate to give the triphosphorylated form. Where it is desired to phosphorylate analogs with exposed amino groups, such substituents can be thioacetylated by treatment with ethyl trifluorothioacetate according to the procedure of Thayer et al. ([1974] *Biochem. J.* 139:609).

B. Synthesis of Fluorescent Oligonucleotides

The present invention presents synthetic methods for the introduction of one or more of the fluorescent nucleoside analogs of the commonly occurring nucleotides into synthetic oligonucleotides.

(1) Use of fluorescent phosphoramidites. Fluorescent phosphoramidites can be synthesized from the ribose and deoxy-ribose monomers of the fluorescent nucleoside analogs. According to the present invention, fluorescent residues are introduced into chemically synthesized oligonucleotides by first synthesizing the protected 3'-O- phosphoramidite of a nucleoside analog, e.g., 2'-deoxyformycin A; the phosphoramidite is then substituted for the corresponding standard phosphoramidite, in this case deoxyadenosine-3'-O-phosphoramidite, and reacted with the oligonucleotide being synthesized on a solid support using standard phosphotriester chemical synthesis. The β-cyanoethyl derivatives may be selectively inserted at any desired position in a chemically synthesized oligonucleotide to produce oligomers of prescribed sequences of 60 or more bases in length and carrying any predetermined number of fluorescent bases.

For example, non-self-hybridizing oligonucleotides were synthesized which had the perfectly alternating sequences, $[AC]_x$ and $[FC]_x$, where x is the number of AC and FC dimer pairs and x had values of x=10, 15, 20, 25, 30, gave nearly identical values for both repetitive (>98%) and overall synthesis yields, and produced oligomers which differed only in that $[FC]_x$ was fluorescent, whereas $[AC]_x$ was not. Both oligomers hybridized specifically with complementary alternating oligomers of the sequence $[TG]_x$ but not with themselves or with noncomplementary sequences such as $[AG]_x$ and $[TC]_x$ as indicated by (i) ethidium bromide staining in agarose gels and (ii) the melting behavior of the hybrids. Equivalent values of the melt transition temperatures in 0.075 M NaCl for the $[FC]_x$:$[TG]_x$ and $[AC]_x$:$[TG]_x$ hybrids varied by less than 1° C. for a given value of x (length of oligonucleotide). Specifically, one aspect of the present invention involves the synthesis of 3'-O-phosphoramidites of the fluorescent nucleotides and of their fluorescent structural analogs, the use of amidites to synthesize highly fluorescent oligonucleotides having prescribed sequences and the uses of such oligonucleotides as amplification primers, fluorescent oligonucleotide "tags," and hybridization probes.

Figure 12:
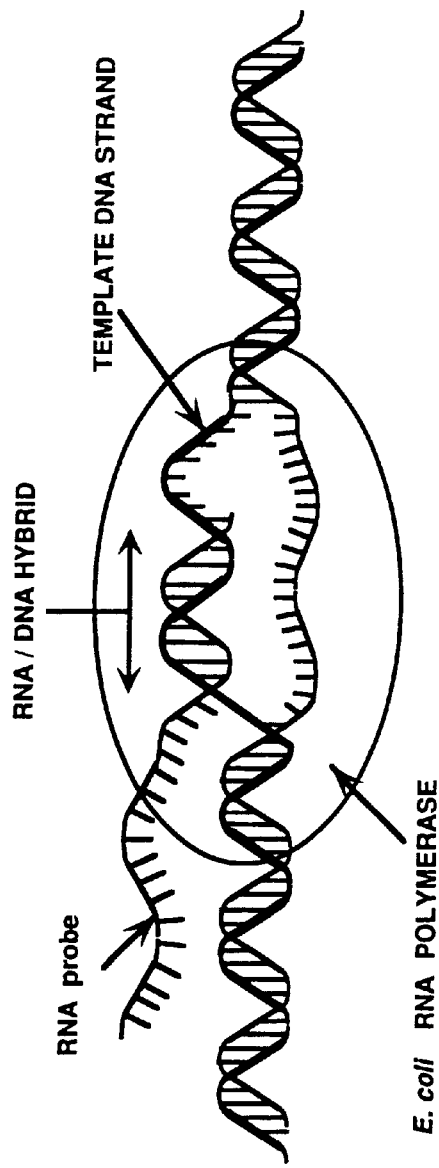
FIG. 12 is a diagram of symmetric RNA synthesis using FTP or ATP.
Figure 12:
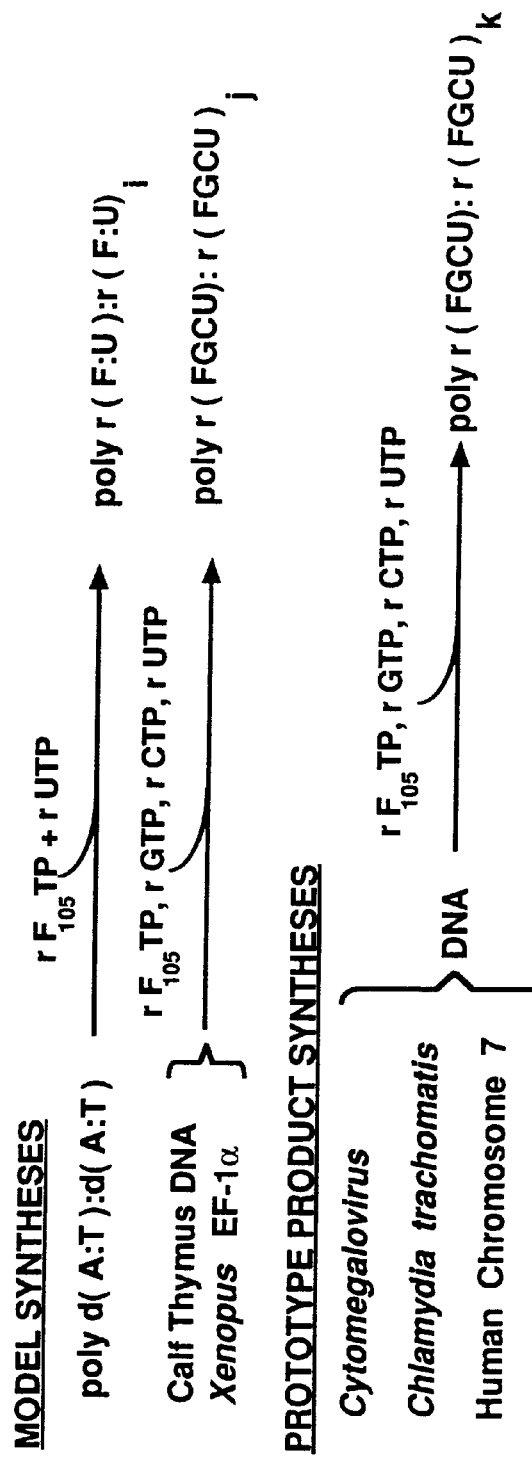
Figure 13:
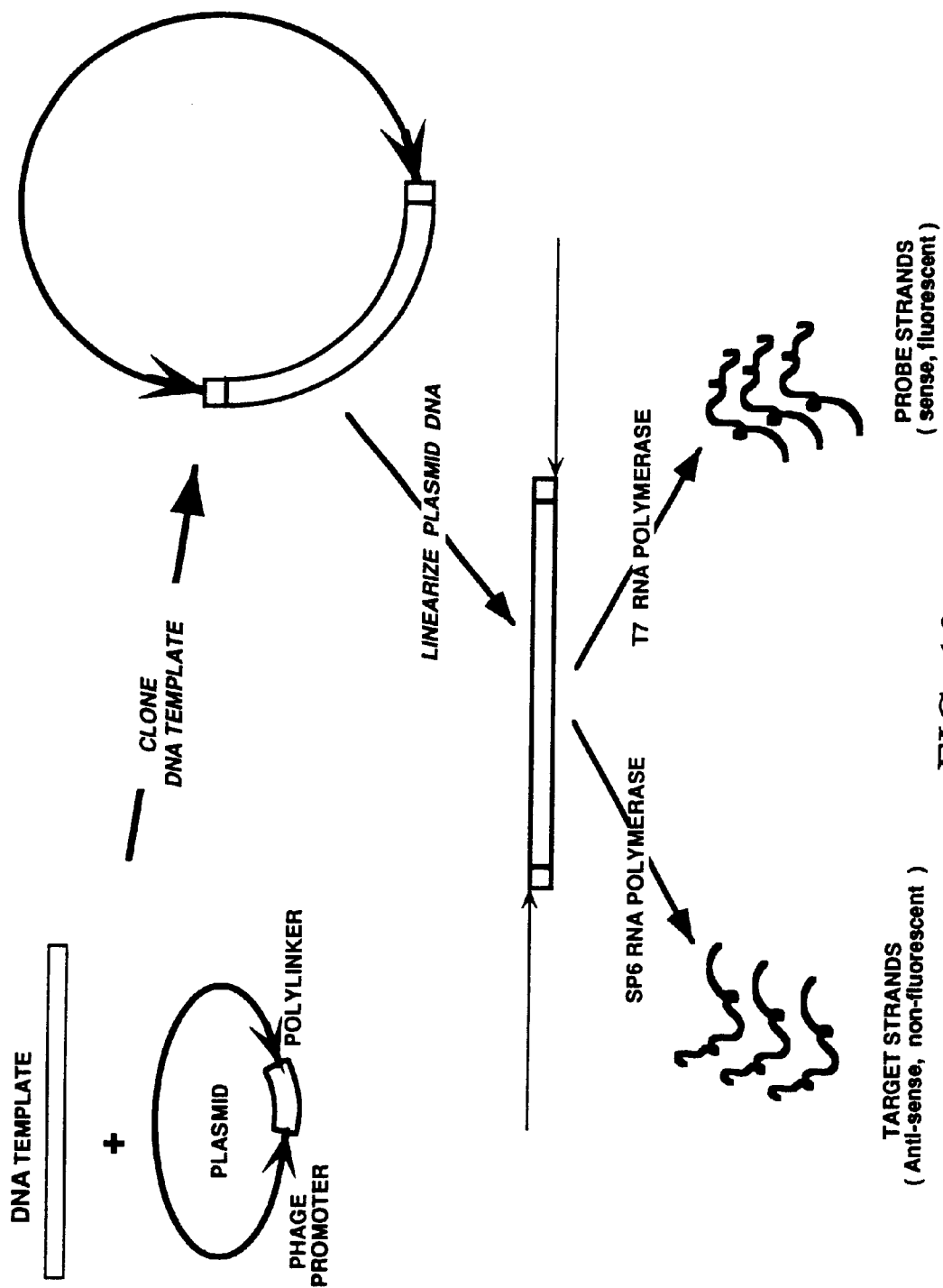
FIG. 13 is a diagram of promoter directed asymmetric RNA probe synthesis using viral promoters and viral RNA polymerases.

(2) Use of fluorescent polyribonucleotides and polydeoxyribonucleotides. Fluorescent polyribonucleotidesand polydeoxy-ribonucleotidesof prescribed sequences can be synthesized enzymatically using DNA templates from a variety of sources including those prepared by chemical synthesis, cloning techniques, or obtained from genomic DNA. Representative syntheses of RNA oligonucleotides using three such DNA templates, *E. coli* RNA polymerase, the rNTPs cytidine, uridine, and guanosine, together with the ribose triphosphate of either formycin A or adenosine, are illustrated in FIG. 12. A representative asymmetric synthesis of an RNA probe using a template bearing directional viral promoters, the viral RNA polymerases, the rNTPS cytidine, uridine, and guanosine together with the ribose triphosphate of either formycin A or adenosine, is illustrated in FIG. 13. Symmetric polydeoxyribonucleotides have been made by substituting 2'-deoxyformycin A-5'-triphosphate (FTP) for deoxyadenosine-triphosphate (dATP) in standard DNA polyerase syntheses and in DNA amplifications using thermostable DNA polymerase enzymes and the polymerase chain reaction; the corresponding asymmetric syntheses have been achieved using the same reagents and procedures but with the following modifications: (i) syntheses using such DNA polymerase as Klenow fragment or modified T7 DNA polymerase employed a template into which a primer site such as the M13 forward primer sequence was incorporated into one strand of a duplex at the beginning of the sequence that was to be used as the template, and the corresponding primer was used to initiate all syntheses; (ii) primers complementary to only one strand of a template were used in amplification as is commonly described as asymmetric PCR; or (iii) paired primers in which one of each pair of primers was coupled to a linker such as biotin were used in standard DNA amplifications such as PCR, but one strand was preferentially removed by subsequent isolation such as by use of an avidinylated column or magnetic beads. Comparable syntheses can be made by other substitutions, including, e.g, the fluorescent-nucleosides, 2-amino purine, and 2,6-amino purine (also substituted for adenosine-5'-triphosphate) and either of the fluorescent C-nucleoside triphospates of formycin B or 5-amino-formycin B (substituted for inosine triphosphate and guanosine-triphosphate,respectively) in either their ribose and deoxyribose forms.

C. Labeling of Fluorescent Polynucleotides

RNA and DNA can be enzymaticallylabeled by several methods including, but not limited to, (i) 5' DNA end-labeling using both the forward phosphorylation reaction (Richardson, C. C. [1965] *PNAS* 54:158) or the exchange kinase reaction (Van de Sande et al. [1973] *Biochemistry* 12:5050); (ii) mixed primer labeling by extending mixed sequence hexadeoxynucleotides annealed to restriction fragments (Feinberg, A., B. Vogelstein [1983] *Anal. Biochem.* 132:6; Feinberg, A., B. Vogelstein [1984] *Anal. Biochem.* 137:266); (iii) 3'DNA end-labeling using the enzyme, terminal deoxynucleotidyl transferase, to catalyze the repetitive addition (Okayama et al. [1987] *Methods Enzymol.* 154:3; Heidecker, G., J. Messing [1987] *Methods Enzymol.* 154:28) of mononucleotide units of the deoxytriphosphates, or single additions of deoxytriphosphates, of several of the fluorescent nucleoside analogs to the terminal 3'-hydroxyl of DNA initiators, including nonfluorescent probes of prescribed sequence, e.g., the *Chlamydia trachomatis* MOMP gene probe synthesized as described below; (iv) ligase labeling in which non-fluorescent "sticky-ended" or "nicked" RNA or DNA oligonucleotides are labeled by ligation with the appropriate fluorescent RNA or DNA oligomers (Pharmacia LKB [1989]*Analects* 17.2; Helfman, D. M. [1987] *Methods Enzymol.* 152:343); (v) nick translation, in which DNA polymerase is used to incorporate the triphosphates of the fluorescent analogs randomly in an existing DNA strand in a duplex (Meinkoth, J., G. M. Wahl [1987] *Methods Enzymol.* 152:91).

D. Characterization of Fluorescent Oligonucleotides of Prescribed Sequences

Hybridization, thermal melting, agarose gel characterization and fluorescence detection studies were used to characterize oligonucleotides of prescribed sequences. In some cases, the fluorescent oligonucleotides were complementary to known sequences of target DNA from clinically important pathogens or mutations, e.g. the MOMP gene sequence from *Chlamydia trachomatis*. In these studies, the templates used for enzymatic synthesis of the fluorescent oligonucleotideswere the cloned fragments also intended for use later as the target DNA in subsequent hybridization studies. Hybridization of the oligonucleotides with target DNA results in quenching of the fluorescence of the structural analogs in a fluorescent probe, which fluorescence is recovered upon denaturation of the hybrid, thereby proving that hybridization has occurred. The self-hybridization of the synthetic oligonucleotidepoly(rFrU), which is discussed at length, below, is representative of the results obtained in such experiments and is summarized in Table 1.

A preferred process according to the subject invention involves four basic steps. Initially the fluorescent structural analogs are chemically or biologically synthesized and, where appropriate, further derivatized as required to synthesize a fluorescent oligonucleotide probe. Second, a DNA or RNA probe molecule complementary to a nucleic acid sample of interest is constructed to have fluorescent nucleoside analogs which can be (i) distributed randomly or at specific locations throughout its length, or (ii) placed as terminal labels as described below. Third, the nucleic acid sample is then separated from unreacted monomers and can then be characterized directly, used as an extrinsic, non-specific label for tagging specific hybridization probes, or used directly as a hybridization probe. In the latter case, hybridization may take place on a solid phase to which either the target DNA/RNA or the fluorescent probe has been immobilized such as in Southern blot transfers, or "Dot-Blot" techniques, or it may occur in solution (herein, "solution hybridization"), after which probe/target hybrids are separated from unhybridizedprobes by simply washing or filtration. Finally, the fluorescence of the oligonucleotides hybridized to the target DNA/RNA is detected and quantified.

E. Construction of Fluorescent Probe Molecules

In accordance with the present invention, a preselected fluorescent nucleoside analog or mixture of fluorescent analogs is substituted specifically for one or more of the non-fluorescent commonly occurring nucleosides and is then incorporated into DNA or RNA oligonucleotides to create prescribed sequences. The prescribed sequences may be chosen to be equivalent in their Watson-Crick base pairing to a nucleotide sequence constructed from normally occurring nucleotides and complementary to a given target DNA or RNA sequence; such fluorescent probes are said to be analogous to the complementary sequence of the target DNA or RNA. The fluorescent probe may be synthesized by either enzymatic or chemical synthesis for subsequent applications such as (i) hybridization probes, (ii) amplimers for direct detection of amplifiable gene sequences complementary to a given set of primers, or (iii) as non-specific "universal" labels which can be attached to specific hybridization probes by, e.g., ligation.

Fluorescent nucleoside analogs of the commonly occurring ribo-, deoxy-, or dideoxyribonucleotides can be incorporated into nucleic acid polymers using one of several otherwise conventional enzymatic and chemical techniques including, but not limited to, those described here.

(1) Enzymatic syntheses. Enzymatic syntheses include:

(a) the use of the enzyme DNase I to introduce small "nicks" into one strand of a double stranded DNA duplex. The holoenzyme form of *E. coli* DNA polymerase I can then be used to extend and repair these nicks using a mixture of fluorescent nucleotide analog triphosphates,e.g, deoxyformycin-5'-triphosphate (FTP), with commonly occurring deoxynucleotide triphosphates in the reaction mixture. This method introduces a large number of fluorophores randomly throughout the DNA polymer, including both strands of the double helix. In practice, the commonly occurring nucleotide, in this case dAdenosine-5'-triphosphate (dATP), can be eliminated entirely, and the dFTP substituted in its place, without significant loss of synthetic yield, loss of hybridization specificity, or strength of duplex formation as measured by the values of the DNA melting temperature;

(b) the use of a variety of enzymes, including the Klenow fragment of DNA polymerase I and the T4 DNA polymerase, to fill in overhanging single stranded regions of DNA produced by the prior actions of restriction enzymes. This method concentrates the fluorescent analogs at the end of each DNA strand. Similarly, fluorescent DNA oligonucleotides complementary to a specific DNA template can be synthesized (i) by using DNA fragments and *E. coli* DNA polymerase, or (ii) by constructing a recombinant plasmid containing the primer site for a specific primer such as the M13 forward primer immediately 5' to the desired DNA template sequence. The DNA polymerase will synthesize a complementary DNA molecule using deoxyribonucleotides or other deoxyanalogs including, e.g., dFTP as a substitute for dATP, present in the reaction mixture;

(c) an incorporation method which also produces a terminal concentration of fluorescent analogs involves the use of the "tailing" enzyme, terminal deoxynucleotide transferase, to add a homopolymer or "tail" of fluorescent deoxy analogs to the 3' end of DNA oligomers. In practice, the yields obtained in the synthesis of homopolymers when substituting fluorescent analogs for the commonly occurring nucleosides is significantly less than the yield obtained in the synthesis of heteropolymers. Alternatively, a single fluorescent nucleoside analog may be added to the 3' OH of any oligomer using the same enzyme but the dideoxy form of a fluorescent analog or a 2'-protected fluorescent analog, including the FRET protected analogs, in exactly the same manner in which, e.g., dideoxy ATP (cordecypin), is used. A third alternative method of endlabeling hybridization probes utilizes the action of DNA ligase or RNA ligase, by which non-specific double or single stranded fluorescent oligonucleotides can be covalently coupled to either the 3' or 5' end of specific hybridization probes; the fluorescent oligonucleotidesused in this fashion do not necessarilyparticipate in the Watson-Crickbase pairing which determines specificity of a probe, but may act solely as a generic or universal fluorescent "tag." With each of the foregoing methods, the DNA probes are double stranded and must be denatured to single stranded form using either heat or alkali treatment prior to their use for hybridization;

(d) an incorporationmethod, which can also be used as a standard method of production of fluorescent probes having a prescribed length and sequence, using standard methods of DNA amplification or replication and one of several available DNA polymerases, including but not limited to the thermostable DNA polymerases, e.g. Taq polymerase, modified T7 DNA polymerase, Klenow fragment, and T4 DNA polymerase, but substitutes one of the fluorescent deoxyribonucleotide analogs, e.g, 2'-deoxyformycin A-5-triphosphate or 5-amino-deoxyformycin B-5'-triphosphate for ATP and GTP, respectively, in the mix of nucleotide triphosphates. The fluorescent oligonucleotides are equivalent in yield and length to the non-fluorescent oligomer made with the commonly occurring nucleotides and hybridize to target template DNA and display the same thermal stability and capacity to stain with ethidium bromide as do the nonfluorescent controls once the hybrid duplex has formed. In such amplifications, the production of fluorescent oligonucleotides can be taken directly as evidence of the presence of a particular sequence, or the identity can be further established by (i) hybridization with a defined complementary probe, and (ii) sequencing to establish the analogous sequence; and (e) the use of fluorescent RNA oligonucleotides complementary to a specific DNA template which can be synthesized (i) symmetrically, by using DNA fragments and, e.g., *E. coli* RNA polymerase as illustrated in FIG. 12, or (ii) asymmetrically, as shown in FIG. 13, by constructing a recombinant plasmid containing the promoter for a specific DNA dependent RNA polymerase immediately 5' to the desired DNA sequence which is used as a template, e.g., a DNA template bearing a T7 RNA polymerase promoter immediately 5' to the fragment of a cloned Chlamydia MOMP gene fragment which has the sequence which will be used as the target for hybridization with the probe. For most applications, asymmetric synthesis is the preferred method, and the corresponding DNA-dependent RNA polymerase will synthesize an RNA molecule using ribonucleotides, e.g., FTP as a substitute for ATP and UTP instead of TTP, which is the analogous complement to one, and only one, of the two strands of the template. The resulting single stranded probes can be used directly in a subsequent hybridization reaction without a denaturing step.

(2) Chemical syntheses. The protected fluorescent deoxynucleoside analog-3'-O-phosphoramidites, typically those in which $R_{10}$=dimethoxytrityl, $R_{16}$=isopropyl, and $R_{15}$=methyl or beta-cyanoethyl, are coupled to the 5'-OH of a growing oligonucleotide attached to a solid support using standard phosphoramidite DNA synthesis techniques (see Atkinson, T., and M. Smith [1984] In *Oligonucleotide Synthesis: A Practical Approach*, M. J. Gait, ed., IRL Press, Oxford, pp. 35–82). Solid support-bound oligonucleotide, which has already been acid washed to deprotect the 5'-OH group, is reacted with 5'-trityl protected deoxynucleoside analog-3'-O-phosphoramidite in anhydrous acetonitrile in the presence of tetrazole under argon, washing away excess reagents, and then oxidizing the phosphite product to the desired phosphate with a solution of iodine in aqueous THF, and washing with anhydrous acetonitrile. After acid washing to deprotect the new 5' terminus, the cycle can be repeated as many times as necessary to achieve the desired length and sequence; additional nucleotides which are added may be the commonly occurring nucleotides or they may be additional fluorescent nucleoside analogs. Accordingly, one or more fluorophores may be incorporated within a given probe up to and including complete substitution of, e.g., all of the A residues in a desired sequence with formycin residues. The couplings can be performed manually in a minireactor vial, utilizing a 10 minute coupling time, or on a Pharmacia LKB Gene Assembler or similar instrument utilizing the programmed synthesis protocols. The fluorescent oligonucleotide is then isolated by cleaving the DNA from the porous glass support by incubation at 55° C. overnight in $NH_4OH$:ethanol (3:1). The fluorescent DNA containing ammonium hydroxide solution can then be quickly dried in a Speed-Vac and then separated from failure sequences of a QEAE-HPLC column using a shallow salt and pH gradient. Yields for the nucleoside analog phosphoramidites are comparable to those obtained with standard amidites based on repetitive yield calculated from trityl cation release at the deprotection step.

To provide specific illustrations of how to construct and use probe molecules containing a fluorescent nucleoside analog, following are examples which illustrate procedures, including the best mode, for practicing the invention. These examples should not be construed as limiting. All percentages are by weight and all solvent mixture proportions are by volume unless otherwise noted.

EXAMPLE 1

Figure 16:
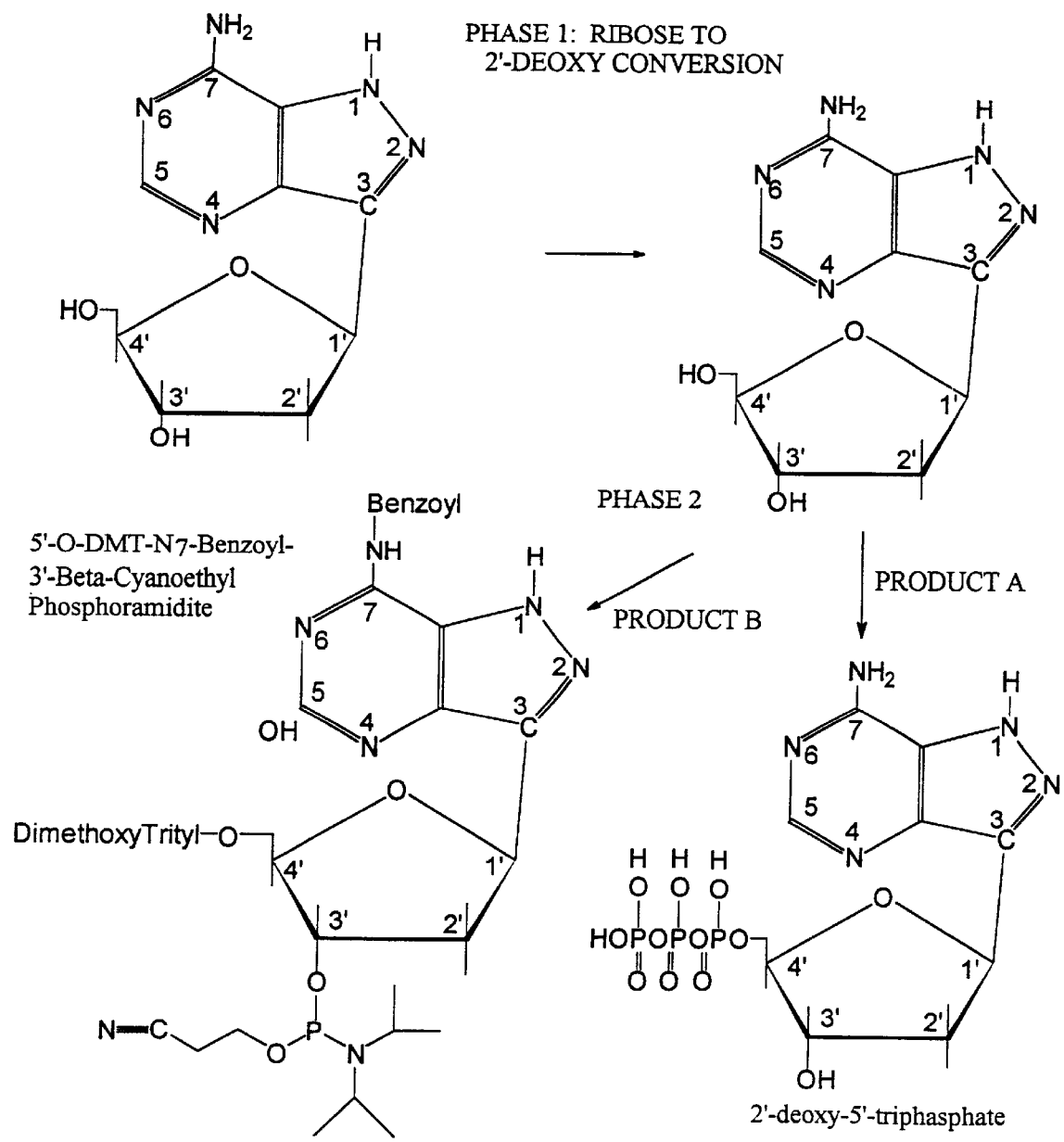
FIG. 16 is a diagram showing the conversion of the ribonucloetide analog, formycin A, to its 2'-deoxy triphosphate or phosphoramidite forms.

Chemical Conversion of Formycin A to 2'-Deoxy Formycin A and Preparation of the 5'-Triphosphate and 3'-O-(2-cyanoethyl)-N'N'-Diisopropyl Phorphoramidite FIG. 16 depicts the invention scheme used to make the 2'-deoxy-5'-triphosphate or 2'-deoxy-3'-O-phosphoramidite of formycin A. While the first phase has been previously accomplished by the reaction with α-acetoxyisobutyryl halides as described by De Clerq et al. ([1987] *J. Med. Chem.* 30:481), the procedure produces both the 3' and 2' deoxy forms which are difficult to separate and are produced in low yield. The present invention employs a 3',5'-disila protection which has previously been applied successfully in the conversion of adenosine to 2'-deoxyadenosine([1981] *J. Am. Chem. Soc.* 103:932). The method appears to be generally applicable to the corresponding conversion of many fluorescent nucleoside analogs.

(1) 7-amino-3-[3'5'-O-(1,1,3,3-tetraisopropyl-1,3-disiloxane-dilyl)-β-D-ribofuranosyl pyrazolo [4,3d] pyrimidine. 1,3-dichloro-1,1,3,3-tetraisopropyl-1,3-disiloxane (0.9 g, 2.85 mMol) was added to a suspension of formycin A which had been exhaustively dehydrated (0.66 g, 2.5 mMol) in anhydrous pyridine and the reaction was stirred at room temperature for 24 hours. The solvent was removed under vacuum at T=40° C. and the product extracted between ethyl acetate and water. The ethyl acetate phase was washed, in seriatim, with (i) cold 1 N HCl, $H_2O$, aqueous $NaHCO_3$ (saturated) and aqueous NaCl (saturated) followed by evaporation to a gum. Following flash chromatography on silica gel and stepwise elution with (i) 2.5% methanol-chloroform, and (ii) 5% methanol-chloroform, the product, which ran as a single spot on silica TLC ($R_f$=0.80 in 20% methanol-chloroform), was shown to be the 3',5' cyclic protected product by proton NMR and elemental analysis.

(II) 7-amino-3-[3',5'-O-(1,1,3,3-tetraisopropyl-1,3-disiloxane-dilyl)-2'-(phenoxythiocarbonyl)-β-D-ribofuranosyl] pyrazolo [4,3d] pyrimidine. 480 mg of disila protected formycin A (0.93 mMol) was dissolved with DMAP (0.9 g, 7.6 mMol) in anhydrous MeCN. Following dropwise addition of 200 mL of phenoxythiocarbonyl chloride through a dry syringe mounted in a ground glass joint, the reactants were stirred for 24 hours at room temperature, after which solvent was removed under vacuum and the product again partitioned between ethyl acetate and water. The ethyl acetate phase was washed as above, the solvent evaporated, and the residue separated on flash chromatography and eluted with chloroform-MeCN (50/50). Pooled fractions of the desired product were identified by proton NMR and elemental analysis and subjected to a second round of production, as below.

(III) 7-amino-3-(2'-deoxy-β-D-ribofuranosyl)pyrazolo[4,3d]pyrimidine(2'-deoxy formycin A). 240 mg of the product obtained from the procedure described in II, above, were added to 12.5 mg $(NH_4)_2SO_4$ in a gross excess of hexamethyldisilazane. The reaction mixture was refluxed at >60° C. overnight. After evaporation under vacuum, the crude trisylyl derivative was redissolved in toluene and reacted with azobisisobutyronitrile and tributyl tin hydride by heating under $N_2$ overnight to attain complete reduction. The product was deprotected in TBAF in THF at 80° C. overnight and, after evaporation, fractionated between ethyl acetate and water. The water layer was concentrated and applied to a Dowex 50W-X8 column equilibrated in water and then eluted with 15% $NH_4OH$. The principal product ($R_f$=0.3 in 20% methanol-chloroform)was shown to be identical to the purified 2'-deoxy formycin A which had been prepared using the method of De Clerq et al., supra and by proton NMR and elemental analysis.

(IV) 7-amino-3-(2'-deoxy-β-D-ribofuranosyl) pyrazolo [4,3d] pyrimidine-5'-triphosphate (2'-deoxyformycin A-5'-triphosphate). 28 mg (0.11 mMol) of 2'-deoxyformycin A was added to a glass stoppered test tube and mixed with 0.2 mL of reagent grade acetone and 0.1 ml of phosphorous oxychloride. The heterogeneous reaction mixture was stored at 4° C. for 24 hours, during which time the solution turned deep yellow. After cooling and addition of 3 ml cold acetone, 6 mMol of concentrated NH$_4$OH was added rapidly while mixing. After evaporation of the acetone, and reduction of the pH to less than 2, the mixture was refluxed for 1.5 hours, then diluted and applied directly to Dowex 1-formate, from which 2'-deoxyformycin A-MP was eluted with 0.75 M formic acid. 2'-deoxyformycin A-MP was converted to the triphosphate by the method of Yoshikawa et al. ([1967] *Tetrahedron Lett.* 5095).

(V) 7-amino-3-(2'-DEOXY-β-D-ribofuranosyl) pyrazolo [4,3d] pyrimidine-3'-O-phosphoramidite (2'-doexyformycin A-3'-O-phosphoramidite). 2-deoxyformycin A was treated to attain 5'-O- protection with DMT and benzoylation of the 7-amino group by standard procedures. To 0.3 mMol of the product and 25 mg of diisopropylammonium tetrazolide in 1.5 mL of CH$_2$Cl$_2$ was added a solution containing 0.33 mMol of O-cyanoethyl-N,N,N',N'-tetraisopropylphosphorodiamidite. The mixture was mixed for 4 hours and partitioned between CH$_2$Cl$_2$ and chilled in saturated NaHCO$_3$ solution. The CH$_2$Cl$_2$ layer was washed with saturated NaCl solution, dried (Na$_2$SO$_4$), filtered, and concentrated. Purification by filtration through a 2" plug of basic alumina in a 25 mm column, eluting with 9:1 CHCl$_2$/ET$_3$N, provided the phosphoramidite which could be dried to a foam. Identity of the product was verified by proton NMR, elemental analysis, fluorescence of the heterocycle, and use in oligonucleotide synthesis.

EXAMPLE 2
Complete Enzymatic Substitution of FTP or 2'dFTP for ATP or dATP in RNA or DNA Probes A. Symmetric synthesis of ribose oligomers. RNA oligonucleotides were synthesized from three DNA templates (FIG. 12) using (i) FTP (F$_{105}$) as a substitute for ATP, and (ii) a purified *E. coli* RNA polymerase as originally described by Ward et al. ([1969] *J. Biol. Chem.* 12:3242), except that synthesis was allowed to run for three hours at 37° C. before the reaction was stopped; FTP effectively replaced ATP but not any of the other three normal nucleotides CTP, UTP, or GTP.

Figure 19:
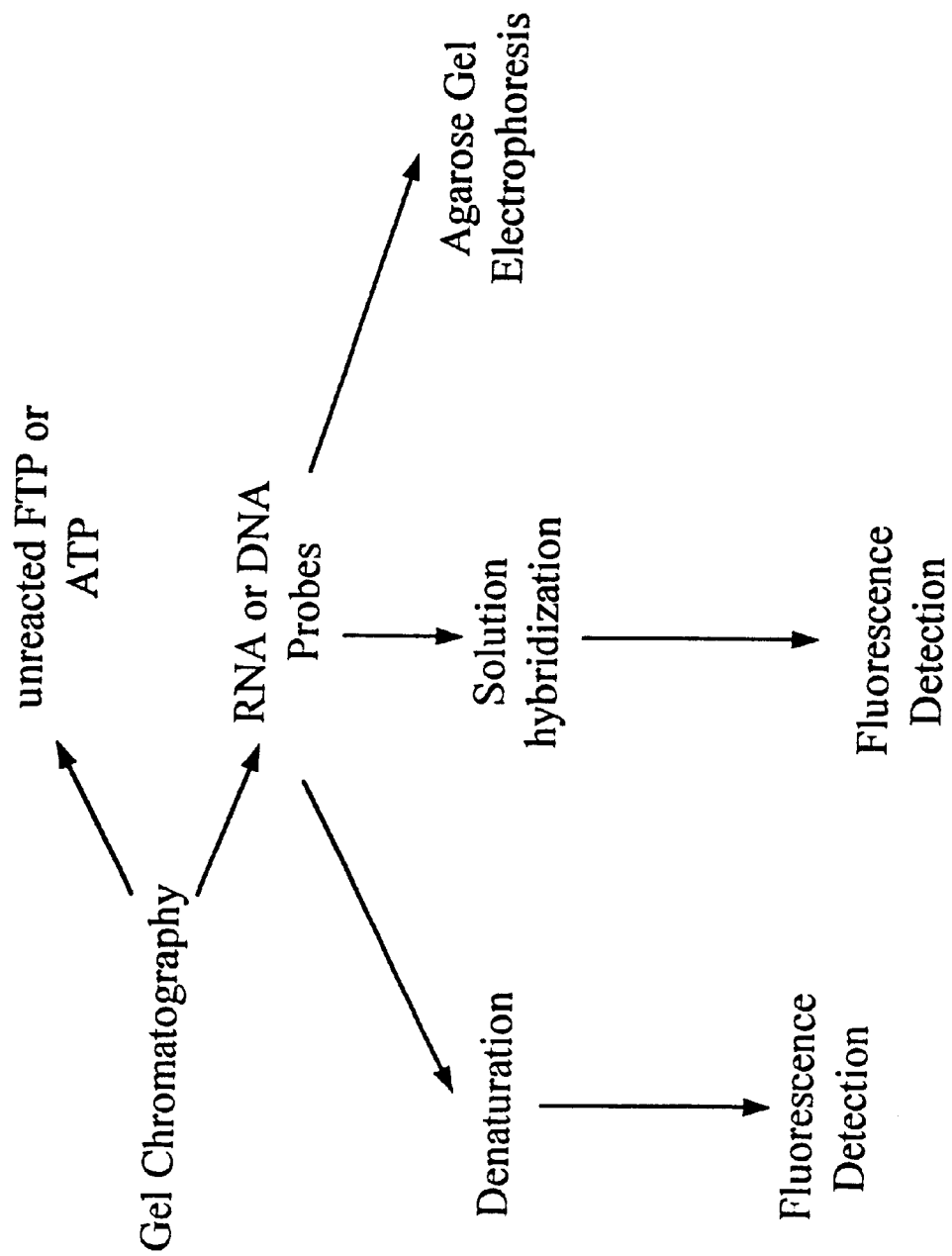
FIG. 19 shows a flow chart diagramming the separation scheme used to separate reaction products from unreacted reagents following the enzymatic substitution reaction of FTP for ATP in RNA probes.

At the end of the synthesis, reaction products were separated from unreacted reagents by separation at 4° C. on Sephadex G-50 in normal saline at pH 7. The scheme for separation of reaction products from unreacted agents is shown as a flow chart in FIG. 19.

In the reaction, FTP is an effective substrate for RNA polymerase with both native and denatured DNA as well as with synthetic deoxynucleotide polymer templates. In samples containing CTP, UTP, GTP, RNA polymerase, one of the DNA templates, and either FTP or ATP, a high molecular weight product eluted from either sample in the void volume while the amount of monomeric NTP in the retained fraction from either sample was correspondingly reduced by >70%. No high molecular weight fraction other than the small amount of template eluted from enzyme-free controls and unreacted rNTPs were undiminished; similarly, template-free controls contained only unreacted rNTPs which co-eluted in the retained volume with standard ribonucleotide triphosphates. Similar results were obtained with a variety of DNA templates from natural and synthetic sources, including the alternating copolymers poly d(AC), poly (AG), and poly (ACGT). Moreover, comparable yields of high molecular weight oligomer were obtained from syntheses in which (i) the N-nucleoside analogs 2,6-diamino-adenosine-5'-triphosphate or 2-diamino-adenosine-5'-triphosphate were substituted for ATP in the reaction mix, or (ii) the C-nucleosides formycin B-5'-triphosphate (F$_b$TP) or -amino-formycin B-5'-triphosphate (aF$_b$TP) were substituted for GTP in the reaction mix and using poly (TG) or poly (GC) as the DNA template. No matter what the template, yields obtained by substituting several of the deaza- and aza-nucleoside analogs for ATP or GTP were dramatically lower.

Figure 14:
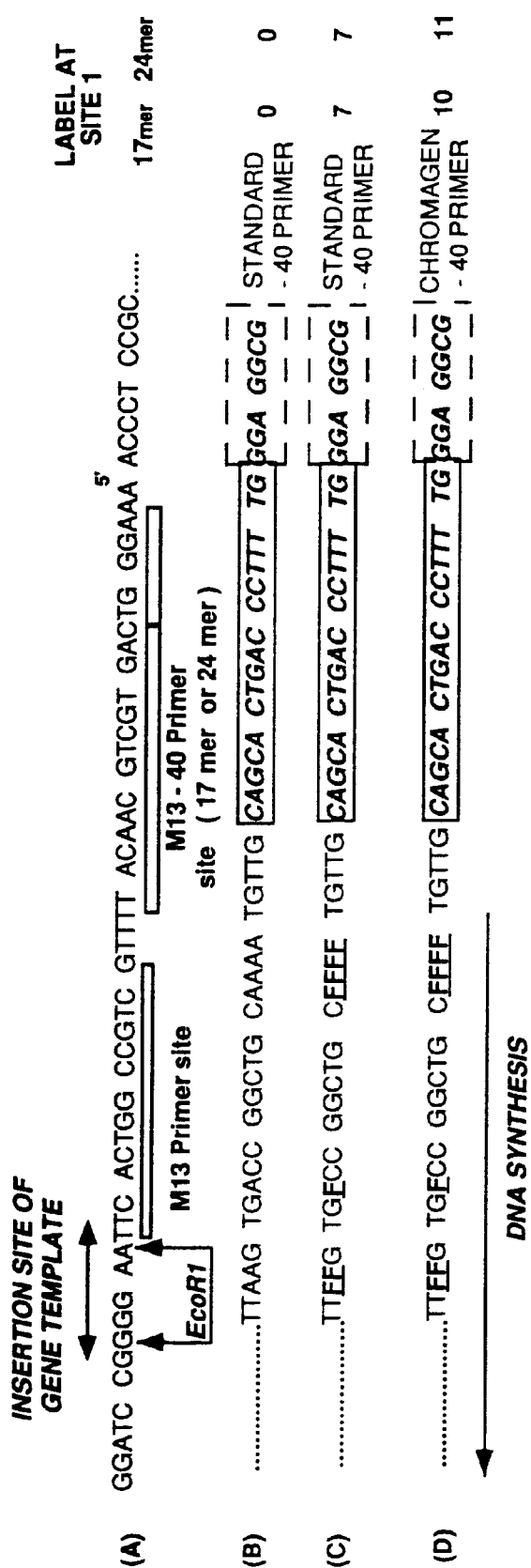
FIG. 14 is a diagram showing an example of the method for one-step labeling of ssDNA inserted at the EcoRI site of pUC/M13 plasmid vectors and using $dF_{105}$.
Figure 15:
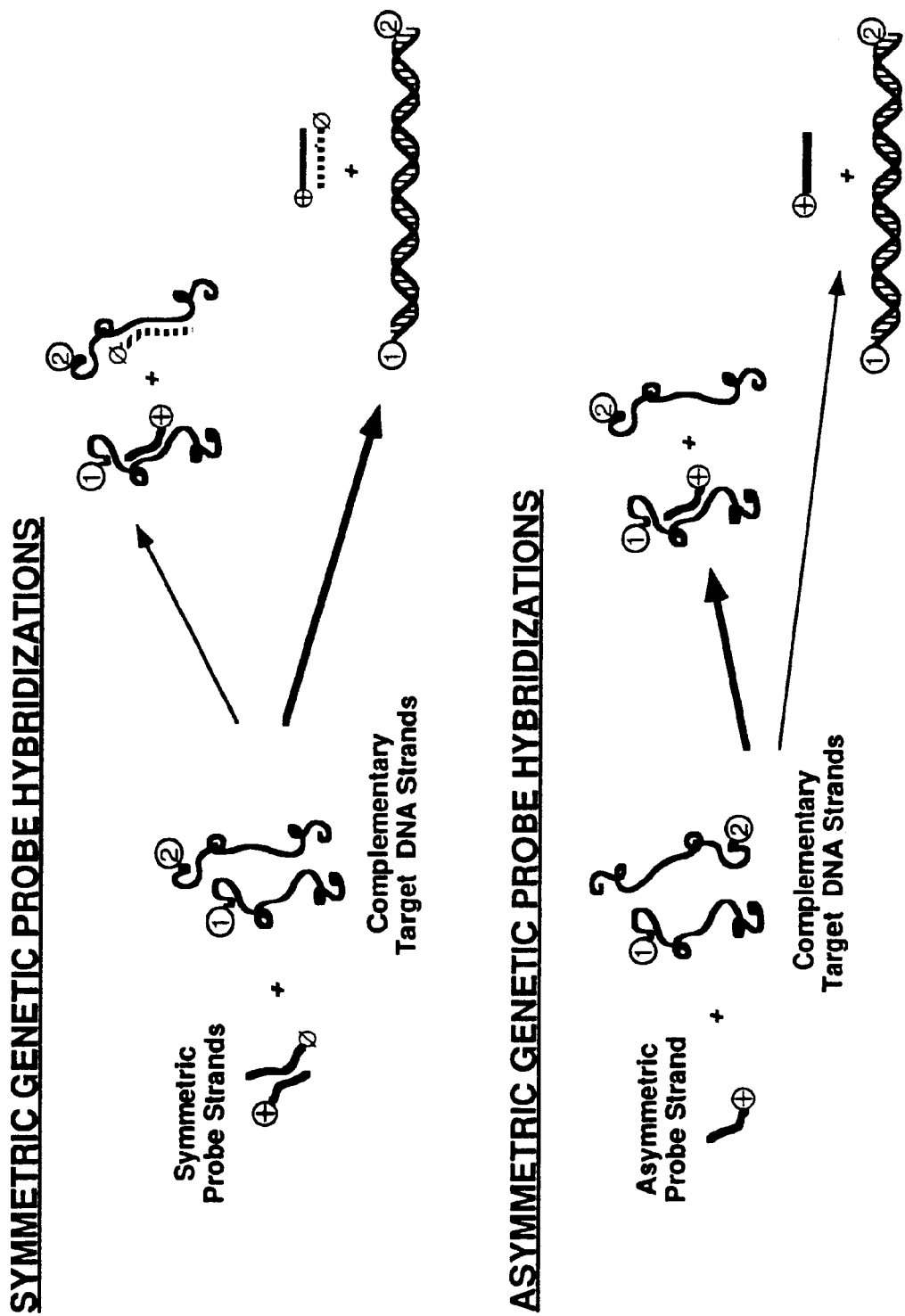
FIG. 15 is a diagram showing the necessity of using asymmetric DNA or RNA probes for rapid and quantitative hybridization of the probe to target DNA. As shown, asymmetric probes provide significant increases in hybridization efficiencies when compared with symmetric probes.

B. Asymmetric synthesis of RNA or DNA probes. In vitro, DNA dependent, RNA polymerase transcription systems for the synthesis of RNAs for use as substrates and hybridization probes are a fairly common tool of molecular biology. They are uniquely applied here to the development of autofluorescentprobes and their production. The method developed is general and applies to any of the phage polymerase systems, including SP6, T7, and T3. In the present case, the invention employs a pair of promoters which are separately positioned on alternate strands of a duplex plasmid and at opposite ends of a polylinker as shown in FIG. 13. The vectors are used to (i) attach promoters capable of effecting asymmetric synthesis through use of a viral polymerase which recognizes one of the promoters, and (ii) replicate multiple copies of a template for use in asymmetric production of a fluorescent probe or of a nonfluorescent copy of the probe target. A copy of the DNA target sequence is inserted into the polylinker in its duplex form and at a restriction site adjacent to one of the promoters. Replication of the plasmid in competent cells provides large amounts of the template for transcription. Two separate but parallel methods have been developed for the asymmetric synthesis of DNA probes. In the first case, ssDNA probes are synthesized from templates which have primer binding site attached at the 5' end of one template strand as shown in FIG. 14. In such syntheses, the primer may be non-fluorescent or may be synthesized using fluorescent analog phosphoramidites as shown at the right of the Figure. A variation on this is asymmetric amplification and separation in which both strands of a template may be replicated by amplification as fluorescent oligomers, but using a pair of primers in which one, and only one, bears a transient affinity linker such as biotin which may subsequently be used to separate the denatured sense and anti-sense strands.

For both RNA and DNA probes, it has proven practical to establish a reference template, probe sequence, and target sequence against which all transcriptions and probe detection sensitivities are calibrated. The alpha chain of Xenopus translation elongation factor (Xef-1α) serves that purpose and asymmetric RNA probe synthesis is used here as representative of all RNA and DNA synthesis. The Xef-1α mRNA is a major transcription product of the Xenopus embryo which comprises a large percentage of the non-mitochondrial mRNA transcripts that appear immediately after the midblastula transition. The gene for the Xef-1α was isolated and EcoRI linker sites added at the ends of the clone during construction of the cDNA library. The 1705 nucleotide fragment was inserted into a pSP72 plasmid bearing a T7 promoter on one strand and an SP6 promoter on the complement. Following plasmid replication and template linearization, transcription with T7 RNA polymerase, the rNTPs cytidine, uridine, and guanosine, together with the ribose triphosphate of either formycin A or adenosine, produced 1749-base-long oligomers containing 489 F or A residues, respectively. Transcripts less than full length were never observed and, in each case, the analogous and control oligomers were produced in comparable quantities and were generally indistinguishable in physical behavior save that the analogous sequence was permanently fluorescent.

There are two unique features of this novel manufacturing system. (1) Synthesis of the antisense strand, e.g., using SP6 and the commonly occurring nonfluorescent rNTPs provides standardized target sequences in high yield. In the corresponding asymmetric synthesis of DNA probes, distinct primer sites on complementary template strands can be used to achieve the same objective. (2) A mixture of plasmids containing several different plasmids can be used to create a "cocktail" of linearized templates from which the corresponding "cocktail" of probes (see Example 7, below), which can bind to multiple sites on a genomic sequence, can be concurrently transcribed.

EXAMPLE 3

The Fluorescence of Nucleoside Analog RNA Probes and Proof of Their Hybridization in Solution The effective utilization of FTP in the poly d(AT) directed synthesis in Example 1 produced a polymer approximately 300–500 bases in length which, when hydrolyzed and/or sequenced, proved to be a perfectly alternating replicate of the DNA template, but with the sequence: poly (FU). As predicted from this sequence, the product could be annealed to like chains by a single thermal cycle, thereby creating the putative product poly (FU):poly (FU); unlike the comparably treated poly (FC), which showed no evidence of self-hybridization as expected, the annealed hybrids of poly (FU):poly (FU) stained with ethidium bromide in agarose gels and gave a sharp thermal transition in both absorbance and fluorescence, proving that the probes could hybridize both effectively and specifically. The absorbance and emission spectra of the purified poly (FU), poly (FC), poly (FG), poly (UFb), poly (CaF$_b$), and poly (FCGU) differ from those of purified poly (AU), poly (AC), poly (AG), poly (TG), and poly (ACGT) controls in four respects: (i) the far UV absorbance maximum is shifted slightly for the analog-containing products, to 265 nm as compared to 260 nm for the controls; (ii) there is a significant, highly structured absorbance (3 peaks at room temperature) between 290 nm and 320 nm with negligible absorbance at 340 nm; (iii) an excitation maximum appears at 303 nm; and (iv) there is a broad emission band extending into the visible wavelengths with a peak at 405 nm (Stokes shift=102 nm). It is an important property that the fluorescence is fully quenched in, e.g., the poly (FU):poly (FU) hybrid, and cannot be detected until the strands are denatured by raising the pH of the solution to values >pH 10. Once denatured, the fluorescence of the oligomer is fully integratable, with relative fluorescence intensity >40% of peak intensity over the range 360 nm to 460 nm.

TABLE 1

Properties of hybrid formation by poly (AU) and poly (FU)

| RNA:RNA HYBRID | DENATURED HYBRID WAVELENGTH MAXIMA | | | INTACT HYBRID | | |
| --- | --- | --- | --- | --- | --- | --- |
| | ABSORBANCE | EXCITATION | EMISSION | LENGTH (BASE PAIRS) | ETHIDIUM BROMIDE STAINING | MELT TEMP |
| r[AU]:r[AU] | 260 nm | — | — | 150–300 | yes | 32° C. |
| r[FU]:r[FU] | 266 nm | 303 nm | 405 nm | 150–300 | yes | 33° C. |

EXAMPLE 4

Hybridization of Fluorescent Probes to Target RNAs and Target DNAs: Uses of Linkers to Allow Solid Phase Detection The synthetic template poly (TG) was used to produce the complementary RNA probes poly (AC) and poly (FC), neither of which is self complementary and in which hybrids could not be annealed or detected; of the two only the poly (FC) was fluorescent. In a parallel experiment, a poly (AC) template was amplified using the biotinylated synthetic 22-mer primers, $5°$BIOTIN-(TG)$_{11}$$^{3'}$, together with standard polymerase chain reaction (PCR) methods to produce the DNA amplimers having the sequence, $5°$BIOTIN-poly (TG) $^{3'}$, then separated from the unreacted primers by gel sizing and/or QEAE ion exchange chromatography, after which the polymers were radioactively labeled using $^{32}$P-ATP and the enzyme polynucleotide kinase. When mixed separately, but in equimolar amounts, with the biotinylated amplimers, $5°$BIOTIN-poly (TG)$^{3'}$, both of the RNA probes, poly (AC) and poly (FC), formed hybrids which could be characterized by (i) ethidium bromide staining, and (ii) melting behavior; as expected, the fluorescence of the poly (FC) probe was quenched by hybridization. The hybrids could then be adsorbed via the $^{5'}$BIOTIN moiety to avidinylated beads, washed to remove unhybridized poly (FC), and equal aliquots assayed for radioactivity and fluorescence. Prior to denaturation of the washed sample, detectable fluorescence in the solution was negligible; when denatured in high pH buffer, the amount of poly (FC) which had been hybridized, when estimated from the fluorescence of standardized dilutions of the probe, was within 1% of the amount of the target DNA, $5°$BIOTIN-poly (TG)$^{3'}$, as measured by the amount of radioactive label in the sample as compared to standardized dilutions.

EXAMPLE 5

Hybridization of Fluorescent Probes Synthesized from Nucleoside Analog-3'-O-Phosphoramidites to Target DNAs In a validation of the use of the phosphoramidites of the fluorescent nucleoside analogs, n-mers which varied in length in multiples of 5 bases from 25-mers to 60-mers, and having the sequence (AC)$_x$ or (FC)$_x$, where x=12.5, 15, 17.5, 20, 22.5, 25, 27.5, or 30, were synthesized in parallel using either dAdenosine-3'-O-phosphoramidite or dF-3'-O- phosphoramidite together with dC-3'-O-phosphoramidite in a Pharmacia LKB Gene Assembler. After cleavage from the solid phase and purification of QEAE-Sepharose, the fluorescent oligomers $(FC)_x$ of defined length could be hybridized to the radiolabeled amplimers of poly (TG), from Examples 2 and 3, above, as assessed by DNA melting behavior, ethidium bromide staining, and the reappearance if quenched fluorescence following denaturation of the hybrid.

EXAMPLE 6

Assay for *Chlamydia trachomatis* Using an FTP Substituted RNA Probe

Figure 17:
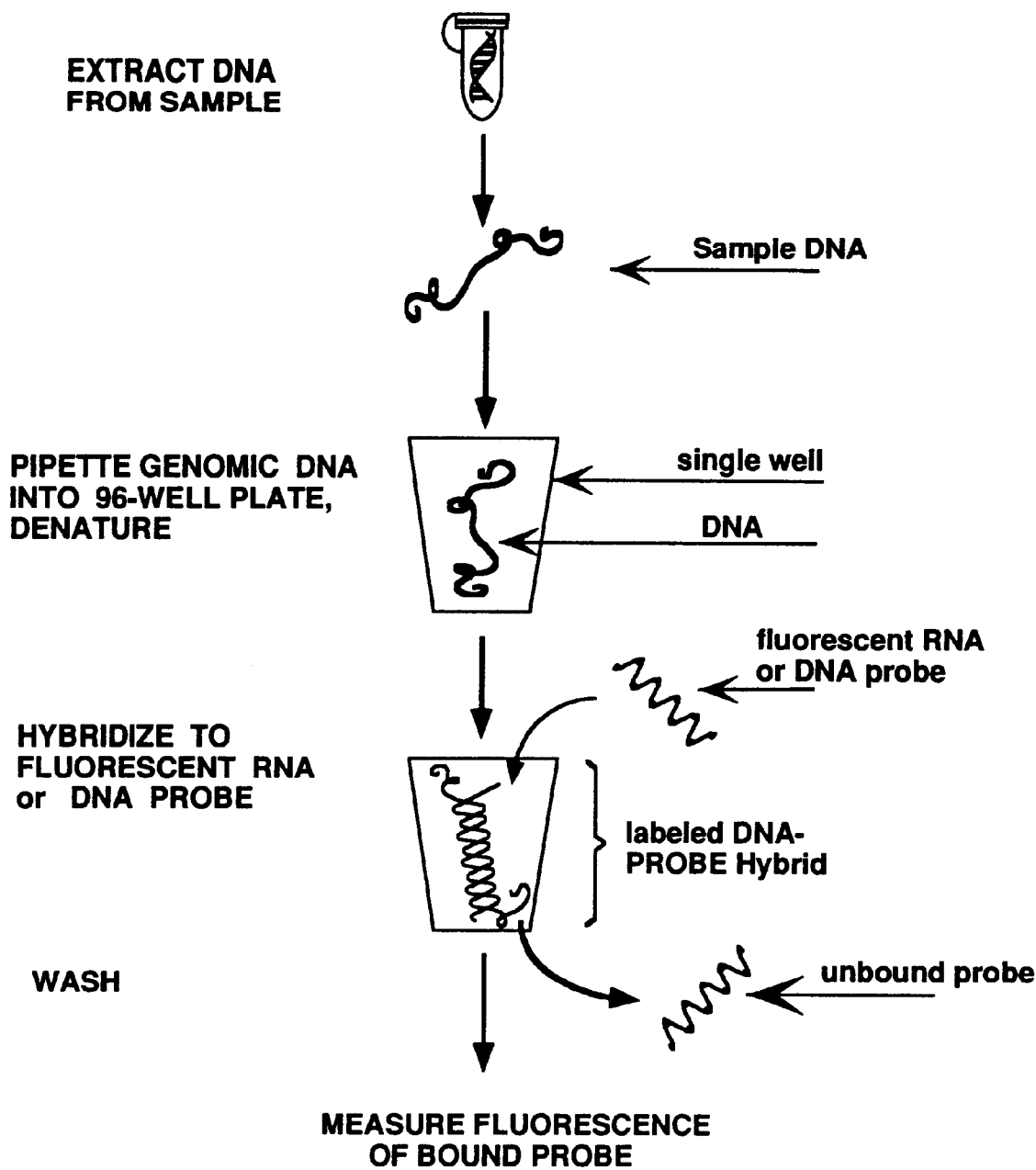
FIG. 17 is a diagram of detection of a target DNA sequence in genomic DNA hybridization with fluorescent probes.
Figure 18:
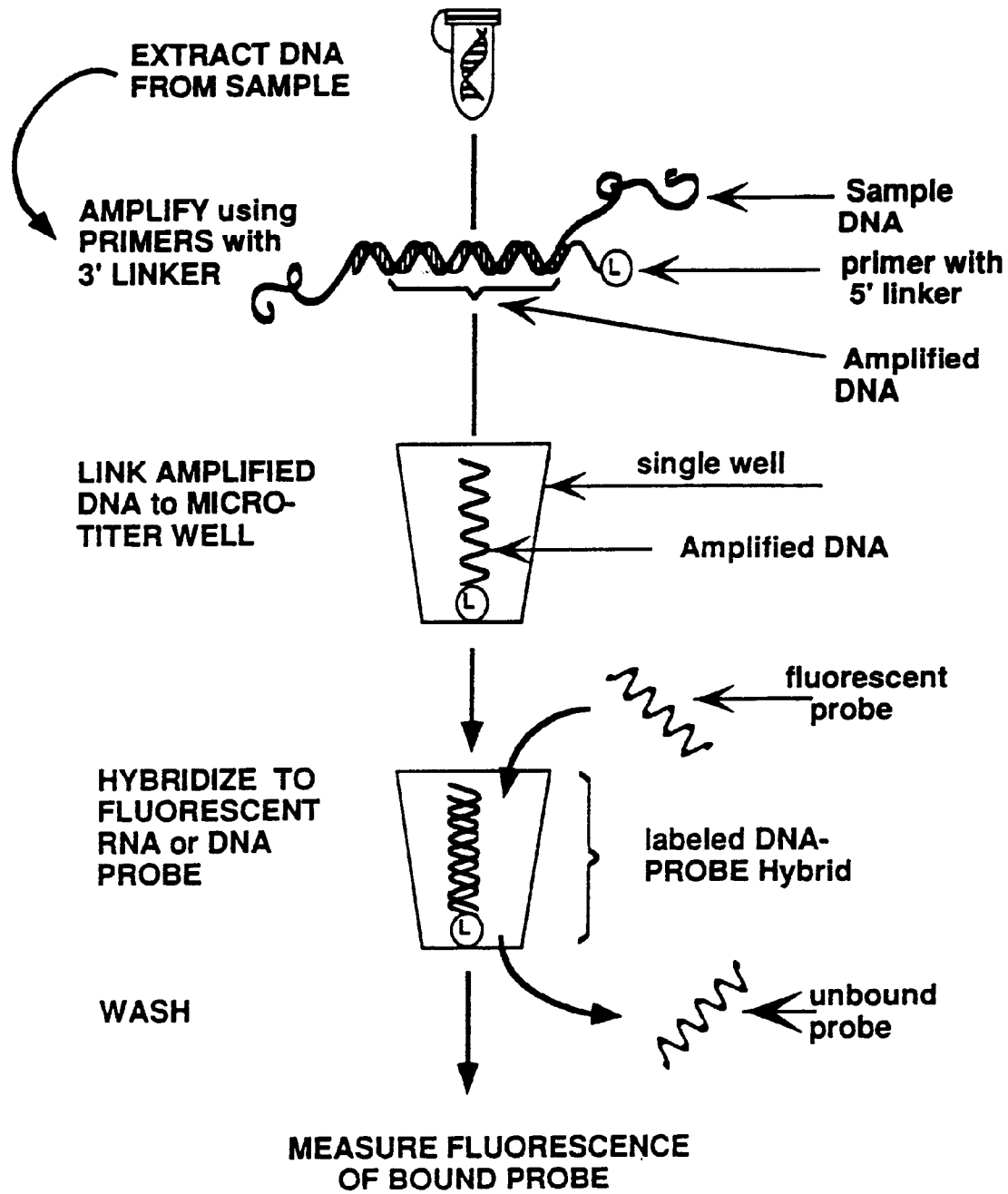
FIG. 18 is a diagram of detection of an amplified DNA segment by solution hybridization of a fluorescent probe.

*Chlamydia trachomatis* is an obligatory intracellular pathogen which, in its active infectious stages, contains from $3 \times 10^3$ to $4 \times 10^3$ copies of ribosomal RNA (rRNA) and one copy of genomic DNA/bacterium. A primer pair, one of which contained a 5'-biotinylated T7 promoter which was 5' to the hybridizing primer sequence, was used to amplify a 150 base pair DNA segment of the MOMP gene from a stock strain of *C. trachomatis* L2. Approximately 500 ng of the DNA fragment, which contained the T7 RNA polymerase promoter at the 5' end, was transcribed with T7 RNA polymerase in the presence of rCTP, rUTP, rGTP, and with either rFTP or rATP (+control). The reaction was stopped by heat inactivating the enzyme for 3 minutes at 100° C. Unincorporated rNTPs were separated from the labeled RNA by gel sizing chromatography on a Sephadex G-25 column, after which the probe concentration was estimated from its absorbance at 260 nm. Using a simple dual monochromator fluorescence spectrophotometer, as little as $5 \times 10^{-14}$ moles of the RNA probe could be detected over background when 20 nm slits were used for both excitation and emission monochromators. A photon counting fluorimeter designed for sensitivity (see Example 9, below) is capable of detecting between $5 \times 10^{-16}$ and $5 \times 10^{-17}$ moles of the same probe, equivalent to the amount of ribosomal RNA expected from between 5000 to 50,000 of the bacteria. Two hundred microliters of either (i) *C. trachomatis* genomic DNA, or (ii) the amplified target DNA were mixed with 200 $\mu$L of a 1/200 dilution of the probe in hybridization buffer (0.15 M NaCl, 0.02 M sodium citrate, 0.02 M HEPES, 0.004 M EDTA, pH 7.4) and the mixture boiled for 3 minutes, after which they were allowed to cool slowly to room temperature over one hour. An aliquot of the genomic DNA sample was eluted into an ultra filtration microtube or 96-well filter plate (pore size=0.1 $\mu$m) as illustrated in FIG. 17, washed 5 times with 0.15 M NaCl, 0.02 M sodium citrate, pH 7.4, after which the sample was divided in two, one half denatured in high pH buffer, and both aliquots scanned to measure fluorescence background and the fluorescence of hybridized probe, respectively. Target DNA amplimers were treated similarly except that the 5'-biotinylated primer end of the target DNA segments were first adsorbed to avidinylated magnetic beads (2.8 $\mu$m diameter) so that the sample could be washed without loss of material (FIG. 18). With either treatment, fluorescence of the probe may be detected at dilutions of the sample which contain less than $1 \times 10^{-16}$ moles of target DNA, which is roughly equivalent to the sensitivity required to detect less than 10,000 bacteria if a single similarly sized probe were used to detect rRNA from infectious Chlamydia. The probe used here is about 150 bases in length, contains approximately 38 formycin residues per probe, and binds only to a single target site on each copy of the ribosomal RNA. It is an important feature of this invention that increasing the number of fluorophores in a probe, or probe "cocktail," also increases the sensitivity of detection. With 13 times as many formycin residues per probe as the 150 base MOMP gene probe, $1 \times 10^{-18}$ moles of the Xef-1α probe can be detected in a dual monochromator fluorescence spectrophotometer whereas less than $1 \times 10^{-20}$ moles are detected using the photon counting technology described in Example 9.

EXAMPLE 7

Detection of Multiple Target Sites

An important aspect of the asymmetric syntheses to both diagnostic and therapeutic, e.g., antisense, applications of nucleic acid probes is the capacity for concurrent synthesis of probe "cocktails" which may comprise probes which differ in length or differ in the locations or numbers of the target sites on RNA or genomic DNA to which they will bind. Utilization of probe cocktails to three different types of diagnostic targets illustrate the broad importance of this feature.

Figure 20:
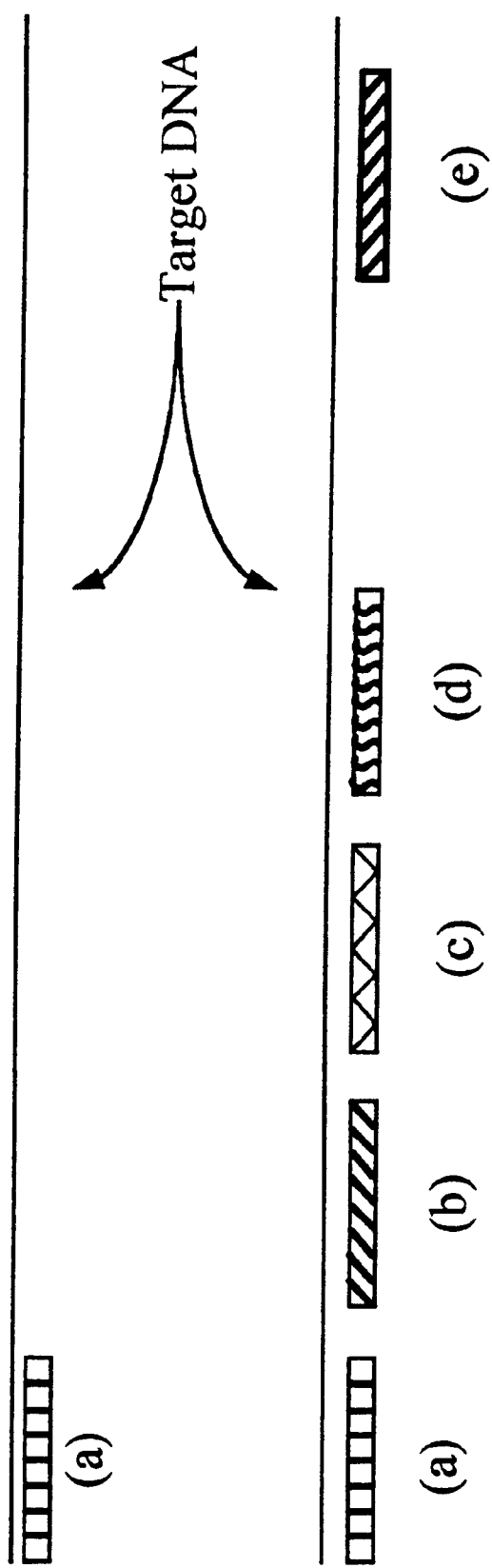
FIG. 20 shows a schematic of the mechanism for increasing detection sensitivity by the use of a probe "cocktail" which contains multiple probes of different sequences.

A. Single target nucleic acids present in multiple copies. In some species of pathogen, multiple copies of rRNA are present in each organism, e.g., each bacterium of *Chlamydia trachomatis* contains approximately $2 \times 10^4$ rRNA molecules per organism. Since the rRNA of Chlamydia is typically between 3000 and 5000 nucleotides in length, sensitivity in a diagnostic assay may be increased significantly by use of a probe cocktail specific for target sequences on rRNA and made of as many as 5 to 10 different probe sequences, each of which can bind to discrete segments of the target rRNA or target DNA as indicated with probes (a) to (e) in the lower half of the diagram shown in FIG. 20 in which (a), (b), (c), (d), and (e) are analogous complementary probes specific for different target sequences of a single DNA strand.

There are two disadvantages in using rRNA sequences as diagnostic targets: (i) rRNA sequences are highly conserved, hence only short variable sequences are useful for the detection and identification of infectious pathogens. One consequence of this to diagnostic sensitivity is that only limited numbers of 'reporter' labels can be used on each probe, thereby limiting sensitivity; and (ii) only a few pathogens carry rRNA in high copy numbers, and many, such as the DNA viruses, carry no rRNA at all, hence the number of diagnostics which can employ this strategy is limited.

B. Multiple different target sequences on a single strand of DNA. The genomes of all organisms are significantly larger than rRNA and typically carry more numerous and larger unique segments which can serve as target sequences for nucleic acid probe hybridization. For example, the complete genome of *Chlamydia trachomatis* has been isolated and consists of a relative small double stranded DNA with a molecular weight of $>660 \times 10^6$ or slightly more than $1 \times 10^6$ base pairs. Each bacterium also contains a $4.4 \times 10^6$ dalton plasmid containing >7 kbases. Unlike the rRNA of this species, the plasmid is unique to Chlamydia in its entirety— no cross-hybridization can be detected with the DNA from, e.g., *Neisseria gonorrhea*—indeed, no cross-hybridization occurs between the different restriction fragments of the plasmid itself. Even when no other portion of the Chlamydia genomic DNA is chosen for use as hybridization targets, a cocktail specific for the multiple restriction fragments of the Chlamydia plasmid alone is equivalent in length to more than 4 Xef-1α probes and can be detected at levels equivalent to between 100 and 1000 bacteria.

C. Multiple copies of a single target sequence on a single strand of DNA. It has only recently been discovered that flanking sequences on each side of several genes contain moderate to long stretches of tandem repeats. Ribosomal gene repeats are of particular interest in the kinds of DNA based diagnosis described in this invention. Like the ribosomal genes, they are present in high copy numbers, which improves sensitivity of detection but, in addition, the spacer regions between genes are normally highly variable from species to species, since they are not subject to selective pressures. Multiple copies of the same unique sequence on a single DNA strand represents a special case in which the hybridization targets are a cocktail of loci on each genome; that is, a single probe sequence can probe multiple target sites of the same sequence and on the same DNA strand. They are ideally suited as species and genus specific probe targets.

A representative example of such probes and targets was created for the different species of the protozoan parasite Eimeria, which causes coccidiosis in a variety of domestic animals. Genomic DNA from *E. tenella* was digested with several different restriction enzymes, and the fragments ligated into appropriately cut asymmetric plasmid vectors and were used to transform *Escherichia coli*. Colonies were screened for repeat sequences by hybridization with *Eimeria tenella* genomic DNA that had been labeled with 35S by random priming. Strongly hybridizing clones were picked and subjected to differential screening with labeled genomic DNA from *E. mitis, E. maxima, E. acervulina*, and *E. tenella*, as well as DNA from the closely related genera Plasmodium, Trypanosoma, and Sarcocystis. The majority of clones gave signals of equal intensity with DNA from the other genera. Some clones, however, were recognized specifically by the Eimeria and one clone was recognized only by *E. tenella*.

The entire sequence of the insert in the latter clone contains 334 base pairs. Physical characterization of the restriction fragments indicates that the sequence is present in tandemly repeated units of approximately 738 base pairs and that a minimum of 30 genes are tandemly linked and all appear to be on one chromosome. Asymmetric probes synthesized using the tandem repeat as a template contain 179 formycin A residues per template sequence.

Even when no other portion of the Eimeria genomic DNA is chosen for use as a hybridization target, a single sequence probe specific for only the multiple copies of the tandem repeat on the Eimeria genome is equivalent in length to more than 11 Xef-1α probes. Since the infectious particles for Eimeria are oocysts, each of which contains 8 genomes, such cocktail of targets makes it possible to detect less than 10 oocysts. The import of tandem repeat targets extends well beyond sensitivity, however, or simply the detection of this single genus, since tandem repeat sequences appear in a genomic DNA of a wide variety of species and genera, and are distinct for those species, thereby providing a broad basis for the design of diagnostic assays for a wide variety of pathogens, including those for which no rRNA targets exist.

EXAMPLE 8
The Use of Non-Specific and Non-Hybridizing Fluorescent Oligomers as Universal Fluorescent "Tags" by Ligation or Chemical Linkage Simple modification of the template to produce a "sticky end" at the 3', 5', or both 3' and 5' termini, e.g., to $^{5'}$ACGT-polyd(AT), polyd(AT)-TGCA$^{3'}$, or $^{5'}$ACGT-polyd(AT)-TGCA$^{3'}$, respectively, enabled synthesis of nucleic acid probes with all of the above properties, but which could also be ligated, either (i) to like strands to produce longer fluorescent probes, or (ii) to other hybridization sequences specific for a prescribed target DNA. The latter is a particularly useful way in which to produce a universal label for any cloned DNA fragment, and allows a given probe to be identified by two non-hybridizing but highly fluorescent sequences at its termini, without the need to denature the hybrid for detection as was seen with the simple poly (FU) probe, above. Equivalent non-hybridizing universal probes can be readily made by chemical synthesis using, e.g, the etheno analog phosphoramidites, e.g., 1,$N_6$-ethenoAdenosine-3'-O-phosphoramidite (eA), to synthesize non-specific tags which can subsequently be linked to any hybridization probe. The 3' or 5' termini of such universal probes can also be prepared for chemical, rather than enzymatic attachment to other oligomers or solid phases, through the addition of, e.g., 5'-amino hexyl, 5'-sulfhydryl hexyl, 3'-aminohexyl amino, N-hydroxysuccinimide esters, and other such linkers. The unique application of this probe technology, which employs the universal end label, is quantitative and works well for routine assays which require high sensitivity. Another application of this technology referred to herein as "sustained signal amplification" is non-quantitative and can be useful for a situation where extreme sensitivity is required to answer "yes" or "no" whether a particular gene marker is at all present, for example, where low copy numbers of a target sequence are present. "Sustained Signal Amplification" is described in more detail in Example 8(B), below.

A. The 5' Universal End Label

Homopolymers of non-hydrogen bonding fluorescent nucleoside analogs, e.g., ethenoadenosine, can be used together with asymmetric synthesis of ssDNA and RNA to increase the density of fluorescent labeling on cocktails of small probes, on small fragments as in sequencing, and to increase sensitivity of labeling of small or low copy number target. The general concept comprises an oligomeric probe constructed along a typical phosphodiester backbone, but which can be divided into distinct functional regions-the 5' fluorescent homopolymer; primer, or promoter complement; an optional "tether" region, which can connect the homopolymer to the primer; and a target complement. A diagram of this described 5' universal end label is shown in FIG. 22.

Figure 22:
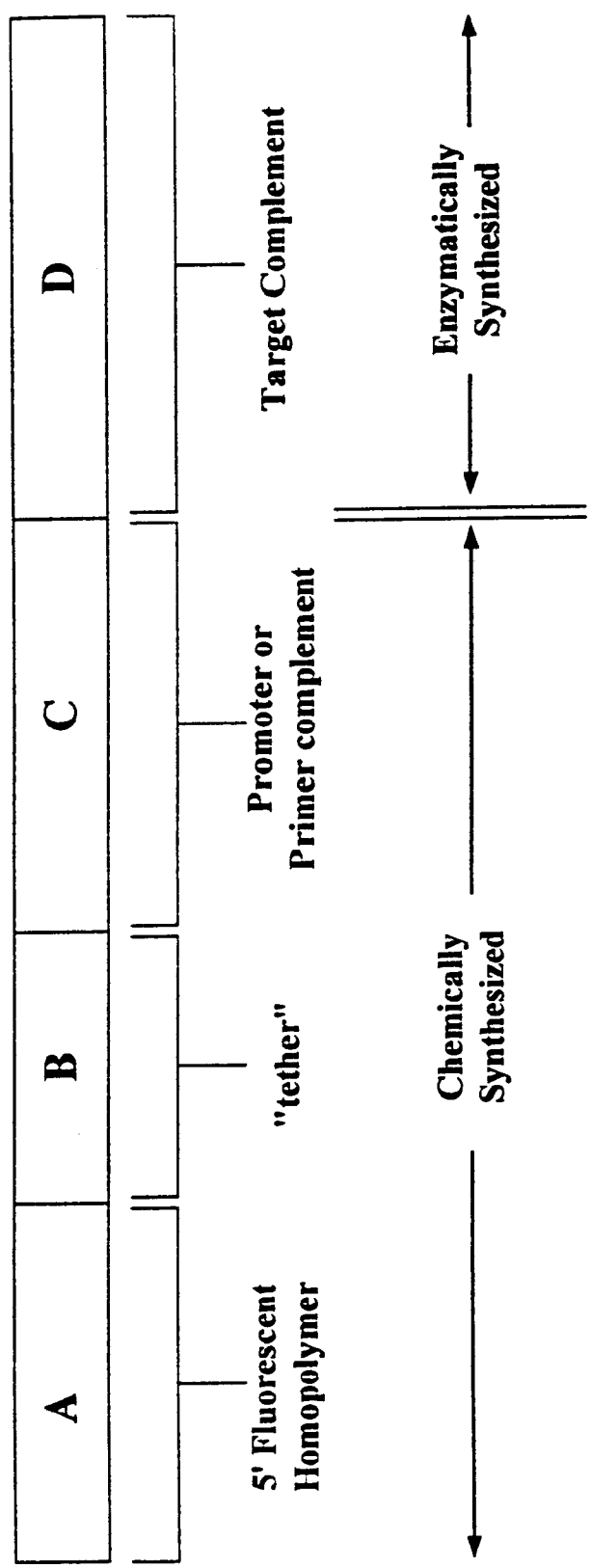
FIG. 22 shows the 5' universal end label comprising four distinct functional groups which include: region A, a non-base-pairing homopolymer from 1 to about 50 fluorescent nucleoside analogs long; region B, an optional non-nucleoside phosphodiester "tether" connecting region A to region C; region C, an enzymatic synthesis primer, complementary to a promoter in the target sequence; and region D, a nucleotide chain from about 40 to about 20,000 nucleotides in length complementary to the target nucleotide sequence. Regions A, B, and C which are typically 20 to 60 bases in length can be chemically synthesized. Region D can preferably be enzymatically synthesized. The synthesis of the 5' universal end label is described in Example 8.

The functional regions of the phosphodiester chain as shown in FIG. 22 are:

A=a non-base pairing homopolymer of from 1 to about 50 fluorescent nucleotide analogs;

B=an optional non-nucleotide phosphodiester "tether" comprising, e.g., one or more freely rotating alkyl chains inserted as part of the phosphodiester backbone of the oligomer;

C=an enzymatic synthesis primer for use in initiating enzymatic synthesis of the target-specificD region. Representative examples would be the complementary sequences to the T7 RNA polymerase promoter or to the M13 forwarded primer as are used in asymmetric RNA or DNA probe systhesis described herein;

Regions A, B, and C, typically from 20 to 60 bases in length, can be chemically synthesized. The 5' universal end label comprises at least regions A and C and, alternatively, can also include the optional region B.

D=a target complementary sequence of from 40 to 20,000 nucleotides in length. This sequence may or may not include fluorescent nucleotide analogs, but functions primarily as the region which establishes target specificity. This region is also distinct from the other regions in that it is enzymatically synthesized from templates adjacent to the promoter or primer site to which region C is complementary. The entire 5' universal end label can be used as the primer for DNA or RNA replication of the target-specific complement.

Figure 23:
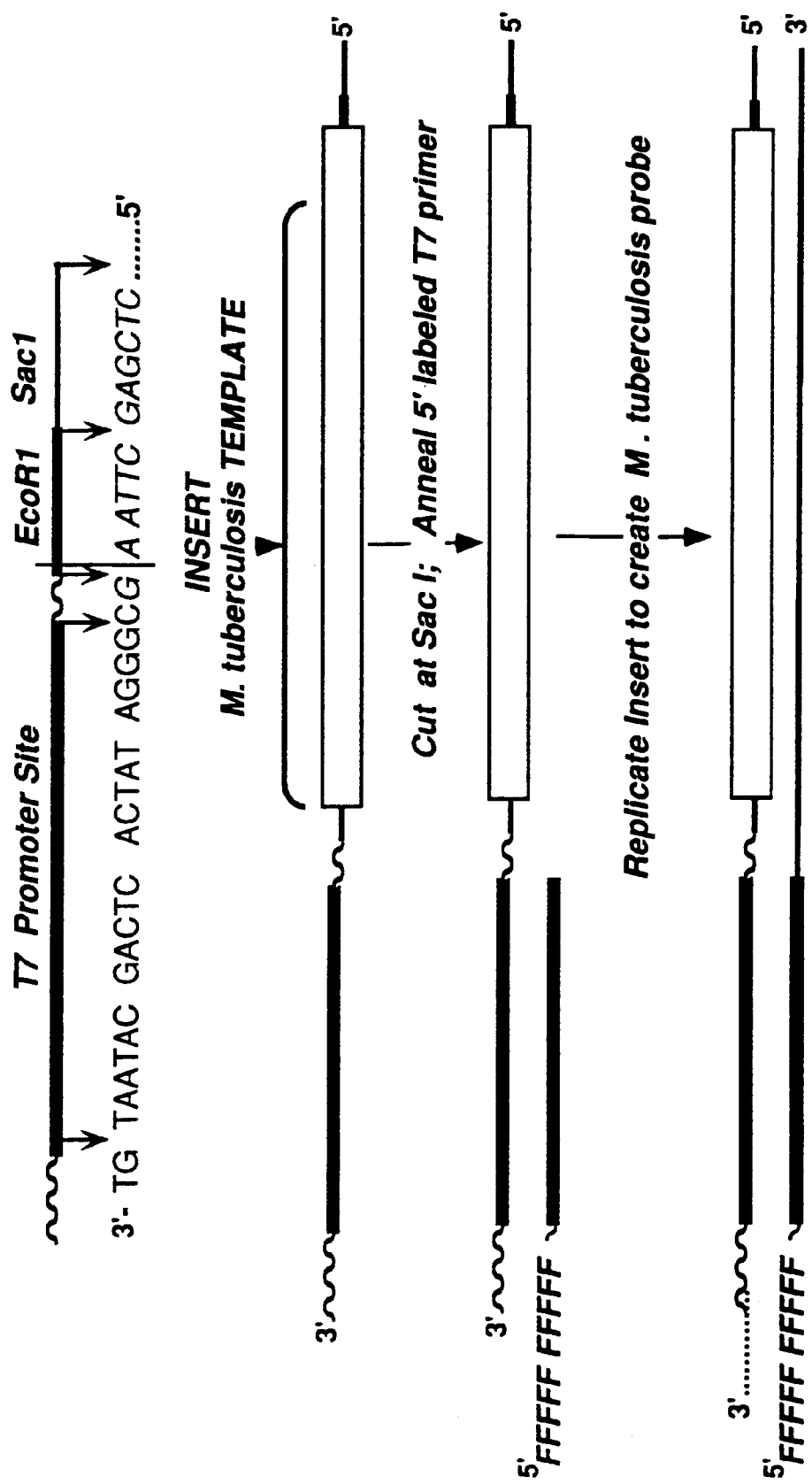
FIG. 23 shows a schematic representation of the method for synthesizing a highly flourescent 5' labeled probe. The method comprises the following steps: (1) restricting, with a specific restriction enzyme, a sequence having a known promoter site and known restriction site downstream from the known promoter site, (2) inserting a unique target sequence at the restriction site, (3) hybridizing a fluorescent nucleoside analog probe comprising a sequence complementary to the promoter of the inserted target sequence, and (4) extending the probe sequence from the hybridized promoter region, using a nucleic acid polymerase, to synthesize a specific probe complementary to the inserted target sequence.

Enzymatic synthesis using a 5' universal end label is illustrated using the *M. tuberculosis* IS6110 template (a sequence unique to the bacterium) which has been inserted into a standard Gemini plasmid to create a synthesis template. Other plasmids can be used as well. This enzymatic synthesis process is shown in FIG. 23. The following advantageous properties of the 5' universal end label have also been discovered.

Figure 24:
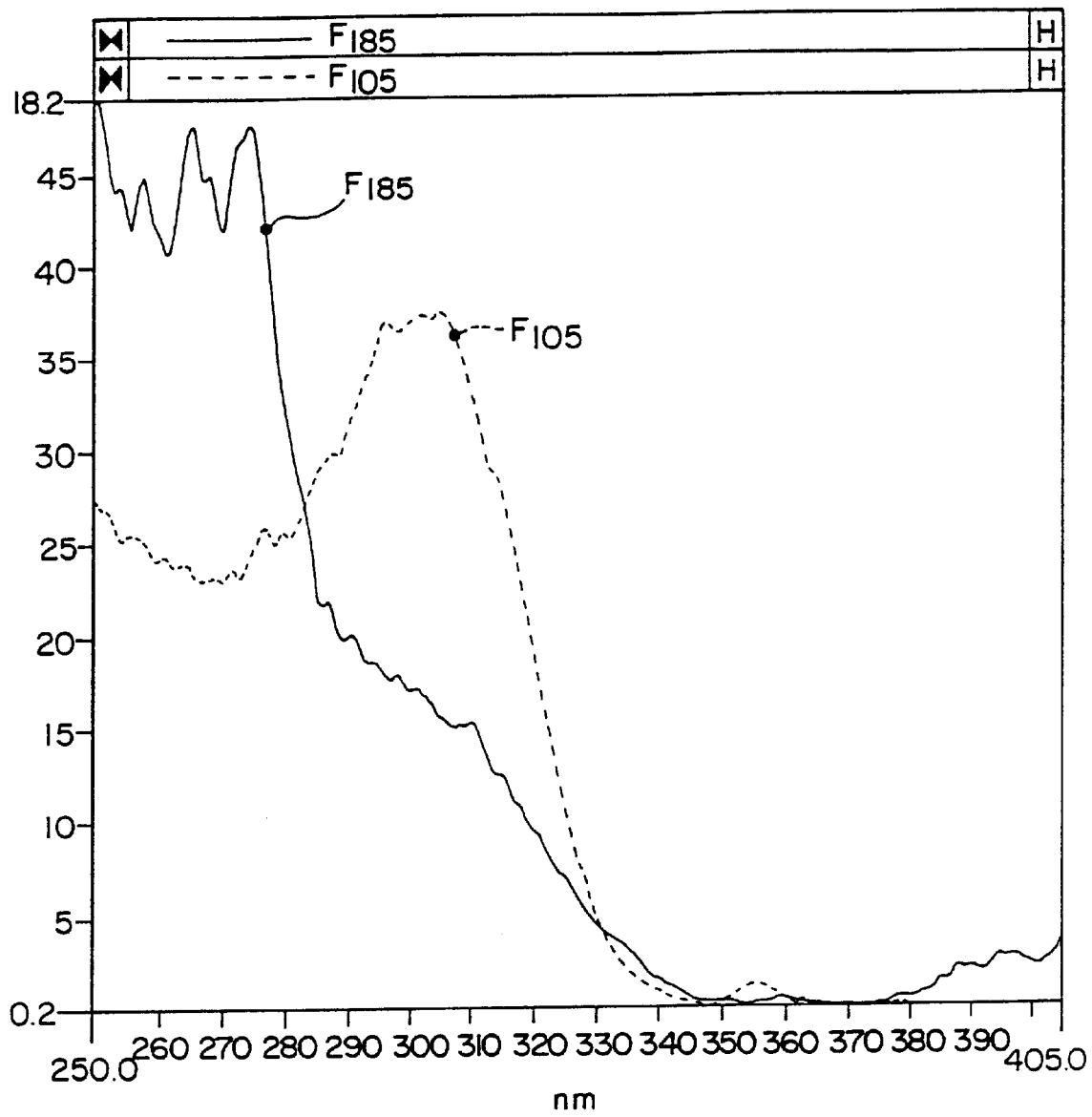
FIG. 24 shows the normalized spectrum profiles compared for $F_{185}$ (ethenoadenosine)and F105 (formycin). The spectra were determined between 250–405 nm for the compounds, using a 2.5 nm slit.

(1) As shown in FIG. 24, the excitation spectrum of one non-hydrogen bonding fluorescent analog, ethenoadesosine (designated $F_{185}$), is compared with the comparable excitation spectrum of formycin ($F_{105}$). The $F_{185}$ extends further into the UV wavelengths. Two important discoveries have been made about both the excitation and emission spectra of $F_{185}$: (i) the wavelength maxima are the same at both pH 7 and pH 11, and (ii) the quantum yield is more than 10× that of $F_{105}$ having values of 0.55 and 0.65 at pH 7 and 11, respectively. This allows the use of the 5' universal end label under a wider variety of pH conditions and can result in significantly greater luminescence from fewer total fluorophores. It has been shown that an $F_{185}$ 20-mer which is excited at pH 11 over the range $270 \text{ nm} \leq \lambda \leq 310 \text{ nm}$ can be equivalent to labeling with between 3 and 10 fluorescein molecules. Furthermore, the fluorescence does not quench and can be used with time resolved spectroscopy.

(2) non-base pairing end labels do not interfere with primer-mediated DNA amplification or replication, are water soluble at concentrations up to $10^{-3}$ M, and do not increase the background in a binding assay due to non-specific hybridization to non-target sequences.

Figure 25:
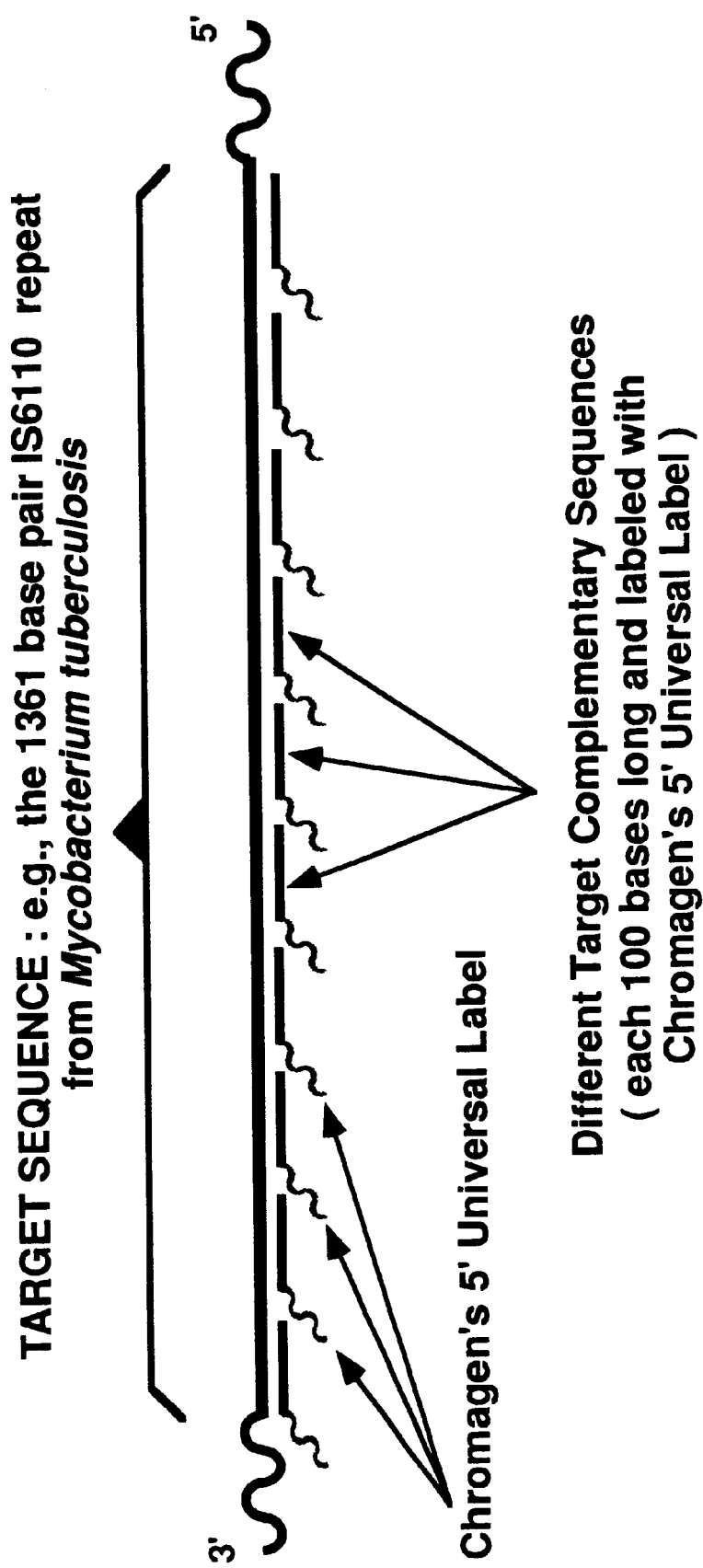
FIG. 25 shows a method for increasing sensitivity of detection or differential labeling using multiple copies of a 5' universal end label. Shown is an example of a target sequence, using the 1361 base pair IS6110 repeat from *Mycobacterium tuberculosis*. The non-hybridized portion of the probe is the 5' universal end label on each of a plurality of probe sequences where each of the probe sequences is complementary to a different fragment or segment of the target sequence.

(3) such probes are beyond the capacity of chemically synthesized probes because, as is well known in the art, the practical limit of synthesis in reasonable yield remains approximately 60 bases. The 5' universal end label can be used to increase sensitivity of detection by using a cocktail of relatively short probes for which the length of the "D" region is approximately 100 bases. For example, as illustrated in FIG. 25, the 1361 bp IS6110 sequence of *M. tuberculosis* has been used as a target for a cocktail of 10 probes, each having a different "D" segment or complementary target sequence. Each probe, however, bears the same 5' universal end label. In the case of *M. tuberculosis*, there are 16 copies of the IS6110 gene per bacterium. By using the end label in a manner shown in FIG. 25, each bacterium has the potential for being labeled by a probe cocktail with permanent fluorophores which are equivalent in instantaneous emission to between 480 and 1600 fluorescein molecules.

Figure 26:
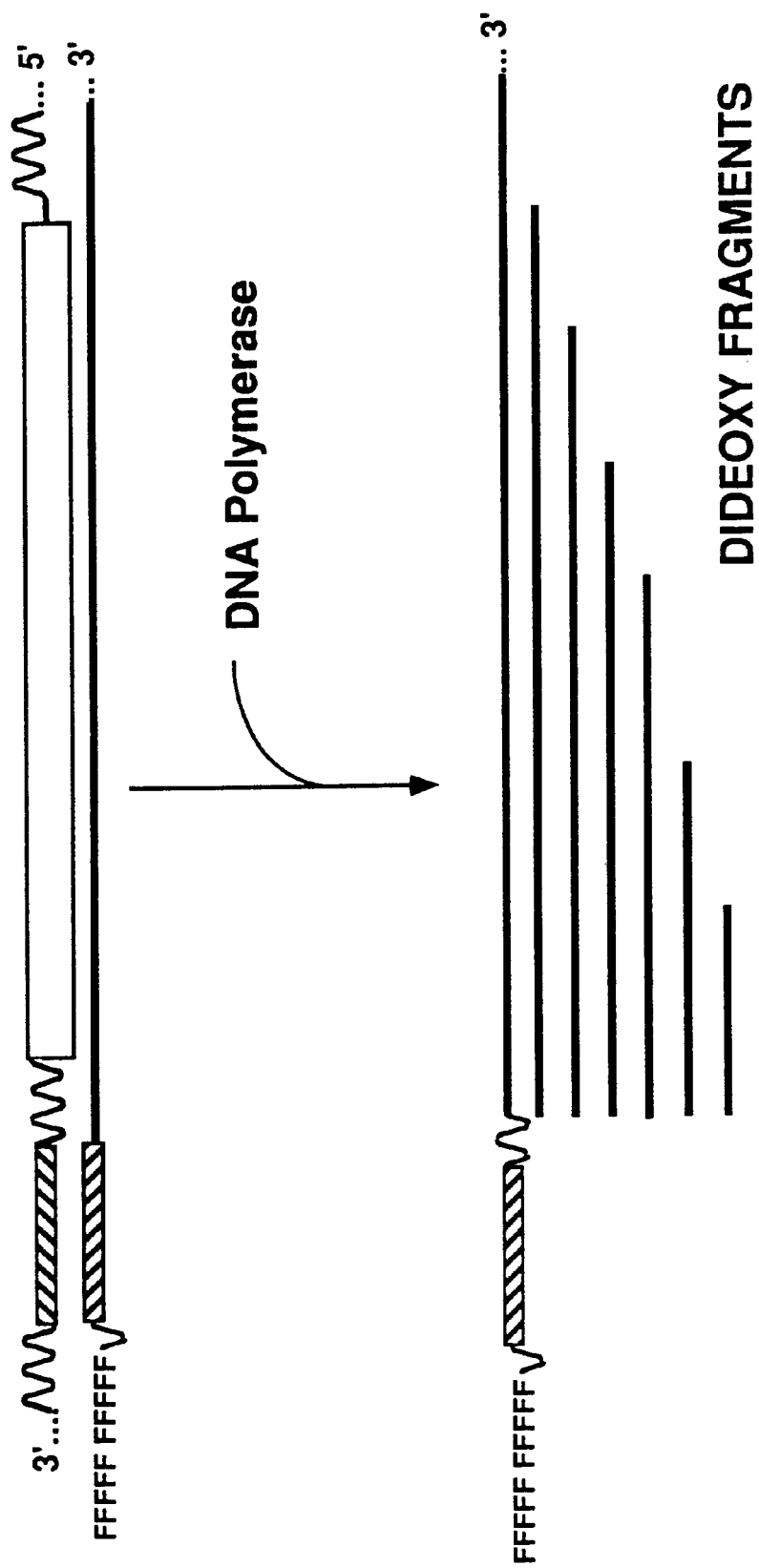
FIG. 26 shows the sequencing application of 5' universal end label. The unique probe (which can be produced by the method shown in FIG. 24) can be employed using DNA polymerase to produce a plurality of dideoxy fragments having different lengths.

(4) the same labeling device can be used to provide a standardized fluorescent label in standard DNA sequencing, but having pre-labeled DNA fragments so that sequences can be read or recorded directly from the gel. Such a use is depicted in FIG. 26.

B. Sustained Signal Amplification (SSA)

The 5' universal end label should prove particularly useful for those situations in which a unique genetic marker is present only in a relatively few copy numbers of target genes present in a large genome. For such applications in which exquisitely sensitive levels of detection are required, or for which very little target is present, some combination of fluorescent labeling and signal replicationor amplification is required. Hepatitis B presents such a case. The entire genome of Hepatitis B virus (HBV) is only 3200 bases long and, in the virion, one of the strands is even shorter. The virion contains a DNA polymerase which utilizes nucleotide triphosphates from a host cell to complete the short chain as the first step in an infection.

Figure 27:
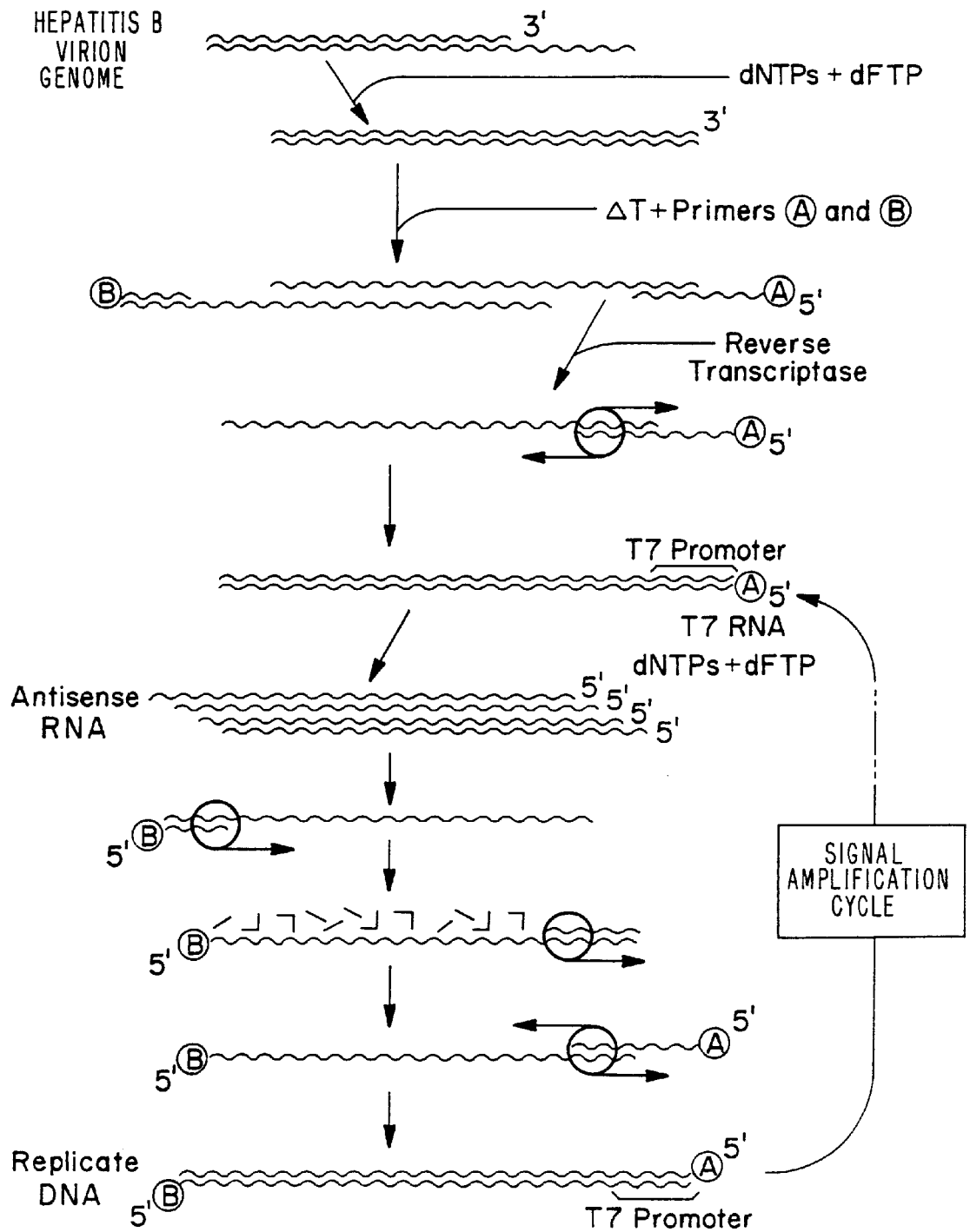
FIG. 27 shows the Sustained Signal Amplification procedure. The example in the figure employs the genome from the Hepatitis B virion having two unequal lengths of DNA forming its double-stranded genome. The method shows the steps: (1) extension of the shorter DNA strand using nucleotides or phosphorylated nucleoside analogs; (2) the separation of the two strands and the addition of two primers, A and B; (3) extension of the DNA strand to which the A primer is hybridized using reverse transcriptase; (4) utilization of the synthesized double-stranded sequence in an amplification cycle which comprises (a) production of anti-sense RNA template from the synthesized DNA using an RNA polymerase, (b) synthesis of DNA from the RNA template using primer B and a nucleic acid polymerase, and (c) synthesis of double stranded DNA (DNA replicate) from the B primer DNA. The replicate DNA can then repeat the signal amplification cycle (step (4)).

The DNA polymerase of the virion utilized together with a novel fluorescent nucleoside analog described herein was combined with a non-PCR type of amplification which has heretofore been used only for RNA replication. In this scheme, shown in FIG. 27, the virion DNA serves as an in situ template and, in combination with the above-described asymmetric synthesis method, can be used to amplify the intensity of the fluorescent signal. The process, which may be better understood by referring to FIG. 27, involves two steps. First, the sample DNA is combined with (i) deoxynucleotide triphosphates (deoxyNTPs) including triphosphorylated fluorescent nucleoside analogs, and, (ii) two primers (shown as A and B in FIG. 27), the first of which has at its 5' end a sequence complementary to an RNA polymerase promoter. The primers referred to in this Example are described as "A" and "B" to indicate the use of two separate primer. These are described as such for illustrative purposes and, as such, would be understood by those in the art to refer to any primer which comprises a sequence complementary to a promoter region on the target sequence and which can be used with a nucleic acid polymerase. In the illustration shown in FIG. 27, the T7 RNA polymerase promoter is designated by the thicker line at the end of primer A. The sample is first incubated at 37° C. for 10 minutes to allow the viral DNA polymerase to complete the short genomic strand; the sample is then raised to 65° C. for 1 minute to denature the genome, after which the primers are annealed at 42° C. Second, the two enzymes, reverse transcriptase and T7 RNA polymerase, are added, together with the riboseNTPs including the fluorescen tribonucleoside analogs, and the entire sample is incubated at 42° C. for 1 hour. This creates a cycling synthesis of DNA strands and RNA strands as indicated in the lower half of FIG. 27. The net effect is to produce somewhere between $10^8$ and $10^9$ fluorescentRNA strands and about 100-fold less fluorescent DNA strands. Following a wash of the sample in a cell-free unit to remove the unused monomeric fluorescent NTP's, the sample can be simply read for fluorescence to determine whether any template, in this case Hepatitis B DNA, was present in the sample.

EXAMPLE 9

Quantitation of Luminescent Probe Using Time Resolved Fluorometry

A novel method for detecting fluorescent nucleoside analogs, fluorescent oligonucleotides or analogous sequences, of the amount of bound fluorescent oligonucleotide probe has been developed based on the use of photon counting to measure the amount of a fluorophore in a sample and is described herein below. The method differs from time resolved spectroscopy in that the method integrates all fluorescence emission from a fluorophore or nucleic acid probe, independent of the wavelength of the emission and is both a novel combination of time and spectral integration and a novel application of photon counting to the identification, detection, and quantitation of nucleic acid target sequences to diagnostic assays and therapeutic treatments.

The fundamental experimental parameter used in any measurement of luminescence is the intensity of the luminescence, 1, the units of which are moles of photons per second per liter. Because the fluorescent nucleoside analogs used here are, for all practical purposes, permanently fluorescent and do not photo bleach within the lifetime of a typical measurement, the luminescence of fluorescence, measured in moles of photons emitted per second per mole of fluorophore, can be used as an index of the amount of fluorophore, and hence probe, in a sample. The preferred instrumentation for such measurements, developed at Chromagen, comprises (i) a 150 watt Hg/Xe CW cylindrical lamp capable of high intensity excitation over the range 290 nm$\leq\lambda\leq$320 nm, (ii) an ultrahigh sensitivity photomultiplier in which the photodynode is coated to allow a response only over the range of emission 360 nm$\leq\lambda\leq$550 nm, (iii) a cylindrical cuvette with quartz excitation windows but glass walls which can serve as the emission filter. The cuvette is mounted so that the entire sample can be collected at the face of the photomultiplier tube, and (iv) 5 computer-driven photon counting clocks, connected in seriatim, and each capable of discriminating between photons at a frequency of $10^9$ per second.

In experiments with the monomeric formycin A and full-length Xef-1α probe containing 489 formycin residues under conditions of room temperature and pH=10, we have found that (i) the luminescence of serial dilutions of the monomer and the probe are linearly related to the concentration, and (ii) the luminescence of the probe is equivalent to the same number of free monomers. In a typical assay using permanent fluorophores such as those shown in FIGS. 17 and 18, the amount of target present in a sample is determined by denaturing hybrids after unbound probe has been washed away and measuring the amount of probe which was bound. The fluorescence equivalence of residues in an analogous probe sequence to the emission of the same number of monomers, under alkaline conditions used here, indicates that there is negligible self-quenching in the oligomer and demonstrates that the luminescence of the probe can be used directly to quantitate the amount of probe bound by target RNA or DNA, thereby providing a broad basis for the design of diagnostic detectors for a wide variety of nucleic acid assays and diagnostics. It is an important consequence of the invention, that sensitivity and signal-to-noise ratios are a function of the number of the photons counted and the number of time periods over which counting is done.

EXAMPLE 10

Attachment of 5' and 3' Linkers for Immobilization of the Oligonucleotides and Hybrids or for Attachment of Fluorescent Oligomers as "Labels"

The chemistries and procedures of the invention can be used to create and characterize any probe synthesized using fluorescent nucleoside analogs, whether the synthesis is enzymatic or chemical, for both fluorescence and hybridization specificity. Such probes can be used not only in the solution hybridization formats described here, but also in the more frequently used laboratory procedures such as "dot-blot" detection, electrophoresis in agarose or polyacrylamide gels, Southern blotting, and hybridization on filters and membranes, as well as separation of the hybrids by HPLC or capillary electrophoresis methods. Although linkers are not essential to the solution hybridization, any appropriate affinity linker such as biotin/avidin or homo- or heterobifunctional linker can be used to capture the probe or hybrid for purposes of concentration, isolation, or detection, as illustrated for the PCR amplified DNA fragments of FIG. 18. The present invention includes linker derivatized fluorescent nucleotides, as well as oligonucleotides, linker derivatized primers for use in amplification and subsequent detection with fluorescent oligonucleotide probes, oligonucleotide probes, plasmids, and therapeutics made or otherwise "tagged" therefrom, and/or their uses and applications such as are described herein. Such derivatizations include, but are not limited to, transaminations to purine or pyrimidine nucleosides and/or their fluorescent structural analogs, amino-thiol, azido-, aldehyde, hydroxysuccinimide, 5' aminoalkyl-3'-O-phosphoramidite, 5'-thioalkyl-3'-O-phosphoramidite, 3'-aminohexyl amino, amino silanes, and aminosilyl derivatives and other such linkers and groups reactive with linkers or in condensation reactions such as Schiff base condensations of 3' or 5' oxidized cis-diols, as are familiar to one skilled in the art. To illustrate this a specific case is offered:

(i) a set of non-fluorescent amplification primers for the MOMP gene sequence was chemically synthesized; at the end of synthesis an additional cycle was used to add 5'-aminohexyl-3'-O-phosphoramidite to the 5' terminus of the completed primer with the addition chemically synthesized, using standard phosphotriester chemistry.

(ii) Following cleavage from the solid phase support in strong ethanolic base, the terminal amino group of each strand was reacted with NHS-biotin ester to provide the 5' biotinylated primers.

(iii) The primers were used for standard amplification, after which the amplimers were captured on avidinylated 96-well filter plates and washed to remove unreacted materials and contaminants.

(iv) The captured amplimers were hybridized with fluorescent analog labeled oligonucleotide probes as described above and the amount of target sequence in the amplimers quantified.

Included in the present invention are such attachments of fluorescent oligonucleotides to other fluorescent or non-fluorescent oligonucleotides to immobilizing beads, filters, or activated plastic plates and done through enzymatic attachment such as ligation, or chemical attachment through such linkers as are described herein.

EXAMPLE 11

Uses of Fluorescence Resonance Energy Transfer (FRET) to Broaden or Enhance the Uses of Fluorescent Nucleoside Analogs and Probes Oligonucleotides can be synthesized or derivatized as described herein which have two or more spectrally distinct, detectable labels, either by using two or more nucleoside analogs with discrete fluorescence emission characteristics, or by use of a covalently attached FRET acceptor, such as is described hereinabove. FRET acceptors can also be used to enhance or broaden the sensitivity of the detection for the fluorescent probes, if they are simply available in solution to act as acceptors of the probe emission. For example, the excitation spectra of such dyes as the coumarins, e.g., 7-amino-4-methylcoumarin-3-acetate, 7-methyl-umbelliferone, the naphthalene and anthracene dyes, etc., overlap the emission spectrum of oligomers constructed from the fluorescent nucleoside analogs, e.g., poly (FU), but not the oligomers' excitation spectrum. Such dyes as 7-amino-4-methylcoumarin-3-acetate may thus be used either (i) as a covalently attached FRET acceptor, e.g., by reacting the N-hydroxysuccinimide ester with prescribed amino groups on the oligomer, or (ii) by simply adding the dye to a solution of the probe to act as a FRET indicator of probe fluorescence. In addition to the obvious advantages of providing a second fluorescent label to the hybridization probe, this methodology allows amplification of the probe signal through more efficient capture of the emitted light, reduction of background light due to light scattering from excitation sources, and detection at longer visible wavelengths.

EXAMPLE 12

RNase Amplification Method

First an RNA fluorescent probe is contacted with a DNA sample. The RNA fluorescent probe hybridizes to a target DNA sequence. RNase H only digests RNA:DNA hybrids, not ssRNA probes. The resulting fluorescent monomers are released into solution, and a second RNA probe can hybridize to be digested. At the end of the experiment, the monomers are separated from probes on standard membranes, and the amount of monomer released is measured by simple fluorometry. The specimens with no DNA for hybrids will show no fluorescence.

In should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An improvement in methods of synthesis, amplification, enzymatic digestion, base-pairing, labeling, sequencing, replication, transcription, location, detection, or identification of DNA or RNA oligonucleotides, wherein said improvement comprises the incorporation of inherently fluorescent nucleosides, or structural analogs thereof, said inherently fluorescent nucleosides or structural analogs thereof being fluorescent under physiological conditions, having the following structures:

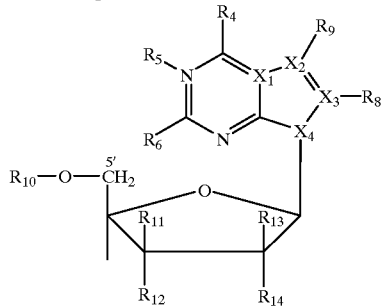

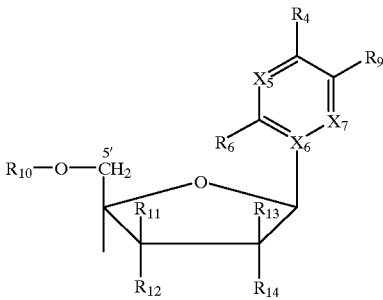

wherein $X_1$, $X_2$, $X_3$, $X_4$, $X_5$, and $X_6$=N, O, C, S, or Si, wherein at least one of $X_1$, $X_2$, $X_3$, $X_4$, $X_5$, or $X_6$=N, and wherein $X_7$ is —CH—;

$R_4$ is a reactive group derivatizable with a detectable label wherein said reactive group is selected from the group consisting of $NH_2$, SH, =O, and optionally, a linking moiety selected from the group consisting of an amide, a thioether, a disulfide, a combination of an amide a thioether or a disulfide, $R_1$—$(CH_2)_x$—$R_2$ and $R_1$—$R_2$—$(CH_2)_x$—$R_3$ wherein x is an integer from 1 to 25 inclusive, and $R_1$, $R_2$, and $R_3$ are H, OH, alkyl, acyl, amide, thioether, or disulfide, and wherein said detectable label is selected from the group consisting of radioisotopes, fluorescent or chemiluminescent reporter molecules, antibodies, haptens, biotin, photobiotin, digoxigenin, fluorescent aliphatic amino groups, avidin, enzymes, and acridinium; $R_5$ is H, absent, or part of an etheno linkage with $R_4$;

$R_6$ is H, $NH_2$, SH, or =O;

$R_8$ and $R_9$ are hydrogen, methyl, bromine, fluorine, or iodine; alkyl or aromatic substituents, or an optional linking moiety selected from the group consisting of an amide, a thioether, a disulfide linkage, and a combination thereof;

$R_{10}$ is hydrogen, an acid-sensitive/base-stable blocking group, or a phosphorous derivative;

$R_{11}$=$R_{13}$=H;

$R_{12}$ is hydrogen, OH, 3 amino, 3-azido, 3-thiol, 3-unsaturated or a 3-phosphorous derivative; and $R_{14}$ is H, OH, or $OR_3$ where $R_3$ is a reactive group, protecting group, or additional fluorophore;

provided that excluded from such structure is any purine-like compound in which:

(i) $X_1$=$X_4$=C; $X_2$=$X_3$=N; $R_4$=$NH_2$; $R_5$=$R_8$ which is absent; $R_6$=H; $R_9$ is H or is absent; $R_{10}$=H; and $R_{12}$=$R_{14}$=OH; or (ii) $X_1$=C; $X_2$=$X_3$=$X_4$=N; $R_4$=$NH_2$ or H; $R_5$=$R_8$ which is absent; $R_6$=$NH_2$; $R_9$ is H or is absent; $R_{10}$=H; and $R_{12}$=$R_{14}$OH; or (iii) $R_4$ and $R_5$ in combination form an etheno linkage; $R_6$=$R_8$=H; $R_9$ is absent; $X_1$=$X_3$=C; and $X_2$=$X_4$=N; or (iv) $X_1$=$X_2$=C; $X_3$=$X_4$=N; $R_4$=halogen or —S($CH_2$)$_n$R with n being an integer between 1–6 and R is lower alkoxy, alkylthio, phenoxy, phenylthio, unsubstituted or substituted phenyl, —C=C—R' wherein R' is unsubstituted or mono-, di- or trisubstituted phenyl; $R_9$=$R_{10}$=H; and $R_{12}$=$R_{14}$=acyloxy; or (v) $R_4$=$NH_2$ or OH; $R_5$ is absent; $R_9$ is —COOH, —$CONH_2$, —C(S)$NH_2$, —C(NH)$N_2$, or —C(N—$NH_2$)$NH_2$; $X_1$=$X_2$=$X_3$=C; and $X_4$=N;

and further provided that $R_8$ is absent if $X_3$=N and $R_9$ is absent if $X_2$=N;

and provided that the structure is not a nucleoside which is effectively non-fluorescent under physiological conditions and is selected from the group consisting of adenosine, cytidine, guanine, thymidine, uridine, and inosine.

2. The methods of claim 1, wherein said synthesis, amplification, labeling, detection, or identification of DNA or RNA oligonucleotides is by (i) chemical synthesis, polymerization, or linking methods; or (ii) enzymatic methods of amplification replication, endonuclease DNA or RNA digestion, transcription, terminal labeling, filling in, or nick translation.

* * * * *

UNITED STATES PATENT AND TRADEMARK OFFICE
CERTIFICATE OF CORRECTION

PATENT NO. : 6,268,132 B1
DATED : July 31, 2001
INVENTOR(S) : Michael J. Conrad

It is certified that error appears in the above-identified patent and that said Letters Patent is hereby corrected as shown below:

Column 4,
Line 17, "hybridizeto" should read -- hybridize to --.

Column 6,
Line 55, "shortcomingsto" should read -- shortcomings to --.

Column 9,
Line 45, "F105" should read -- $F_{105}$ --.

Column 11,
Line 22, "5-substitute" should read -- 5-substituted --.

Column 15,
Line 1, "nvel phosphoramidities" should read -- novel phosphoramidites --.

Column 16,
Line 8, "includingthe azanucleotidesand" should read -- including the azanucleotides and --.
Line 17-18, "derivatizationas" should read -- derivatization as --.

Column 18,
Line 13, "enzymaticallylabeled" should read -- enzymatically labeled --.
Line 58, "oligonucleotidepoly(rFrU)," should read -- oligonucleotide poly(rFrU), --.

Column 19,
Line 13, "unhybridizedprobes" should read -- unhybridized probes --.

Column 20,
Line 30, "necessarilyparticipate" should read -- necessarily participate --.

Column 22,
Line 12, "(1)" should read -- (I) --.

Column 27,
Lines 29-30, "5x10⁻14" should read -- $5 \times 10^{-14}$ --.

Column 29,
Line 18, "35S" should read -- $^{35}S$ --.

UNITED STATES PATENT AND TRADEMARK OFFICE
CERTIFICATE OF CORRECTION

PATENT NO. : 6,268,132 B1
DATED : July 31, 2001
INVENTOR(S) : Michael J. Conrad

It is certified that error appears in the above-identified patent and that said Letters Patent is hereby corrected as shown below:

Column 30,
Line 23, "of. Non-hydrogen" should read -- of non-hydrogen --.
Line 46, "target-specificD" should read -- target-specific D --.

Column 31,
Line 58, "replicationor" should read -- replication or --.

Column 32,
Line 26, "fluorescen tribonucleoside" should read -- fluorescent ribonucleoside --.

Column 38, claim 1,
Line 39, "=$R_{14}$OH" should read -- =$R_{14}$=OH --.

Signed and Sealed this

Twelfth Day of March, 2002

Attest:

Attesting Officer

JAMES E. ROGAN
Director of the United States Patent and Trademark Office

```
                        SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
           (A) ORGANISM: Chlamydia trachomatis
           (C) INDIVIDUAL ISOLATE: L2/434/Bu
           (G) CELL TYPE: Bacterium (vii) IMMEDIATE SOURCE:
           (A) LIBRARY: lambda 1059 recombinant
           (B) CLONE: lamdba gt11/L2/33

(viii) POSITION IN GENOME:
           (A) CHROMOSOME/SEGMENT: omp112 ORF (xi) SEQUENCE DESCRIPTION: SEQ ID NO:1:

AACGTTCGAG ACGGACACCC CTTAGGACGA CTTGGTTCG                               39

(2) INFORMATION FOR SEQ ID NO:2:

(i) SEQUENCE CHARACTERISTICS:
           (A) LENGTH: 39 base pairs
           (B) TYPE: nucleic acid
           (C) STRANDEDNESS: single
           (D) TOPOLOGY: linear (ii) MOLECULE TYPE: transcribed DNA or RNA (iii) HYPOTHETICAL: NO (iv) ANTI-SENSE: YES (ix) FEATURE:
           (A) NAME/KEY: Complementary probe
           (C) IDENTIFICATION METHOD: Hybridization to SEQ ID NO. 1
           (D) OTHER INFORMATION: Control for SEQ ID NO. 3

(xi) SEQUENCE DESCRIPTION: SEQ ID NO:2:

TTGCAAGCTC TGCCTGTGGG GAATCCTGCT GAACCAAGC                               39

(2) INFORMATION FOR SEQ ID NO:3:

(i) SEQUENCE CHARACTERISTICS:
           (A) LENGTH: 39 base pairs
           (B) TYPE: nucleic acid
           (C) STRANDEDNESS: single
           (D) TOPOLOGY: linear
```

```
        (ii) MOLECULE TYPE: transcribed DNA or RNA (iii) HYPOTHETICAL: NO (iv) ANTI-SENSE: YES (ix) FEATURE:
            (A) NAME/KEY: Analogous complementary probe
            (C) IDENTIFICATION METHOD: Hybridization to SEQ ID NO. 1
            (D) OTHER INFORMATION: Analog to SEQ ID NO. 2

(xi) SEQUENCE DESCRIPTION: SEQ ID NO:3:

TTGCNNGCTC TGCCTGTGGG GNNTCCTGCT GNNCCNNGC                                    39
```